(12) United States Patent
Shimizu et al.

(10) Patent No.: US 11,678,888 B2
(45) Date of Patent: Jun. 20, 2023

(54) DEVICES FOR VASCULAR OCCLUSION

(71) Applicant: MicroVention, Inc., Aliso Viejo, CA (US)

(72) Inventors: Jared Shimizu, Irvine, CA (US); Heath Bowman, Trabuco Canyon, CA (US); Kiet Lam, Moreno Valley, CA (US); Rohini Retarekar, Columbia, MD (US); Maria Moreno, Anaheim, CA (US); Rogelio Cortez, Laguna Hills, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 185 days.

(21) Appl. No.: 16/914,126

(22) Filed: Jun. 26, 2020

(65) Prior Publication Data

US 2020/0323534 A1    Oct. 15, 2020

Related U.S. Application Data

(63) Continuation of application No. 15/430,419, filed on Feb. 10, 2017, now Pat. No. 10,729,447.

(Continued)

(51) Int. Cl.
*A61B 17/12* (2006.01)
*D04C 3/48* (2006.01)
(Continued)

(52) U.S. Cl.
CPC ...... *A61B 17/1214* (2013.01); *A61B 17/1215* (2013.01); *A61B 17/12031* (2013.01); *A61B 17/12113* (2013.01); *A61B 17/12145*
(2013.01); *A61B 17/12168* (2013.01); *A61B 17/12172* (2013.01); *A61M 25/0021* (2013.01); *B21F 3/04* (2013.01); *B21F 45/008* (2013.01);
(Continued)

(58) Field of Classification Search
CPC ........ A61B 17/12113; A61B 17/12168; A61B 17/1214; A61B 2017/12068; A61B 2017/12054–2017/12095
See application file for complete search history.

(56) References Cited

U.S. PATENT DOCUMENTS 4,655,762 A    4/1987 Rogers
5,645,082 A *  7/1997 Sung ............... A61B 17/1214
                                                 128/897
(Continued)

FOREIGN PATENT DOCUMENTS

CN    100589779 C    2/2010
CN    102481436 A    5/2012
(Continued)

OTHER PUBLICATIONS

China Patent Office, Office Action dated Oct. 12, 2021 with English translation in Chinese Patent Application No. 201780022213.6, 13 pages.

(Continued)

*Primary Examiner* — Kathleen S Holwerda
(74) *Attorney, Agent, or Firm* — Inskeep IP Group, Inc.

(57) ABSTRACT

An occlusive device, occlusive device delivery system, method of using, and method of delivering an occlusive device, and method of making an occlusive device to treat various intravascular conditions is described.

15 Claims, 34 Drawing Sheets

Related U.S. Application Data

(60) Provisional application No. 62/293,710, filed on Feb. 10, 2016.

(51) Int. Cl.

| | | |
|---|---|---|
| *D04C 1/06* | (2006.01) | |
| *B21F 45/00* | (2006.01) | |
| *A61M 25/00* | (2006.01) | |
| *B21F 3/04* | (2006.01) | |
| *B29C 53/56* | (2006.01) | |
| *B29C 71/02* | (2006.01) | |
| *A61B 90/00* | (2016.01) | |
| *A61B 17/00* | (2006.01) | |
| *B29L 31/00* | (2006.01) | |

(52) U.S. Cl.
CPC ............. *B29C 53/56* (2013.01); *B29C 71/02* (2013.01); *D04C 1/06* (2013.01); *D04C 3/48* (2013.01); *A61B 2017/00526* (2013.01); *A61B 2017/00862* (2013.01); *A61B 2017/00867* (2013.01); *A61B 2017/12054* (2013.01); *A61B 2017/12063* (2013.01); *A61B 2017/12068* (2013.01); *A61B 2090/3966* (2016.02); *A61M 2025/0042* (2013.01); *B29L 2031/7546* (2013.01); *D10B 2509/06* (2013.01)

(56) References Cited

U.S. PATENT DOCUMENTS

| | | | |
|---|---|---|---|
| 5,928,260 | A | 7/1999 | Chin et al. |
| 5,964,797 | A | 10/1999 | Ho |
| 6,086,577 | A | 7/2000 | Ken et al. |
| 6,146,373 | A | 11/2000 | Cragg et al. |
| 6,296,662 | B1 | 10/2001 | Caffey |
| 6,346,117 | B1 | 2/2002 | Greenhalgh |
| 6,375,668 | B1 | 4/2002 | Gifford et al. |
| 6,428,558 | B1 | 8/2002 | Jones et al. |
| 6,478,773 | B1 | 11/2002 | Ghandi et al. |
| 6,478,779 | B1 | 11/2002 | Hu |
| 6,511,468 | B1 | 1/2003 | Cragg et al. |
| 6,524,274 | B1 | 2/2003 | Rosenthal et al. |
| 6,558,367 | B1 | 5/2003 | Cragg et al. |
| 6,589,265 | B1 | 7/2003 | Palmer et al. |
| 6,613,074 | B1 | 9/2003 | Mitelberg et al. |
| 6,953,472 | B2 | 10/2005 | Palmer et al. |
| 6,964,657 | B2 | 11/2005 | Cragg et al. |
| 7,896,899 | B2 | 3/2011 | Mazzocchi et al. |
| 7,976,527 | B2 | 7/2011 | Cragg et al. |
| 8,016,799 | B2 | 9/2011 | Nash et al. |
| 8,048,104 | B2 | 11/2011 | Monstadt et al. |
| 8,066,732 | B2 | 11/2011 | Paul et al. |
| 8,066,733 | B2 | 11/2011 | Paul et al. |
| 8,267,955 | B2 | 9/2012 | Patterson et al. |
| 8,454,649 | B2 | 6/2012 | Cragg et al. |
| 8,480,701 | B2 | 7/2013 | Monstadt |
| 8,597,321 | B2 | 12/2013 | Monstadt et al. |
| 8,715,314 | B1 | 5/2014 | Janardhan et al. |
| 8,764,787 | B2 | 7/2014 | Ren |
| 8,845,676 | B2 | 9/2014 | Monstadt et al. |
| 9,060,777 | B1 | 6/2015 | Wallace et al. |
| 9,877,726 | B2 | 1/2018 | Lieu et al. |
| 2002/0111646 | A1* | 8/2002 | Gifford ............. A61B 17/1214 606/108 |
| 2002/0143348 | A1 | 10/2002 | Wallace et al. |
| 2003/0040733 | A1 | 2/2003 | Cragg et al. |
| 2003/0225365 | A1 | 12/2003 | Greff et al. |
| 2003/0225391 | A1 | 12/2003 | Cragg et al. |
| 2004/0225279 | A1 | 11/2004 | Raymond |
| 2006/0064151 | A1 | 3/2006 | Guterman et al. |
| 2006/0200234 | A1 | 9/2006 | Hines |
| 2006/0229702 | A1 | 10/2006 | Agnew |
| 2007/0043391 | A1 | 2/2007 | Moszner et al. |
| 2007/0088387 | A1 | 4/2007 | Eskridge et al. |
| 2007/0106311 | A1 | 5/2007 | Wallace et al. |
| 2007/0156117 | A1 | 7/2007 | Adams et al. |
| 2007/0162107 | A1 | 7/2007 | Haug et al. |
| 2007/0213765 | A1 | 9/2007 | Adams et al. |
| 2007/0248640 | A1 | 10/2007 | Karabey et al. |
| 2008/0045922 | A1 | 2/2008 | Cragg et al. |
| 2008/0281350 | A1 | 11/2008 | Sepetka et al. |
| 2008/0287982 | A1 | 11/2008 | Harreld |
| 2009/0163780 | A1 | 6/2009 | Tieu |
| 2009/0227976 | A1 | 9/2009 | Calabria et al. |
| 2009/0264858 | A1 | 10/2009 | Nash et al. |
| 2009/0287294 | A1 | 11/2009 | Rosqueta et al. |
| 2010/0049165 | A1 | 2/2010 | Sutherland et al. |
| 2010/0268204 | A1 | 10/2010 | Tieu et al. |
| 2011/0046658 | A1 | 2/2011 | Connor et al. |
| 2011/0092956 | A1 | 4/2011 | Soer et al. |
| 2011/0118768 | A1 | 5/2011 | Tran et al. |
| 2011/0152993 | A1 | 6/2011 | Marchand et al. |
| 2011/0196413 | A1 | 8/2011 | Wallace et al. |
| 2011/0202085 | A1 | 8/2011 | Loganathan et al. |
| 2011/0264073 | A1 | 10/2011 | Cragg et al. |
| 2011/0295298 | A1 | 12/2011 | Moszner |
| 2011/0301686 | A1 | 12/2011 | Bowman et al. |
| 2011/0319928 | A1 | 12/2011 | Griffin et al. |
| 2012/0157854 | A1 | 6/2012 | Kurrus et al. |
| 2012/0323267 | A1 | 12/2012 | Ren |
| 2012/0330348 | A1 | 12/2012 | Strauss et al. |
| 2013/0066357 | A1 | 3/2013 | Aboytes et al. |
| 2013/0116722 | A1 | 5/2013 | Aboytes et al. |
| 2013/0178886 | A1 | 7/2013 | Liu et al. |
| 2013/0184660 | A1 | 7/2013 | Swiss et al. |
| 2013/0204234 | A1 | 8/2013 | Cully |
| 2013/0204289 | A1 | 8/2013 | Dasnurkar et al. |
| 2013/0211443 | A1 | 8/2013 | Cragg et al. |
| 2013/0245667 | A1 | 9/2013 | Marchand et al. |
| 2013/0253572 | A1 | 9/2013 | Molaei et al. |
| 2013/0338643 | A1 | 12/2013 | De Silva |
| 2014/0012307 | A1 | 1/2014 | Franano et al. |
| 2014/0039459 | A1 | 2/2014 | Folk et al. |
| 2014/0135737 | A1 | 5/2014 | Sutherland et al. |
| 2014/0135810 | A1 | 5/2014 | Divino et al. |
| 2014/0135812 | A1 | 5/2014 | Divino et al. |
| 2014/0277099 | A1 | 9/2014 | Wallace et al. |
| 2015/0005804 | A1* | 1/2015 | Franano ............. A61B 17/12113 606/195 |
| 2015/0005810 | A1 | 1/2015 | Center et al. |
| 2015/0173772 | A1 | 6/2015 | Bowman et al. |
| 2015/0297240 | A1 | 10/2015 | Divino et al. |
| 2017/0189160 | A1 | 7/2017 | Krahbichler |

FOREIGN PATENT DOCUMENTS

| | | |
|---|---|---|
| CN | 104168844 A | 11/2014 |
| DE | 102007025466 A1 | 12/2008 |
| DE | 102012112732 A1 | 6/2014 |
| EP | 1516598 A1 | 3/2005 |
| EP | 1001707 B1 | 3/2006 |
| EP | 2676696 A1 | 12/2013 |
| EP | 2926744 A1 | 10/2015 |
| EP | 2932921 A1 | 10/2015 |
| FR | 2943905 A1 | 10/2010 |
| JP | 56-43962 A | 4/1981 |
| JP | H07265431 A | 10/1995 |
| JP | 2001509414 A | 7/2001 |
| JP | 2006-181088 A | 7/2006 |
| JP | 2008515468 A | 5/2008 |
| JP | 2012005846 A | 1/2012 |
| JP | 2012500102 A | 1/2012 |
| JP | 2013212372 A | 10/2013 |
| JP | 2014-061440 A | 4/2014 |
| WO | WO99/02094 A1 | 1/1999 |
| WO | WO99/62432 A1 | 12/1999 |
| WO | WO 2006/052322 A2 | 5/2006 |
| WO | WO2006074060 A2 | 7/2006 |
| WO | WO2008/011626 A1 | 1/2008 |
| WO | WO2010/022180 A1 | 2/2010 |
| WO | WO2012004165 A1 | 1/2012 |

(56) References Cited

FOREIGN PATENT DOCUMENTS

| WO | WO 2014/150288 A2 | 9/2014 |
| WO | WO 2015/171268 A2 | 11/2015 |

OTHER PUBLICATIONS

China Patent Office, Office Action dated Jul. 2, 2021 with English translation in Chinese Patent Application No. 201811271182.0, 14 pages.

Japan Patent Office, Official Action dated Dec. 8, 2020 in Japanese Patent Application Serial No. 2019-221239 with English translation, 7 pages.

Japan Patent Office, Official Action dated Aug. 6, 2019 in Japanese Patent Application Serial No. 2018-089889 with English translation, 4 pages.

Japan Patent Office, Examination Report dated Mar. 27, 2019 in Japanese Patent Application No. 2018-089889, 7 pages.

European Patent Office, Supplementary European Search Report dated Aug. 16, 2017 in European Patent Application No. EP14871037.9, 8 pages.

WIPO, U.S. International Search Authority, International Search Report and Written Opinion dated Apr. 20, 2015 in International Patent Application No. PCT/US2014/071677, 10 pages.

Bormashenko, E. et al., "Electrically Controlled Membranes Exploiting Cassie-Wenzel Wetting Transitions," *Scientific Reports*, 3:3028, Oct. 23, 2013, pp. 5 pages.

United States Patent and Trademark Office, Final Office Action dated Sep. 10, 2020 in U.S. Appl. No. 15/430,414, 19 pages.

China Patent Office, Office Action dated Sep. 27, 2020 with English translation in Chinese Patent Application No. 201780022213.6, 11 pages.

China Patent Office, Office Action dated Nov. 18, 2020 with English translation in Chinese Patent Application No. 201811271182.0, 8 pages.

Japan Patent Office, Office Action dated Feb. 9, 2021 with English translation in Japanese Patent Application No. 2018-542213, 9 pages.

WIPO, U.S. International Search Authority, International Search Report and Written Opinion dated May 26, 2017 in International Patent Application No. PCT/US2017/017557, 14 pages.

Japan Patent Office, Office Action after Appeal dated Sep. 20, 2022 with English translation in Japanese Patent Application No. 2019-113124, 9 pages.

European Patent Office, Extended European Search Report dated Jan. 27, 2023 in European Patent Application No. 22197264.9, 10 pages.

United States Patent and Trademark Office, Office Action dated Nov. 25, 2022 in U.S. Appl. No. 17/179,287, 25 pages.

\* cited by examiner

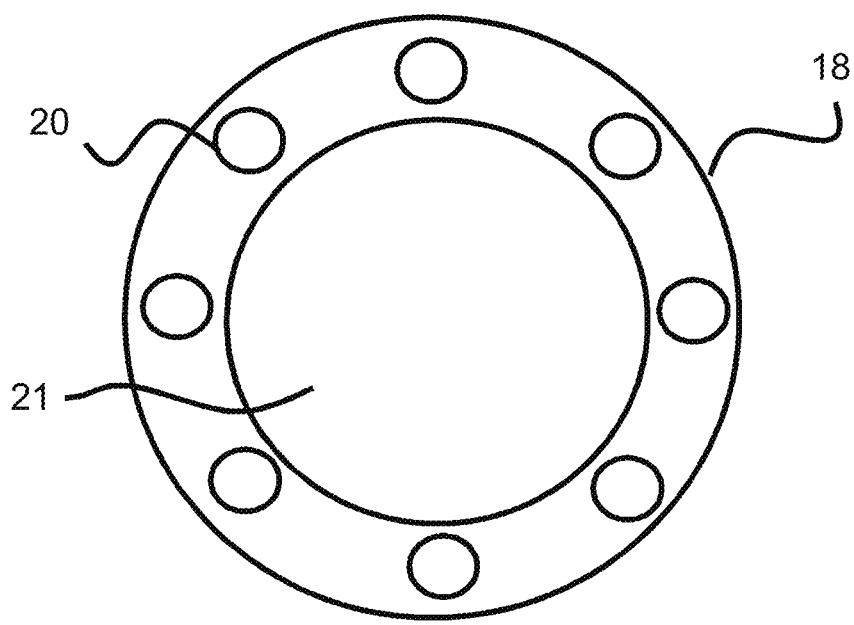
Figure 3
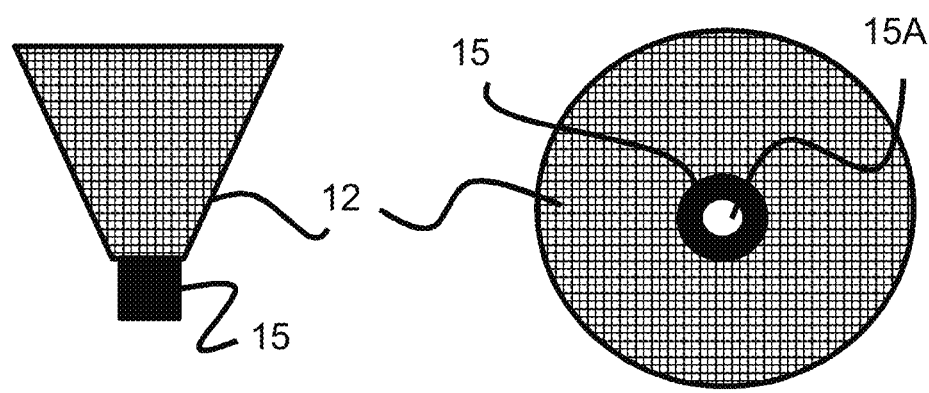
Figure 4A
Figure 4B
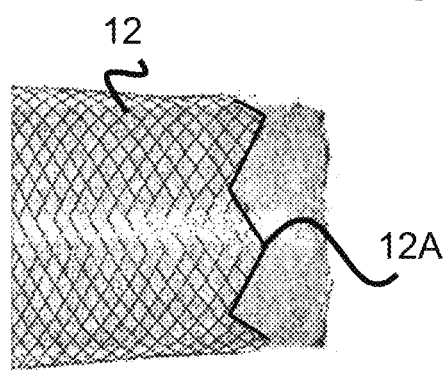
Figure 4C

DEVICES FOR VASCULAR OCCLUSION

RELATED APPLICATIONS

This application is a continuation of and claims priority to U.S. patent application Ser. No. 15/430,419 filed Feb. 10, 2017 entitled Devices For Vascular Occlusion, which claims benefit of and priority to U.S. Provisional Application Ser. No. 62/293,710 filed Feb. 10, 2016 entitled Devices for Vascular Occlusion, both of which are hereby incorporated herein by reference in their entireties.

BACKGROUND OF THE INVENTION

Vessel occlusion is often necessary in a variety of cases—including but not limited to treatment of aneurysms, atrial septal defects, patent foramen ovale, left atrial appendage occlusion, patent ductus arteriosus, fistula, arterio-venous malformations, fallopian tube occlusion for the purposes of sterilization, and occlusion in the peripheral vasculature. One method of vessel occlusion involves filling the vessel or malformation or aneurysm with occlusive devices for the purposes of embolization. Typically, embolic coils are used for this purpose.

Successful occlusion can be difficult due to the complex geometries potentially associated with the various target areas of the vasculature. An occlusive device which can conform to the complex shapes associated with the vasculature, and which can quickly occlude a target area is therefore desirable.

SUMMARY OF THE INVENTION

An occlusive device is described.

In one embodiment, the occlusive device comprises a retention portion and a holding portion. In one embodiment, the retention portion is clover-shaped and the distal holding portion is a cylindrical mesh.

In one embodiment, the occlusive device comprises a retention portion and holding portion, where another occluding device can be used to fill the holding portion.

In one embodiment, the occlusive device comprises a retention portion and holding portion and an attached delivery tube through which additional occluding devices can be delivered to fill the holding portion.

In one embodiment, the occlusive device comprises one or more disc shaped elements.

In one embodiment, the occlusive device comprises one or more disc shaped elements and a central element traversing through at least some of the disc shaped elements.

In one embodiment, the occlusive device comprises a ribbon-shape. In one embodiment, the occlusive device comprises a spiral-ribbon shape.

In one embodiment, the occlusive device comprises smaller and larger diameter regions. In one embodiment these smaller and larger diameter regions are sequential with a smaller diameter region alternating with a larger diameter region. In one embodiment, the smaller diameter regions utilize one substantially consistent shape and the larger diameter regions utilize another substantially consistent shape.

In one embodiment, a delivery system for delivering and detaching an occlusive device is described.

In one embodiment, an occlusive device utilizes a stretch resistant member to help control expansion of the occlusive device upon delivery.

In one embodiment, an occlusive device comprises an outer member and an inner member. In one embodiment, the inner and outer members are comprised of the same braided material, just packed into each other.

In one embodiment, an occlusive device comprises one or more sealing members, where the sealing members can be located on at least one of the proximal and/or distal ends of the device.

In another embodiment, an occlusive device comprises a structural portion, and a mesh or membrane portion over the structural portion.

In another embodiment, an occlusive device comprises a neck bridge element and one or more filling structures.

In another embodiment, an occlusive device comprises a neck bridge element and an embolic material, such as embolic coils.

In another embodiment, an occlusive device comprises structural struts and a distal contact portion.

In another embodiment, an occlusive device comprises two separate occlusive sections connected by a coil.

A method of manufacturing an occlusive device is also described.

In one embodiment, an occlusive device is manufactured by taking a center element and attaching one or more wires to this center element to create a retention portion. In one embodiment, an occlusive device is manufactured by taking a center element and passing one or more wires through this center element to create a retention portion. In one embodiment, the shape of this retention portion is clover-like. A holding portion, in one embodiment a mesh comprising wires, can then be attached to the retention portion.

In one embodiment, an occlusive device is manufactured by winding the occlusive device over one of more disc-shaped elements. The one or more disc shaped elements have a plurality of holes passing through which the constituent wires making up the occlusive device are wound through. The one or more disc shaped elements may optionally contain a center channel which the wires are pulled through in order to create a center element traversing through at least some of the disc-shaped elements.

In another embodiment, an occlusive device is manufactured by heat-setting the device over a mandrel with a shape comprising smaller and larger-diameter regions. In another embodiment, an occlusive device is manufactured over a mandrel with a relatively consistent diameter. Marker bands or tie elements are then selectively placed throughout the occlusive device to create smaller diameter regions throughout the length of the occlusive device.

In another embodiment, a braider utilizes both an inner and an outer braider to braid an occlusive device. The occlusive device may be wound over more than one mandrel, where the use of both and inner and outer braider can help speed up the manufacturing process.

In another embodiment, a tapered mandrel can be used with a braider to create an occlusive device comprising both an inner and an outer region.

In another embodiment, a removable mandrel can be used to wind an occlusive device.

In another embodiment, a vertical braider is described. The vertical braider may be used to manufacture an occlusive device.

In another embodiment, an implant comprising a closed end is braided over a mandrel utilizing a closed end and a series of pins on the closed end section to help create the closed end. The implant may be an occlusive device.

In another embodiment, a rotational braider is described. The rotational braider may be used to create an implant with regions of varying stiffness.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which:

FIG. 3 illustrates an occlusive device comprising a retention portion and a holding portion.

FIG. 4A illustrates an occlusive device comprising a retention portion and a holding portion.

FIG. 4B illustrates an occlusive device comprising a retention portion and a holding portion.

FIG. 4C illustrates an occlusive device comprising a retention portion and a holding portion.

DESCRIPTION OF EMBODIMENTS

Figure 1:
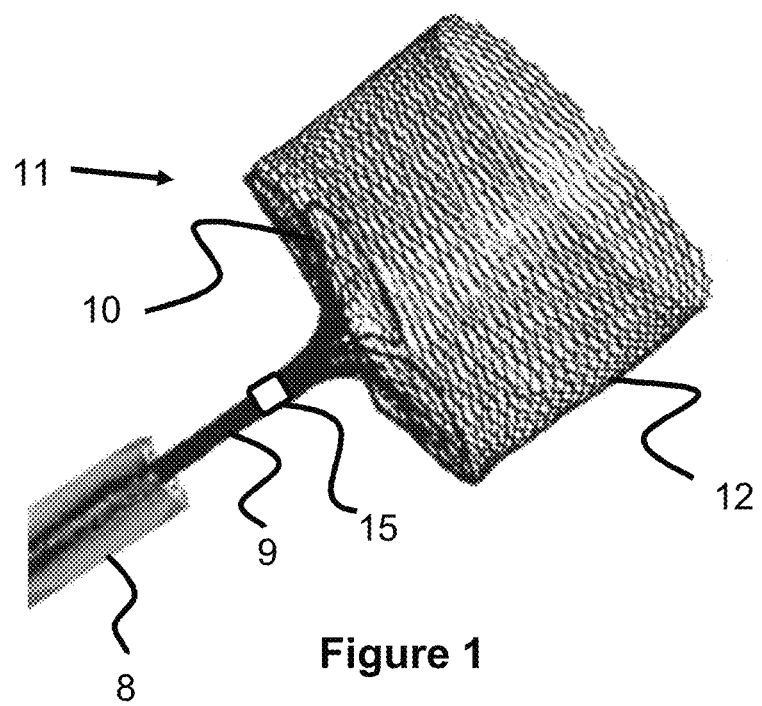
FIG. 1 illustrates an occlusive device comprising a retention portion and a holding portion.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

An occlusive and/or embolic device is described; the device may be used for a variety of purposes including—but not limited to—filling aneurysms, atrial septal defects, patent foramen ovale, left atrial appendage occlusion, patent ductus arteriosus, fistula, arterio-venous malformations, fallopian tube occlusion for the purposes of sterilization, and occlusion in the peripheral vasculature. Some of the embodiments described herein can be considered as intrasaccular devices.

For the purposes of illustrating the use of the embodiments described herein, treatment of aneurysms may be described for ease of illustration and consistency. However, the various embodiments of the device can be used for a number of purposes, including those described above, in addition to treating aneurysms.

Typical technologies to treat vascular conditions, such as aneurysms, utilize coils to fill the space or clips to cut off blood flow to the target areas. These technologies may have difficulty if the aneurysm/treatment area has a wide neck or complex shape, since placement and retention of the coils may be problematic. Intrasaccular devices aim to create a blockage at the neck of the aneurysm and to conform to the general shape of the aneurysm, thereby restricting blood flow from the neck into the aneurysm to occlude the target site. Examples of such devices can be found in commonly assigned US20140200607, which is hereby incorporated by reference in its entirety.

The intrasaccular devices described herein may also be combined with embolic coils, liquid embolic, or other embolic agents to augment the occlusive effect at the target site. Many of the embodiments disclosed in this specification are directed to a detachable intrasaccular device connected to a catheter that also allows embolic material to be delivered through its catheter. The catheter includes a passage extending along its length and opening within the intrasaccular device. Once the intrasaccular device is advanced to the target aneurysm and expanded, embolic agents, such as embolic coils or liquid embolic material, can be advanced through the catheter and out into the intrasaccular device and/or into the aneurysm. Finally, the intrasaccular device can be detached from the catheter. In this respect, the intrasaccular device can be deployed in an aneurysm first to block it off from the adjacent blood vessel, and the embolic agents can be subsequently delivered. This order of a treatment procedure may result in the embolic agents being better retained in the aneurysm versus delivering embolic agents first and then an intrasaccular device second. The aperture in the intrasaccular device can also or alternately be used to attach a tether or monofilament that is also connected to the catheter, allows for a detaching the intrasaccular device via a detachment mechanism within the catheter.

One embodiment of such an intrasaccular device 11 can be seen in FIGS. 1-5 The intrasaccular device 11, comprises a holding portion 12 for supporting a plurality of embolic coils 6, and a retention portion 10 that expands and supports a proximal end of the holding portion 12. As described in further detail below, the intrasaccular device 11 also includes an aperture connected to a passage in the microcatheter 9, which allows for the delivery of embolic agents after expansion and/or the connection of a tether to detachably retain the intrasaccular device 11.

The holding portion 12 is, in one example, composed of a plurality of wires woven into a mesh or braid, and further expands to a cylindrical or concave dish shape. As seen best in FIGS. 4A and 4B, the proximal end of the holding portion 12 terminates its mesh with a cylindrical proximal end member 15. This end member 15 preferably includes a passage 15A (see FIG. 4B) that connects between the proximal and distal sides of the holding portion 12.

In one example, the proximal end member 15 can be created by first gathering the proximal end of the mesh of the holding portion 12 and placing a relatively larger radiopaque marker band around it. A second, smaller marker band is lined up on the inside of the mesh and concentrically aligned with the larger marker band. Finally, the two marker bands are welded together. Since both marker bands are annular or ring-shaped, they create a proximal end member 15 with the passage 15A therethrough.

In another example, the proximal end member 15 can be created by feeding all of the braided wires of the holding portion's mesh through a middle of a radiopaque marker band. A mandrel with a poor welding ability (i.e., that tends not to melt at normal welding temperatures) is placed within the mesh and marker band, and the mesh and ring are welded, leaving the passage 15A through the resulting proximal end member 15.

In yet another example, the proximal end member 15 can be created by placing the braided wires of the holding portions mesh into and through a tube having poor welding characteristics. A mandrel, also having poor welding characteristics, is passed through the inside of the mesh, allowing the wires of the mesh to be welded together. The tube and mandrel are removed from the mesh, leaving the passage 15A through the resulting proximal end member 15. Optionally, an additional weld can be performed around the outside diameter of the device to increase the strength of the end member 15.

In another embodiment, the size of the proximal end member 15 can be reduced by first cutting a proximal end of initial braid of the holding portion 12 into pointed or triangular flaps 12A. For example, between 4 and 16 flaps can be created. The resulting flaps 12A can be brought together to form the proximal end member 15 in one of the above-mentioned techniques, resulting in an end member 15 that is substantially smaller than without creating the flaps 12A, due to a decrease in the number of wires being held together at the end member 15.

The retention portion 10, in one example, includes a plurality of loops 22 formed from one or more wires, and radially expands such that the loops 22 are substantially aligned in a single plane. The retention portion 10 includes a center element 18, shown in the top and side views of FIGS. 3 and 4, that retains the wires forming the loops 22. The center element includes a center aperture or lumen 21 and a plurality of smaller apertures 20. The center aperture 21 is preferably connected or aligned with the passage 15A of the holding portion 12, thereby creating a continuous passage between a passage in catheter 9, the passage 15A, and the aperture 21. This continuous passage allows embolic agents to be advance out into the intrasaccular device 11.

Figure 5:
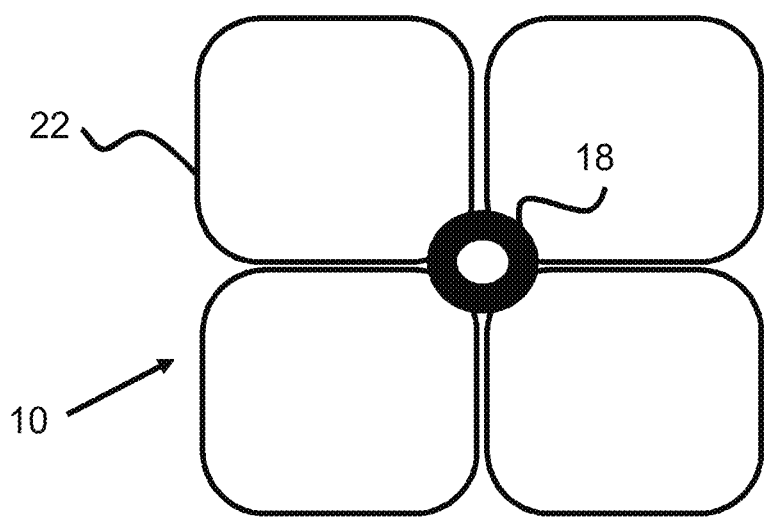
FIG. 5 illustrates an occlusive device comprising a retention portion and a holding portion.

A plurality of wires pass through the plurality of smaller apertures 20 to create a clover-like shape as shown in FIG. 5. Though four of these "clover leaf" loops 22 are shown in FIG. 5, fewer or more leafs can be used. In one example, each leaf can be formed from a single wire and one end of the wire is placed through a first hole, the other end of the wire is placed through the second hole. The two ends of the wire are welded or otherwise joined together. Thus, each leaf utilizes two of the holes on center element 18. In FIGS. 3-4, eight holes are shown which are respectively used with four leaves. In another example, the center element would include no holes, instead it is just a piece which the clover leaf wires are affixed to (via adhesive, mechanical ties, or welding).

Figure 7:
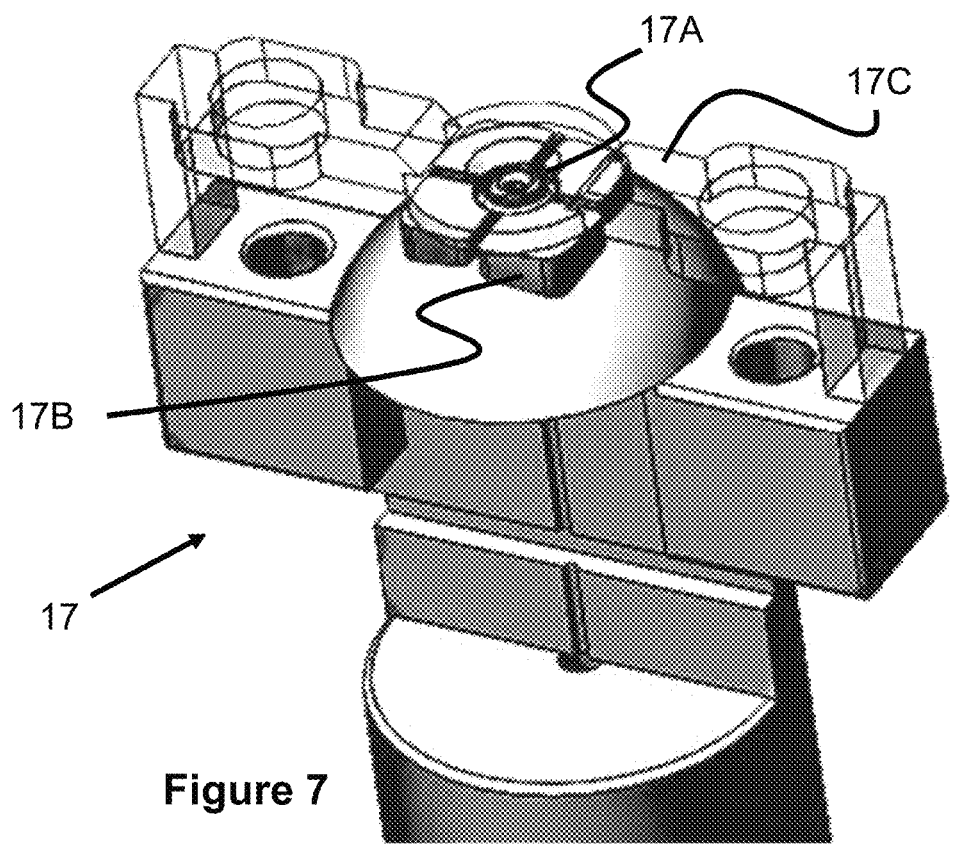
FIG. 7 illustrates a manufacturing element used to create a retention portion of an occlusive device.

FIG. 7 shows a mandrel or fixture 17 that can be used to create the retention portion 10. The fixture 17 includes a slot 17A to accommodate center element 18. Wires can be wound around the 'petal' shaped fixtures 17B to create the "clover-leaf" loops 22, a press 17C may optionally be used to press down on the device and hold the shape and a subsequent heat treating procedure can optionally be used as well.

Figure 2:
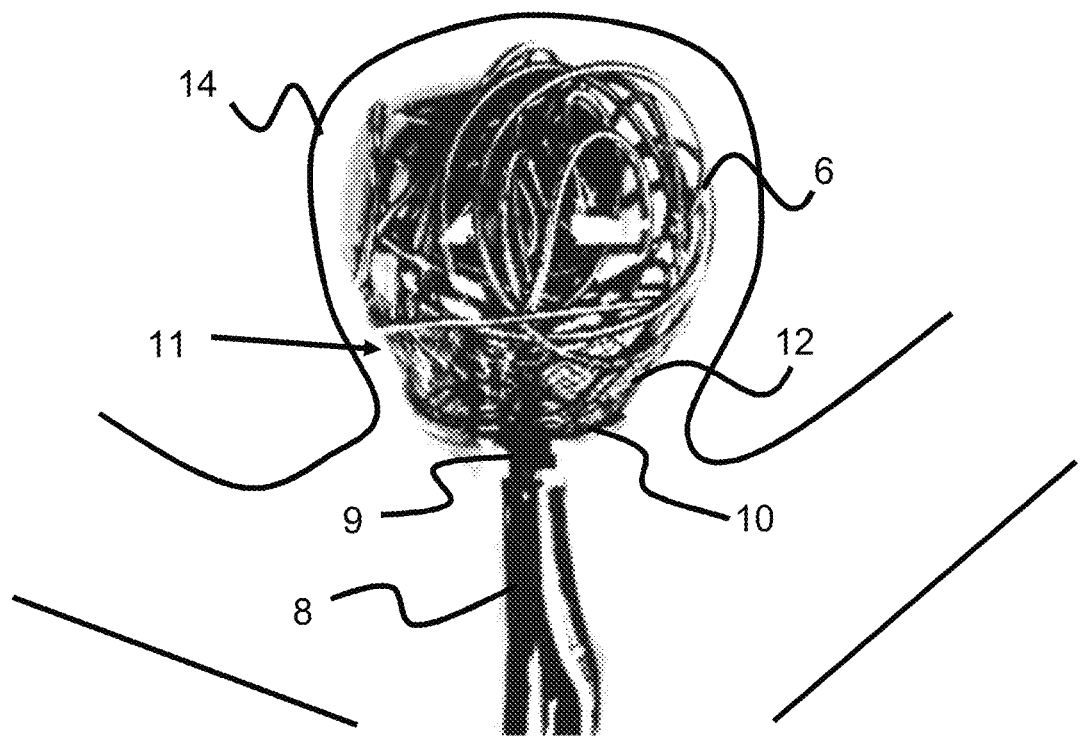
FIG. 2 illustrates an occlusive device comprising a retention portion and a holding portion.

The holding element 12 can be affixed to retention portion 10 via adhesive, mechanical ties, or welding. The holding element 12 is positioned across the proximal-facing part of the "clover leaf" loops 22 and then extends like a cylinder with walls projecting distally. Though the holding element 12 as shown in FIG. 1 has an open top, a closed top may be used. The holding element 12 can be comprised of a braid or mesh of wires, such as nitinol wires. Radiopaque material such as tantalum, platinum, gold, and/or palladium may also be used. In one example, the mesh solely comprises nitinol wires. In another example, the mesh comprises nitinol wires along with another radiopaque wire (such as the materials described above). In another example, wires comprising a radiopaque core and nitinol exterior or a nitinol core and a radiopaque exterior may be used. The retention portion 10, in one example, is positioned at the neck of the aneurysm while the holding element 12 is located in the interior of the aneurysm 14 in order to fill it, as best seen in FIG. 2.

The device 11 of FIG. 1 can be located within a larger delivery catheter 8, in which the device 11 itself is connected to a smaller microcatheter 9, which can either be tracked through the larger catheter 8 or is pre-placed within a distal part of the delivery catheter 8. The proximal end of the holding portion 12 of the device 11 can either sit flush with the center element 18 of retention portion 10, extend proximally past retention portion 10, or end roughly flush with either the back or the front of the "clover leaf" loops 22. In another example, the wire portions of the clover leaf loops 22 are located under the center element 18, since they pass through the apertures 20 of the center element 18 (see FIG. 3). This creates a type of basket (in the shape of FIG. 5, four loops would produce four wire basket protrusions), and the proximal end of mesh holding portion 12 would be located within this basket and be bound by the wires of this basket. Alternatively, the wires of the holding portion 12 can be directly affixed above or underneath the clover leaf loops 22 via adhesive, mechanical ties, or welding. If this technique is used, the mesh should be configured so as to not obstruct the center aperture 21 of center element 18. As will be explained later, this lumen can be used to deliver additional embolic agents and thus the lumen should be unobstructed.

In one embodiment, the occlusive device 11 of FIG. 1 is attached to a microcatheter 9, that is, the microcatheter 9 is connected to the center element 18, holding portion 12, and retention portion 10 at the distal end of the microcatheter 9. This microcatheter 9 is delivered through a larger catheter 8, and the holding portion 12 and retention portion 10 assume a collapsed configuration when within this larger catheter 8. In this collapsed configuration, the retention portion clover leaf loops 22 are pushed together (akin to a flower bud before blossoming) and are located past the distal end of the microcatheter, where the holding portion is located further distally, also in a collapsed configuration. The larger delivery catheter 8 is either retracted to expose the microcatheter 9 and the attached occlusive device 11, or the microcatheter 9 is pushed out of the distal end of the delivery catheter 8 to expose the device. Upon exposure, the holding and retention portion assume their expanded configuration as shown in FIG. 1. The lumen of the microcatheter 9, after placement of the occlusive device 11 within the target treatment site 14, then can be used to deliver additional embolic agents such as embolic coils 6 or liquid embolic material, as best seen in FIG. 2.

Another embodiment may solely use the retention portion 10 and no holding portion 12. In such an embodiment, the retention portion would be used solely to prevent subsequently delivered embolic coils from falling out of the neck of the aneurysm 14. Another embodiment may utilize a retention portion 10 with a mesh layer lying either above, under, or completely surrounding both sides of the "clover leaf" loops 22 of the retention portion 10. The mesh provides an occlusive effect to limit the amount of blood flow coming into the aneurysm (that is, the mesh itself provides a barrier to blood entry). Any optional subsequently introduced embolic agents such as embolic coils or liquid embolic would then augment the occlusion within the aneurysm/treatment site. For example, after the occlusive device 11 is placed at the target treatment site and any optional embolic materials (i.e. coils, liquid embolic, or other embolic agents) are introduced through the microcatheter 9, the occlusive device 11 is detached from the microcatheter to remain at the treatment site, allowing the microcatheter 9 to be withdrawn.

A detachment system can be utilized with center element 18 of retention element 10. Detachable tip devices are known in the art in order to detach a distal section of a microcatheter, and are often used with liquid embolic delivery systems so that if a distal section of the catheter is stuck or "glued" to the delivered liquid embolic, it can be detached so the rest of the catheter can be withdrawn. A detachable tip can be utilized with center element 18, thus the microcatheter would have center element 16 and retention element 10 built onto the distal tip of said microcatheter. An electrolytic, thermal, or mechanical detachment system can be used to sever the center element from the microcatheter and leave the occlusive device at the target treatment site. Alternatively, the detachment junction may be located proximal to the center element, for example the detachable tip element may be connected to center element 16, but placed proximally of said center element. U.S. Pub. 2015/0137773 discloses several detachable tip system embodiments which may be utilized with this embodiment, and is hereby incorporated by reference in its entirety.

Figure 33A:
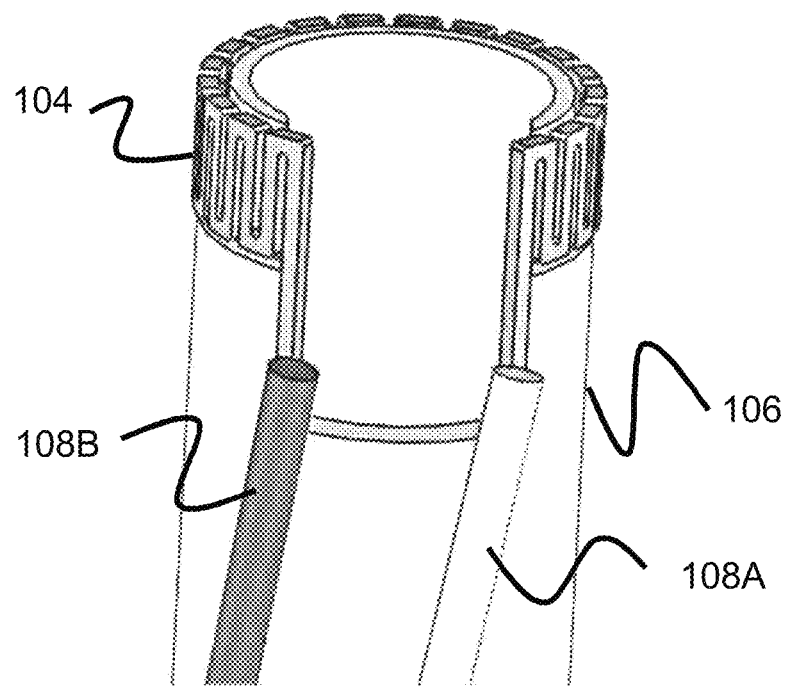
FIG. 33A illustrates a detachment system used with an occlusive device.
Figure 33B:
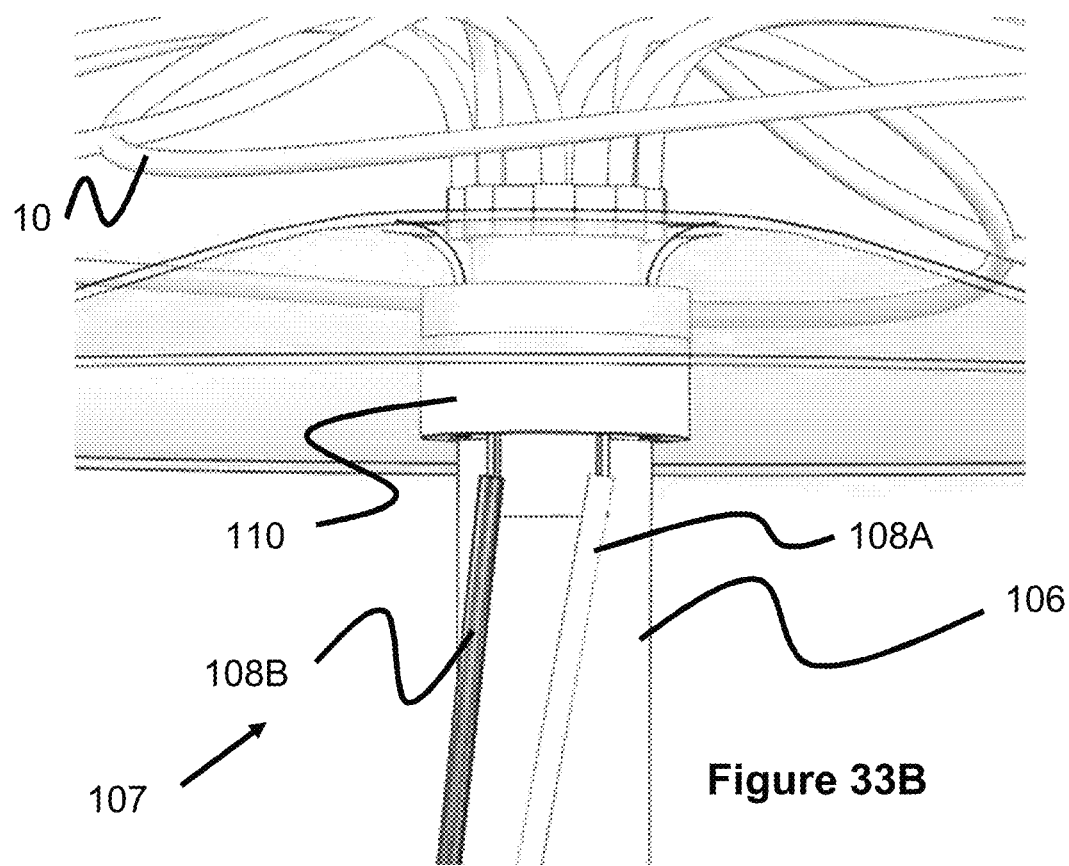
FIG. 33B illustrates a detachment system used with an occlusive device.
Figure 33C:
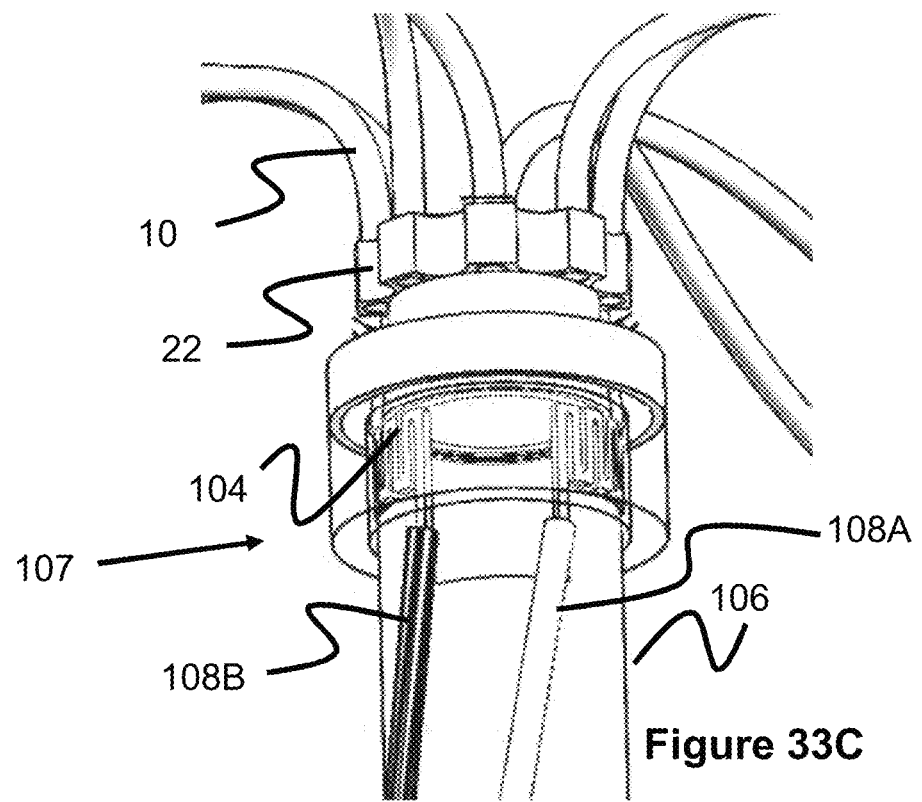
FIG. 33C illustrates a detachment system used with an occlusive device.
Figure 33D:
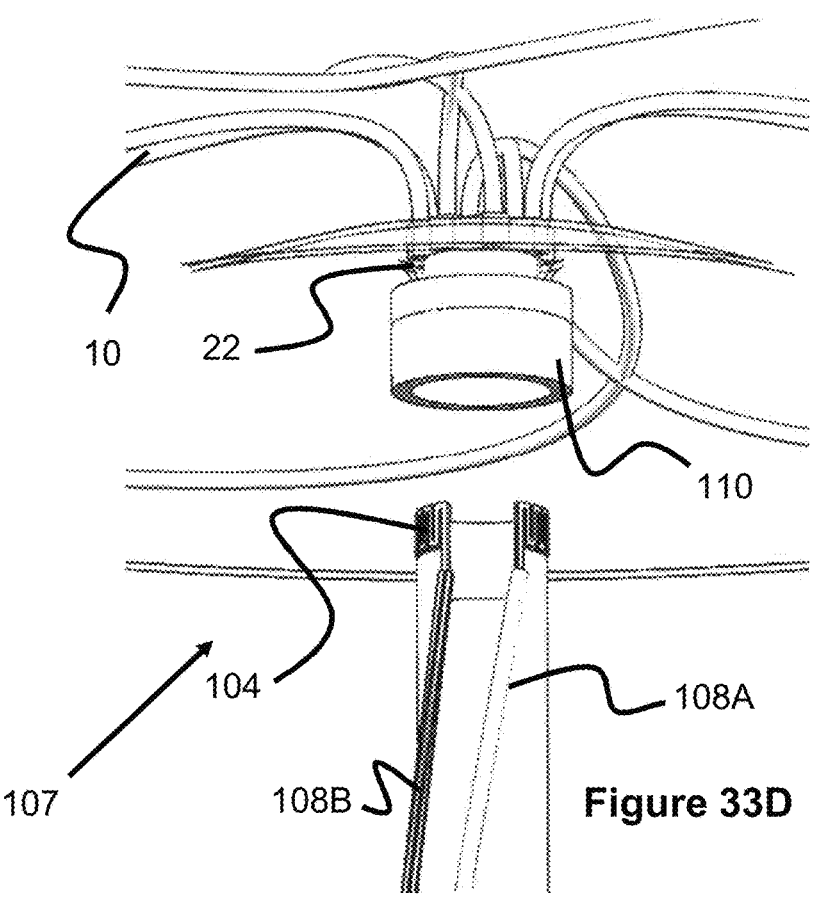
FIG. 33D illustrates a detachment system used with an occlusive device.
Figure 33E:
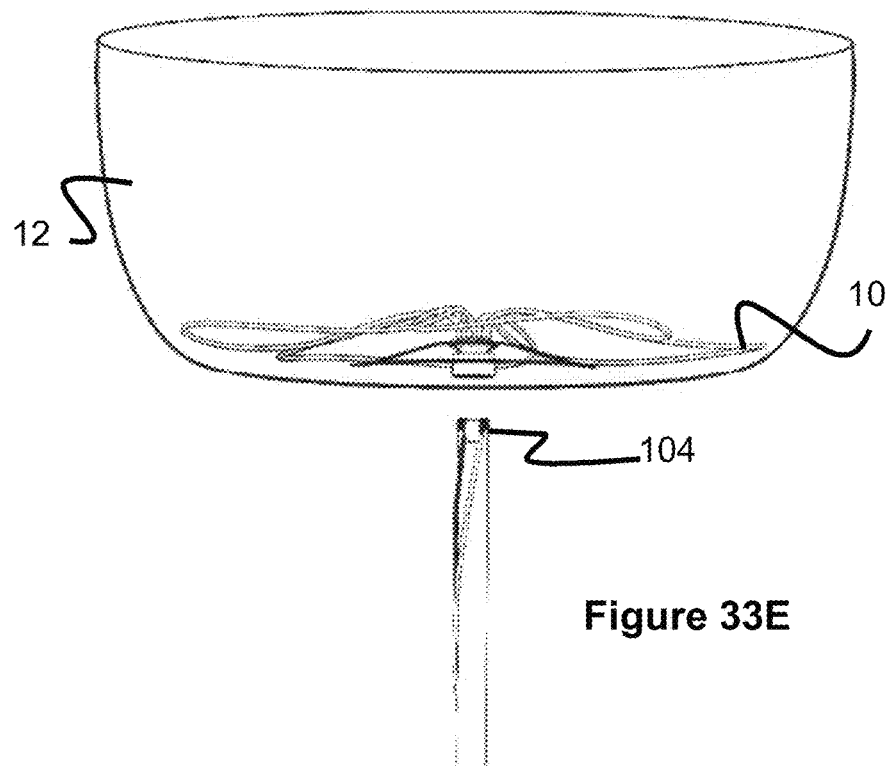
FIG. 33E illustrates a detachment system used with an occlusive device.

FIGS. 33A-33E illustrate a unique detachment system 107 that can be used with the occlusive device 11 shown in FIG. 1, as well as any of the other occlusive devices described in this specification. Unlike other prior art detachment systems, the embodiment of FIGS. 33A-33E shows a detachment system able to accommodate the center aperture or lumen 21 (best seen in FIG. 3). One of the embodiments of this device 107 utilized the occlusive device 11 connected to the distal end of a smaller microcatheter or delivery tube 106, where the device 107 itself is delivered through another larger catheter. The detachment system 107 allows the microcatheter or delivery tube 106 connected to the occlusive device 11 to detach from the occlusive device 11 at an appropriate time. For example, the occlusive device 11 is placed in an aneurysm, the attached microcatheter 106 would be used to deliver additional embolic agents (such as liquid embolic or coils), and then the microcatheter 106 is detached and removed, leaving the occlusive device 11 in place. The detachment system 107 utilizes a heater 104 in the distal region of attached microcatheter 106. Heater 104 can be a resistive wire coil or a laser cut sheet of various patterns (e.g., the square wave pattern shown in the figures). Wires 108a and 108b connect in two locations to the heater 104 supplied by a voltage source at the proximal end of the device 107 so each wire is oppositely polarized, allowing the heater 104 to convey a current. Cylindrical cover 110 sits over the heater 104, and there can be a sacrificial polymer layer or adhesive layer between cover 110 and heater 104. The operating principal is that the heat generated by the heater 104 will sever the sacrificial layer and detach microcatheter 106 from cover 110, leaving the microcatheter free to retract from the vasculature, as shown in FIGS. 33D and 33E.

In FIG. 33A, both the sacrificial polymer or adhesive layer and the heater are shown as extending more than 180 degrees but less than 360 degrees around the aperture or lumen. Various configurations are possible. For instance, the sacrificial inner polymer or adhesive layer which is melted by the heater may extend in selective, non-continuous segments around the periphery of the aperture. The heater and sacrificial layer can extend a full 360 degrees or close to 360 degrees around the aperture. One of the heater or sacrificial layer can extend a full 360 degrees around the aperture while the other element extends less than 360 degrees around the aperture. It is preferable that the sacrificial layer extends at least 180 degrees around the aperture, while the heater should at least cover the breadth of the sacrificial layer.

A method of operation utilizing the occlusive device 11 of FIG. 1 and detachment system 107 of FIGS. 33A-33E involves having an occlusive device 11 with attached microcatheter 106 and delivering this system through a larger catheter. When the occlusive device 11 is appropriately placed, additional embolic agents may optionally be delivered through attached microcatheter 106, then the detachment sequence is initiated to detach microcatheter 106 from the occlusive device 11, and the microcatheter 106 is subsequently withdrawn.

Figure 34A:
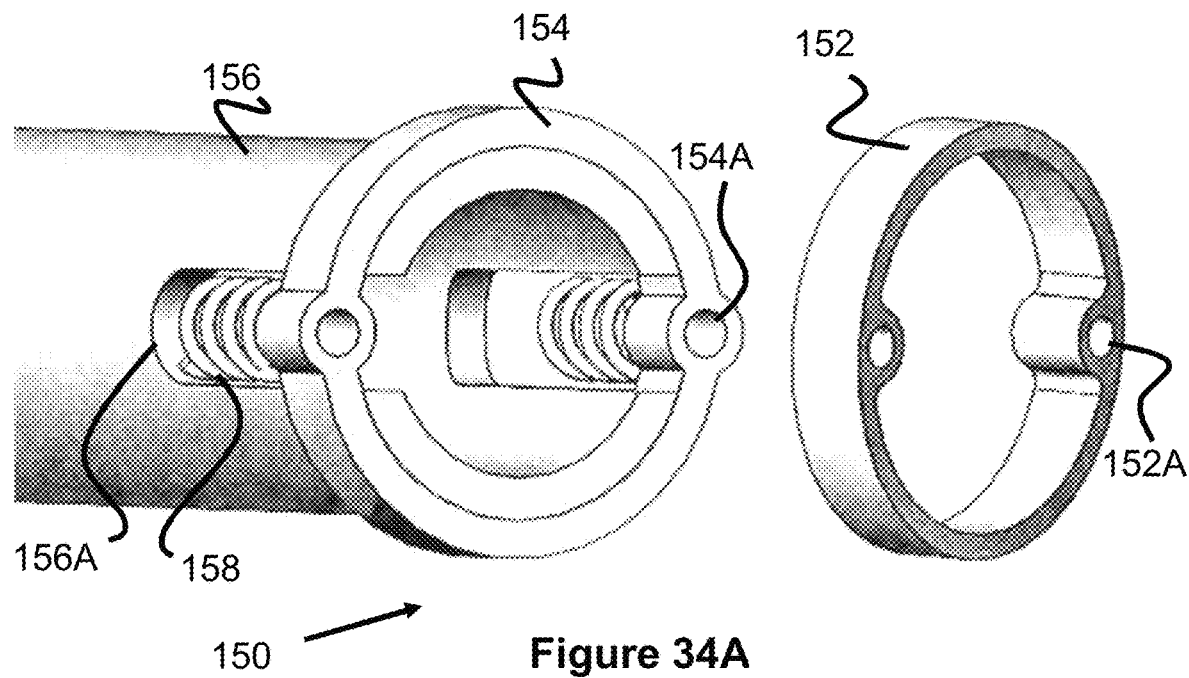
FIG. 34A illustrates a detachment system used with an occlusive device.
Figure 34B:
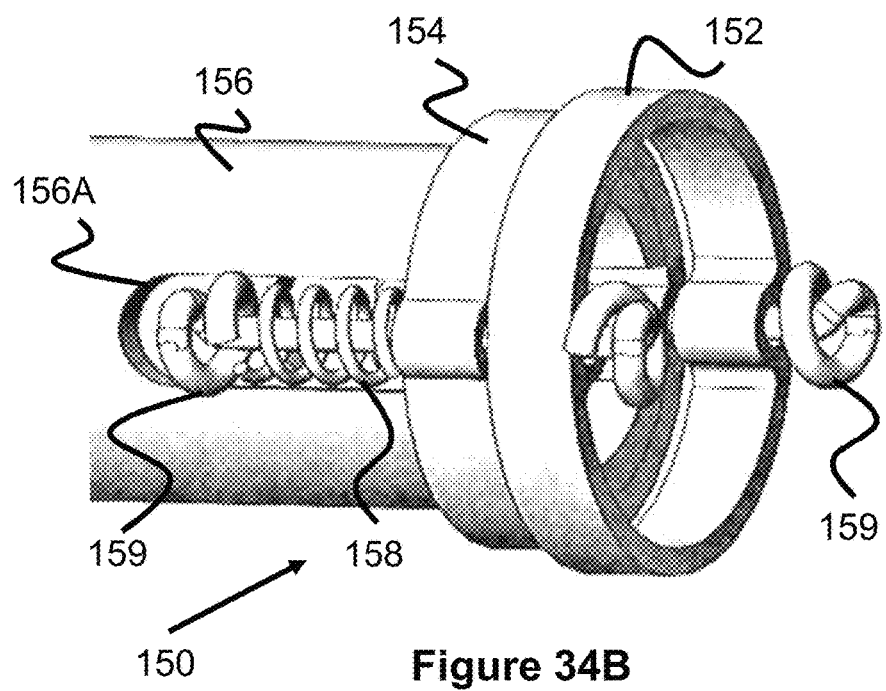
FIG. 34B illustrates a detachment system used with an occlusive device.

FIGS. 34A and 34B illustrate another embodiment of an occlusive device detachment system 150 that can be used with the occlusive device 11, as well as any of the other occlusive devices described in this specification. As seen in FIG. 34B, the system 150 uses two tethers 159 that are attached to a device coupling ring 152 on the proximal end of an occlusive device and to the tubular pusher body 156. Each tether 159 is surrounded by a heater coil 158 that are connected to a selectively activated power supply which, when activated, increase in temperature and break the tether 159, releasing the device coupling ring 152 and the occlusive device it is connected to.

The heater coils 158 are preferably located within two oppositely positioned channels cut into the tubular pusher body 156. The passage within the heater coils 158 are each aligned with apertures 154A through a pusher coupling ring 154. Similarly, the device coupling ring 152 includes two apertures 152A that are oppositely or diametrically positioned from each other and that can be aligned with the apertures 154A. The tether 159 is tied or fixed on the distal side of the apertures 152A, passing through the apertures 152A, through the apertures 154A, through the heater coil 158, and tied/fixed proximally of the heat coil 158 and within the slot 156A.

If the occlusive device includes a braid or mesh, similar to the device 11, it is attached to the device coupling ring 152 by first feeding the mesh through the main opening of the ring 152 and then placing an inner mandrel matching the size of the central lumen of the pusher tube 156 within the middle of the captured mesh. The end of the mesh is then welded to the ring 152 and the mandrel is removed, leaving a passage in the occlusive device. Since the main opening of the pusher coupling ring 154 is sized and positioned over an end of the pusher tube 156, the central lumen of the pusher tube 156 aligns with the passage created by the device coupling ring 152 and mesh of the occlusive device. This allows embolic agents to be advanced through the central pusher lumen and through the occlusive device, prior to the occlusive device being detached.

Figure 6:
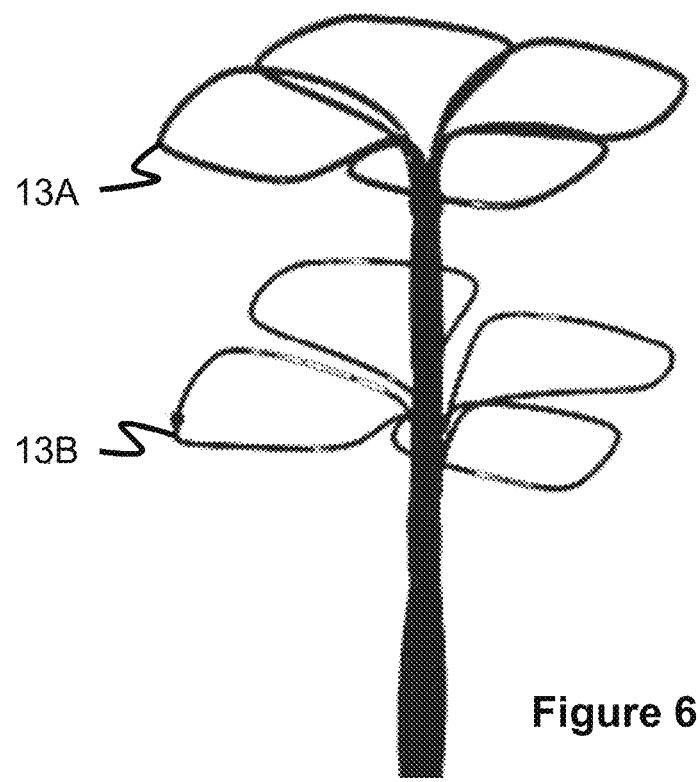
FIG. 6 illustrates an occlusive device, comprising multiple retention portions.

Multiple retention portions 10 can be used, as shown in FIG. 6. The more-proximal retention portion 13b is placed at the neck of the aneurysm and the distal retention portion 13a is placed further within the aneurysm. This embodiment may also be used with the holding element 12 of FIG. 1, in which the distal retention portion 10b is located at the distal end of the holding element 12. The detachment occurs at the retention portion 13b using the heating techniques described above.

Figure 8:
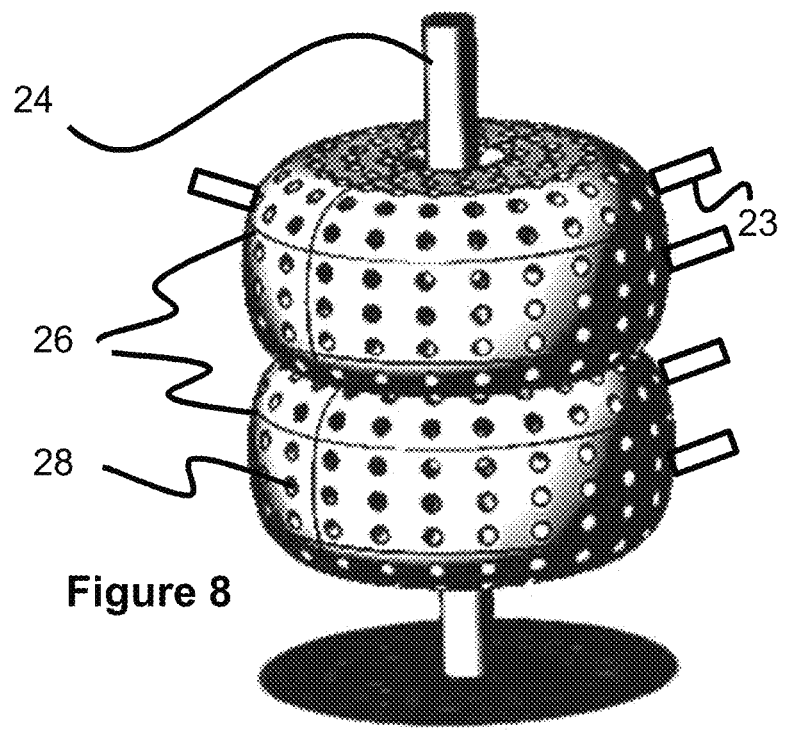
FIG. 8 illustrates an occlusive device comprising multiple disc-shaped portions and a mandrel for making the same.
Figure 9:
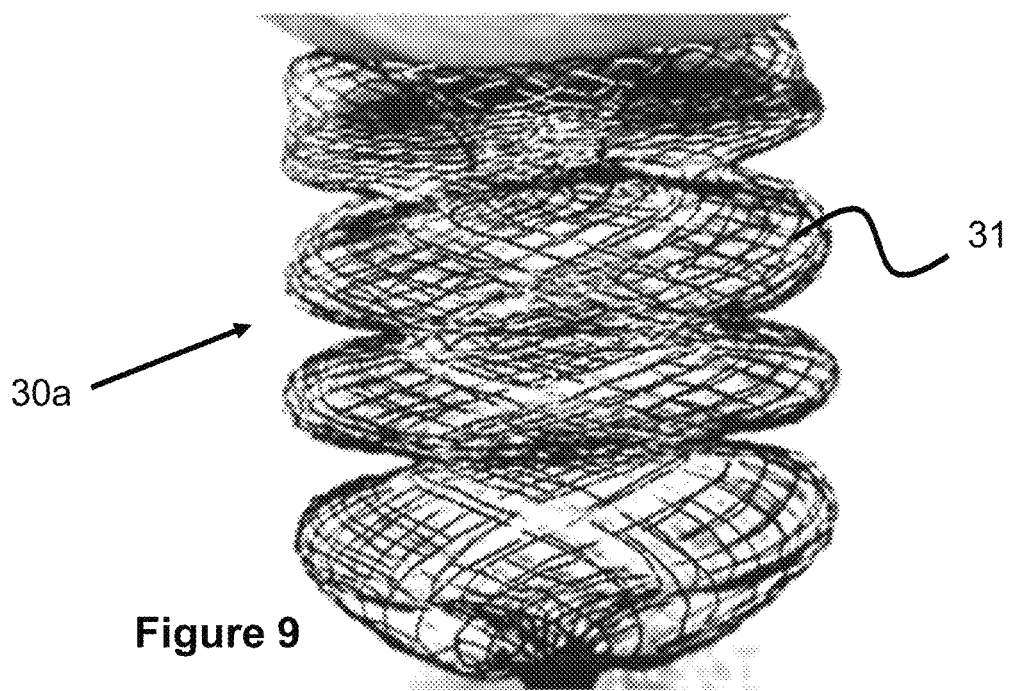
FIG. 9 illustrates an occlusive device comprising multiple disc-shaped portions and a mandrel for making the same.

FIGS. 8-12 relate to several embodiments of an occlusive device composed of a braid forming multiple disc shaped sections 31, such as the device 30a of FIG. 9 having four disc shapes. Though the term 'disc-shaped' is used, the shaped sections may take on a number of shapes including ellipsoid, ovular, cylindrical, conical, frusto-conical, etc. The purpose of such a shape is to allow for both compressibility and elongation of the occlusive device.

This shape is created via a plurality of winding mandrels 26 that have the shape of desired braided section 31. FIG. 8 illustrates one example of two disc-shaped mandrels 26 connected together by a post 24 extending there through. Each mandrel 26 includes a plurality of holes 28 that pins 23 can be inserted into to form a desired braiding pattern. A portion of the pin 23 sits outside the hole 29 and the braid can be wound around the various pins to create the occlusive device shape. Each mandrel 26 can have the same shape, each mandrel 26 can have a different shape, or a combination or similar/different shapes can be used for a plurality of mandrels 26.

Figure 10:
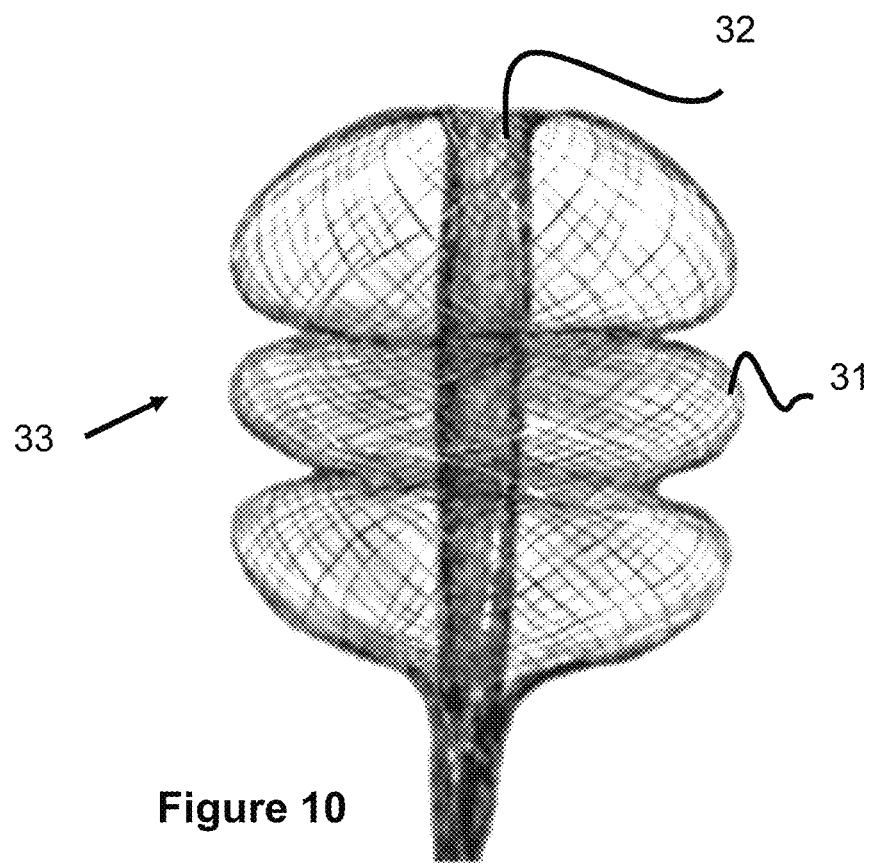
FIG. 10 illustrates an occlusive device comprising multiple disc-shaped portions and a mandrel for making the same.

FIG. 10 shows an occlusive device embodiment 33 similar to device 30a of FIG. 9, but with a center braid element 32. The shaped mandrels 26 of FIG. 8 include a center post 24. When the wires are wound through the top mandrel to create the top part of the occlusive device, the remaining wires can be pulled through the center element and through the bottom of the center post 24. Alternatively, if the center element 24 is a rod and has no lumen, the remaining wires are pulled around and not through the center element 24. Alternatively, the constituent wires are first pulled through/ around the center rod 24 and then the mandrel winding commences. Various winding techniques are possible. For example, if there are three disc shaped elements 31 used, as shown in FIG. 10, the process may start with winding around the middle mandrel 26, then the bottom mandrel 26, then pulling the wires up back over the mandrels, and the wires are then wound over the top mandrel 26—this would create a multiple-layered effect where the side walls would be doubled up over a portion of the mesh device since wires are pulled back over the device. FIGS. 9-12 show the occlusive device comprising 3-4 shaped sections 31, however, fewer or more shaped sections 31 can be used.

Figure 11:
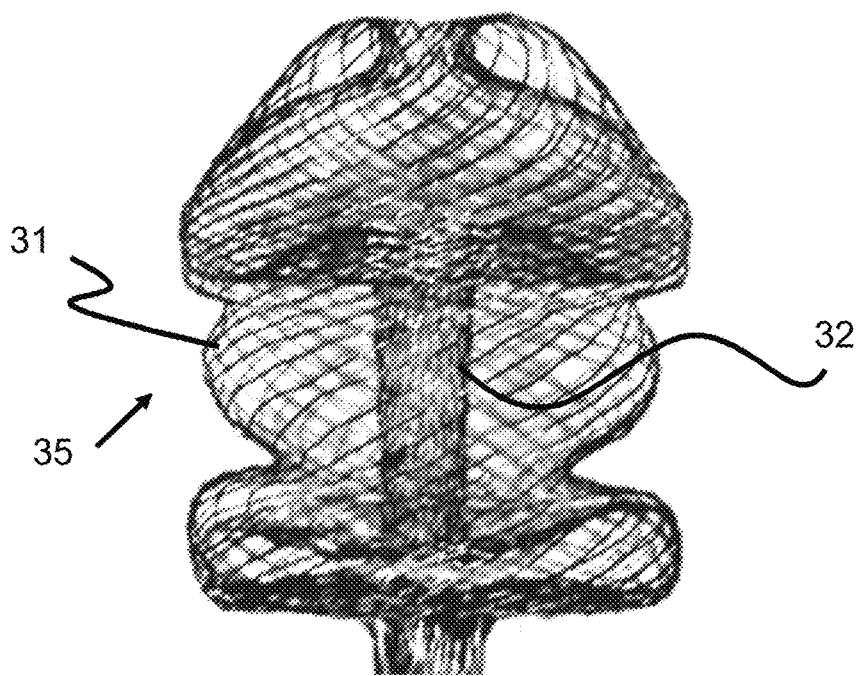
FIG. 11 illustrates an occlusive device comprising multiple disc-shaped portions and a mandrel for making the same.

Other occlusive device shapes may utilize the center element through only a portion, but not all, of the braid. Various occlusive shapes are possible, utilizing fewer or more disc shaped elements. FIG. 11 shows another occlusive device 35 shape utilizing various elements 31 of different shapes and a center element through only a portion of the occlusive device. In one example, the proximal ends of the wires may be welded or attached to the proximal ends of the center element 32 so that the proximal end of the occlusive device is integral.

Figure 12:
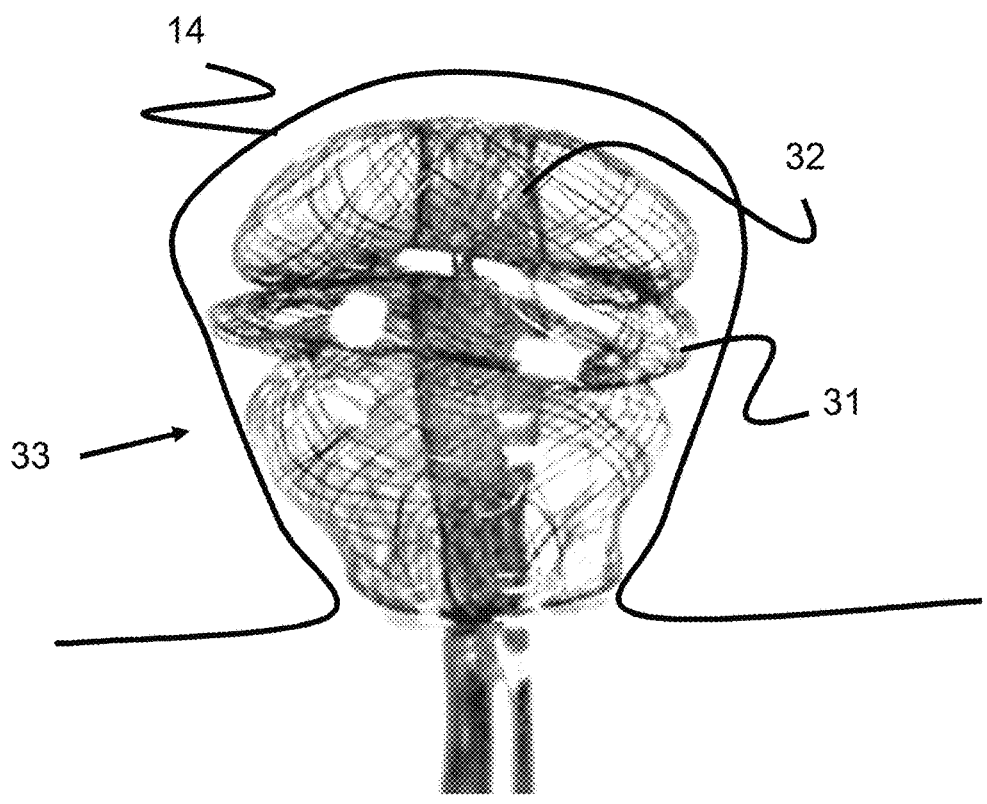
FIG. 12 illustrates an occlusive device comprising multiple disc-shaped portions and a mandrel for making the same.

FIG. 12 shows the device 33 of FIG. 10 within an aneurysm 14. As mentioned previously, one advantage of utilizing a mesh and having different disc-shaped elements is compressibility and elongation of the braid. The braid can elongate and lessen the radial dimension of the disc elements, or compress and expand radially by sacrificing longitudinal elongation.

In one embodiment, a winding method of winding an occlusive device of FIGS. 8-12 is described and shown in FIGS. 28A-28E. The winding method is useful to create a device similar to those shown in FIGS. 10-12, which utilize a center braid element 32 within the disc portions 31. The winding process utilizes two braiding mechanisms—an outer braider 84 and an inner braider 86. A first set of wires 80 is connected to outer braider 84 and these wires 80 are wound over the pins of the mandrel 26A. A second set of wires 82 is connected to the inner braider 86 and these wires are not braided over the pins but are instead pulled into the center channel of the mandrel (i.e. element 24 of FIG. 8). Wires 82 are then placed onto the outer braider 84.

A second mandrel 26B is placed next to the first mandrel 26A. The first set of wires 80 are pulled through the inner channel of the second mandrel 26b (similar to how wires 82 were initially pulled through the inner channel of the first mandrel 26a), while the second set of wires 82 are wound over the pins of the second mandrel. The first set of wires 80 are connected to the inner braider. As can be appreciated, whenever a set of wires is pulled through the inner channel of the mandrel, said wires are connected to the inner braider—while when the set of wires is wound over the pins of the mandrel, said wires are connected to the outer braider. The braiders have a number of carriers 86 and the carriers contain a number of bobbins to accommodate the wires, the braider can be automated so that the carriers rotate in various configurations while the mandrel moves longitudinally to enable the braiding to occur. Additional mandrels can also be placed and the wire arrangement would continue to alternate, so, for example, the first set of wires 80 would first form the outer braid around the first mandrel, then the inner braid in the second mandrel, then the outer braid of the third mandrel—while the second set of wires 82 would form the inner braid of the first mandrel, then the outer braid of the second mandrel, then the inner braid of the third mandrel, etc. Thus, the inner braid 32 of this winding method described can be thought of as discontinuous since different wire elements are forming different portions of the inner braid, while different wire elements also form different portions of the outer braid. The outer braid would need more carriers to hold the various wires since at some point all the wires (both wire sets 80, 82) will be held by the outer braider—while the inner braid would only hold either wire set 80, 82, or neither—thus the outer braider 84 would need at least twice as many carriers as inner braider 86. For example, if the braids for each section were comprised of 48 wires (i.e. each wire set 80 and 82 comprise 48 wires for a total of 96 wires used), the inner braider should have at least 48 carriers to accommodate one of the sets, while the outer braider should have at least 96 carriers to accommodate both sets of wires.

Figure 28A:
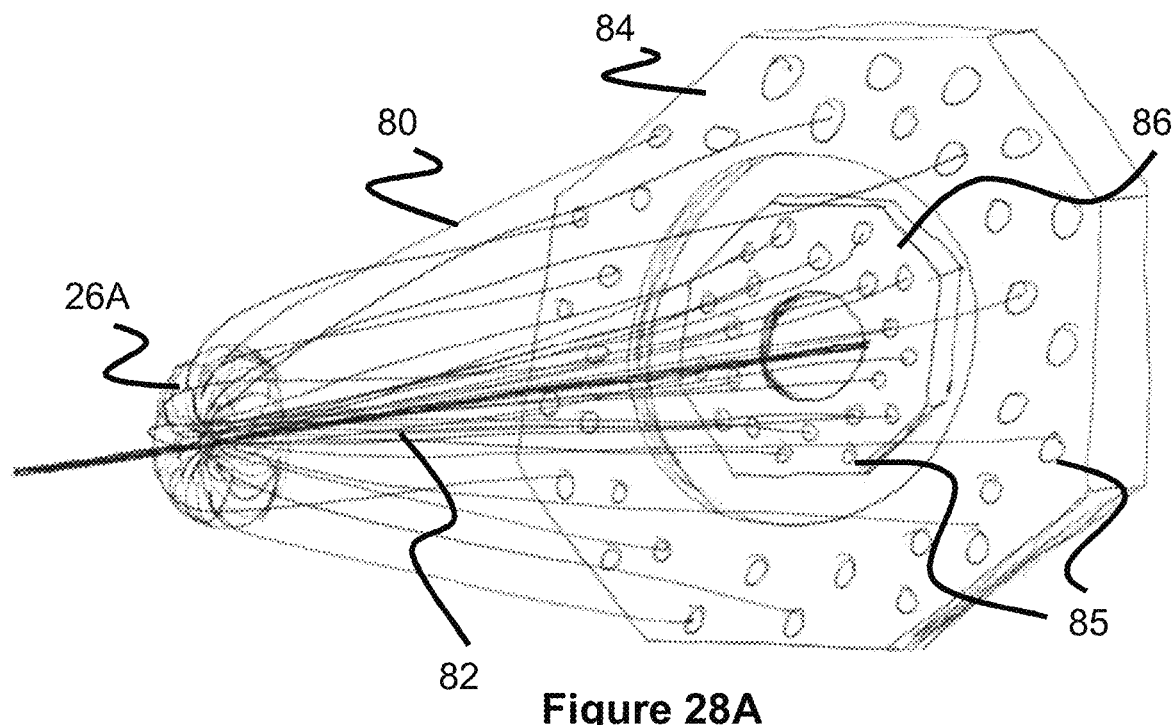
FIG. 28A illustrates a braider comprising an inner and an outer braider. The braider can be used to braid an occlusive device.
Figure 28B:
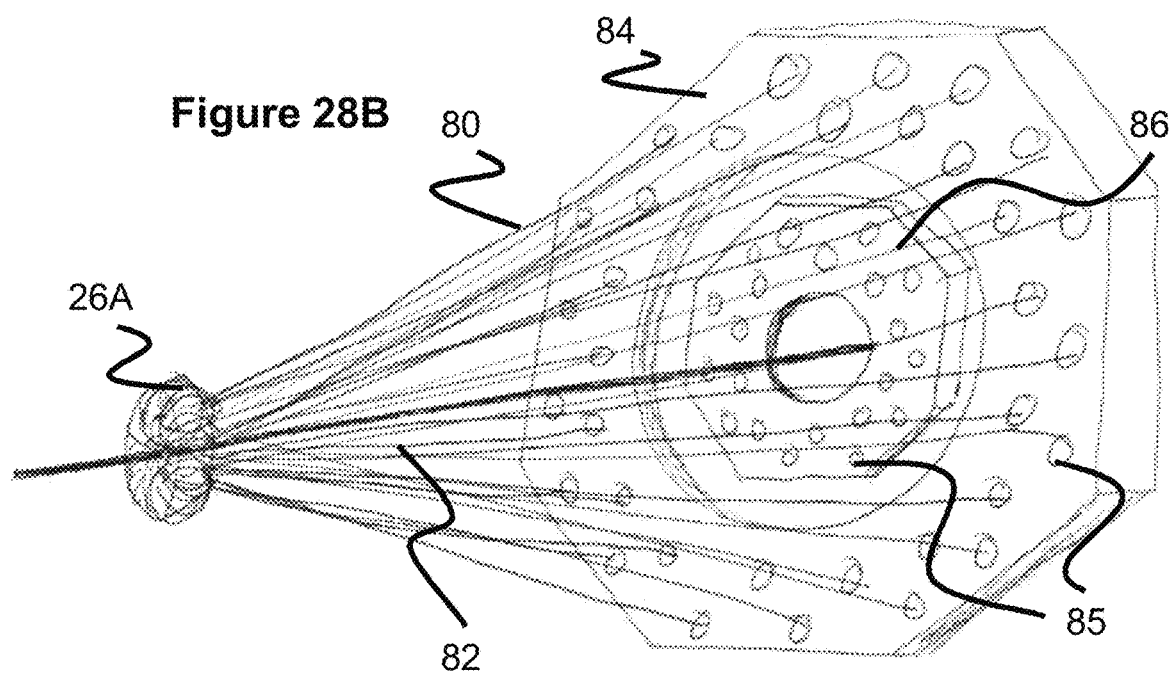
FIG. 28B illustrates a braider comprising an inner and an outer braider. The braider can be used to braid an occlusive device.
Figure 28C:
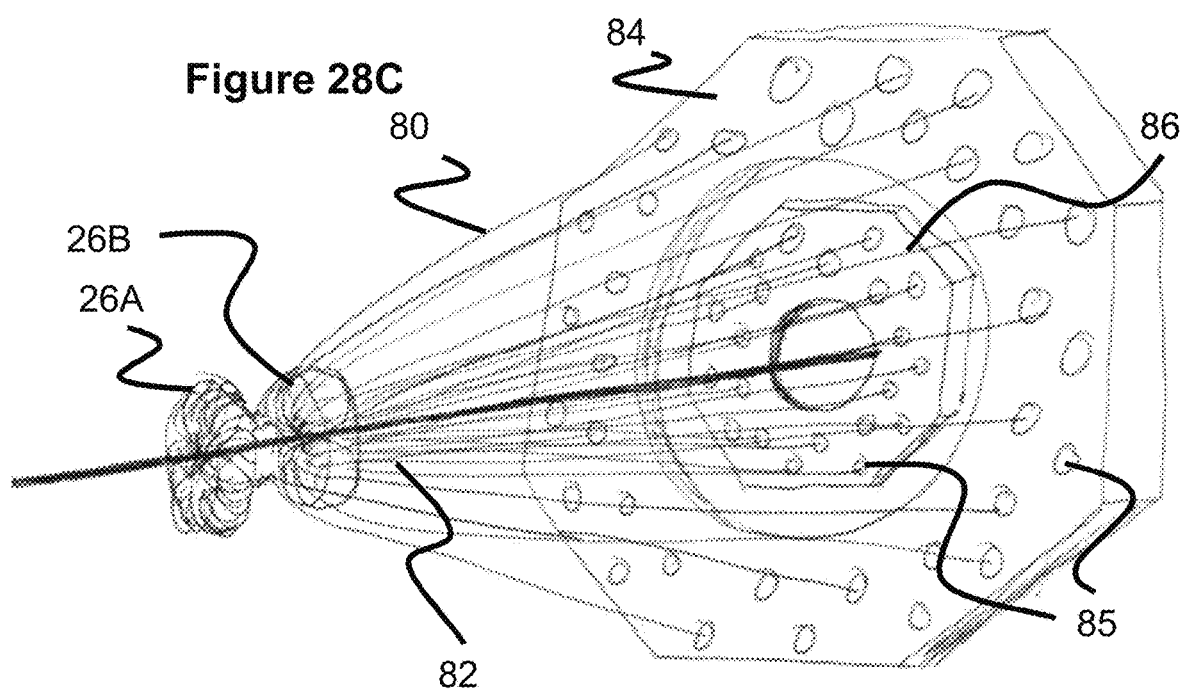
FIG. 28C illustrates a braider comprising an inner and an outer braider. The braider can be used to braid an occlusive device.

FIGS. 28A-28C show the various manufacturing steps just described. Different winding methods may also utilize a continuous inner element 32, for example second set of wires 82 would be pulled through the inner channel of a series of mandrels, while first set of wires 80 is wound around the periphery of the various mandrels. If an inner and outer braider were to be used with such a configuration, the second set of wires 82—which comprises the continuous inner element 32—would remain connected to the inner braider; meanwhile the first set of wires 80—which comprises the outer braided portion—would remain connected to the outer braider during the braiding operation.

Figure 29A:
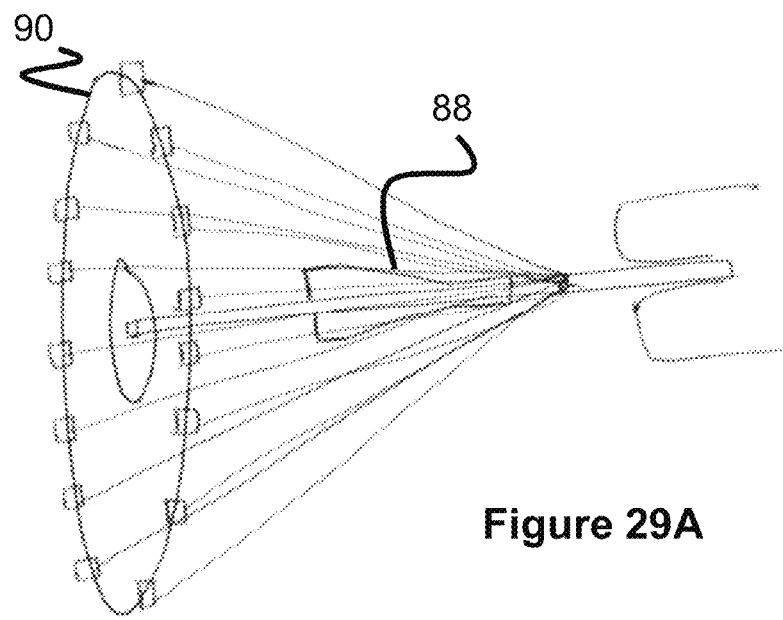
FIG. 29A illustrates a tapered mandrel used to create an occlusive device.
Figure 29B:
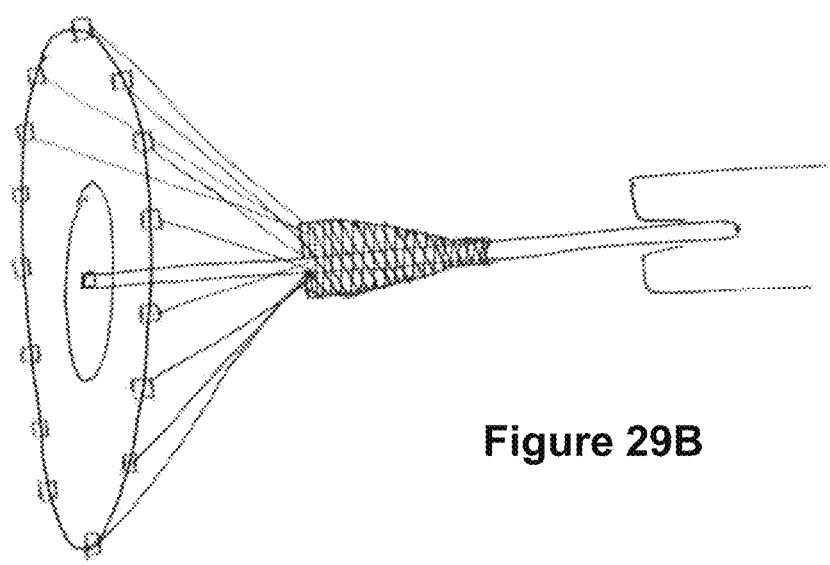
FIG. 29B illustrates a tapered mandrel used to create an occlusive device.
Figure 29C:
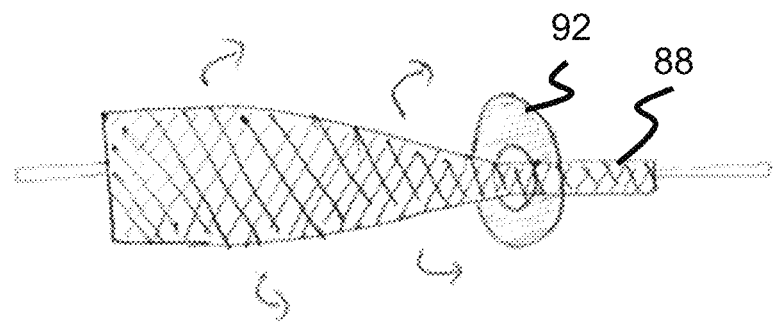
FIG. 29C illustrates a tapered mandrel used to create an occlusive device.
Figure 29D:
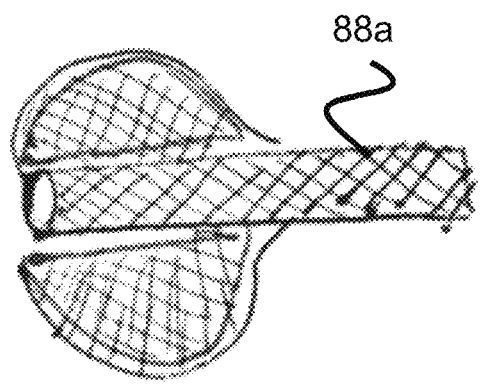
FIG. 29D illustrates a tapered mandrel used to create an occlusive device.
Figure 29E:
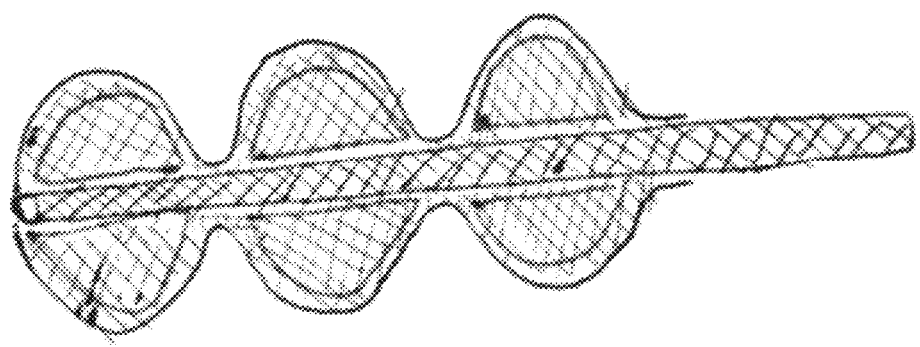
FIG. 29E illustrates a tapered mandrel used to create an occlusive device.

FIGS. 29A-29E show another method of creating a braid with multiple layers. A tapered mandrel 88 is braided by braider 90. The taper allows one end to have a smaller diameter, one end to have a larger diameter, and varying diameter in between the ends. It is desirable that a portion of the smaller diameter end 88a has a consistent diameter, as shown in FIG. 29C, for reasons that soon will become apparent. The tapered mandrel is braided. A circular element 92 can be placed in one or more locations along the smaller, consistent diameter portion 88a of the tapered mandrel. The rest of the braid is then folded back over the circular element, which creates the outer globular shapes, while portion 88a remains and comprises the inner braid portion. In FIG. 29E, three circular elements are placed along section 88a in order to create three enlarged sections. The folded sections can be tied and heat set to set the shape.

Figure 13A:
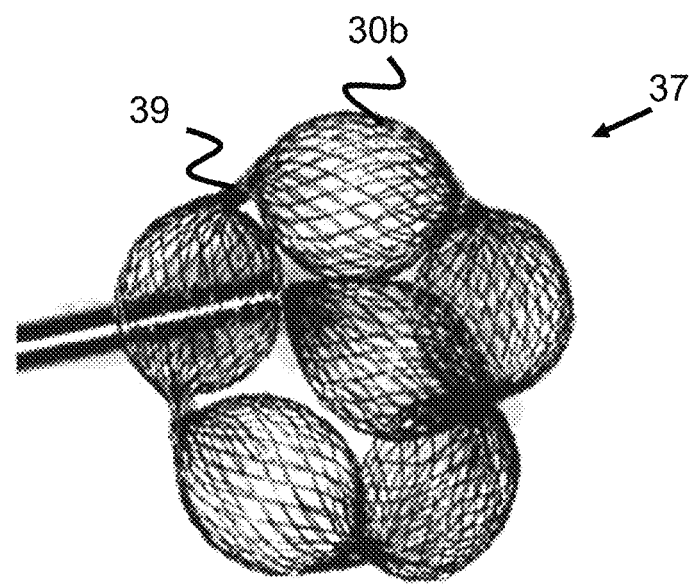
FIG. 13A illustrates an occlusive device, comprising smaller and larger diameter regions.
Figure 13B:
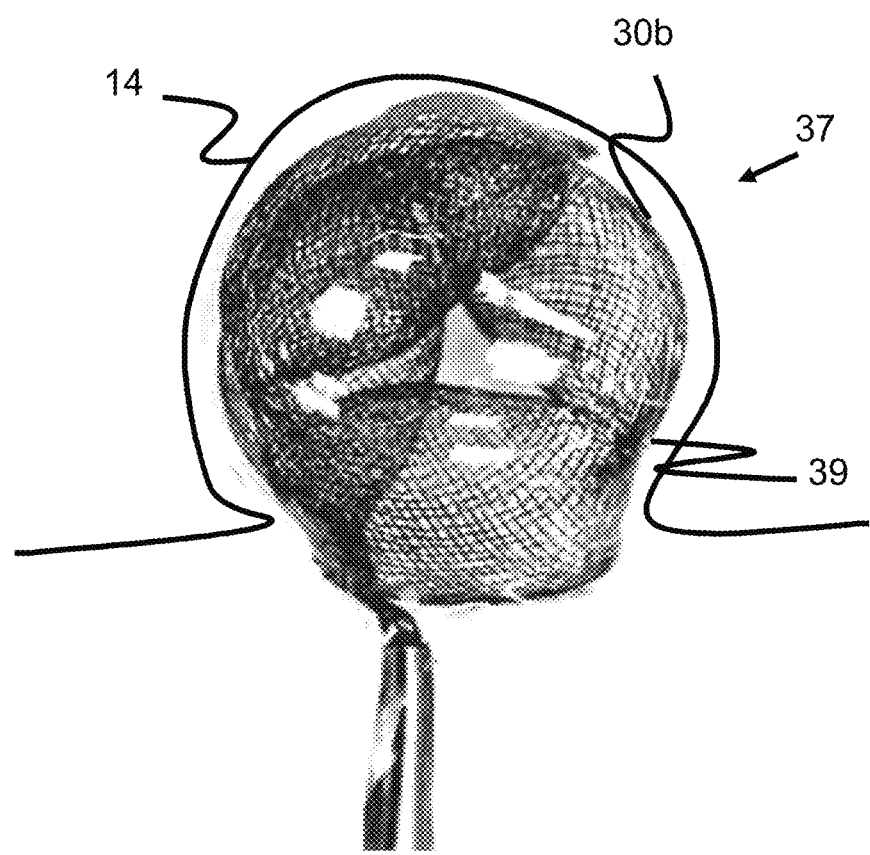
FIG. 13B illustrates an occlusive device, comprising smaller and larger diameter regions.

FIGS. 13A and 13B shows an occlusive device 37 comprising a tubular braid that is flattened into a dual layer and then heat shaped to create a series of smaller width mesh regions 39 and larger width regions 30b (i.e. a plurality of "petal" shapes 30b). These petal shapes 30b can be heat set a second time to impart a curve shape that roughly matches the curve within an aneurysm.

Figure 14:
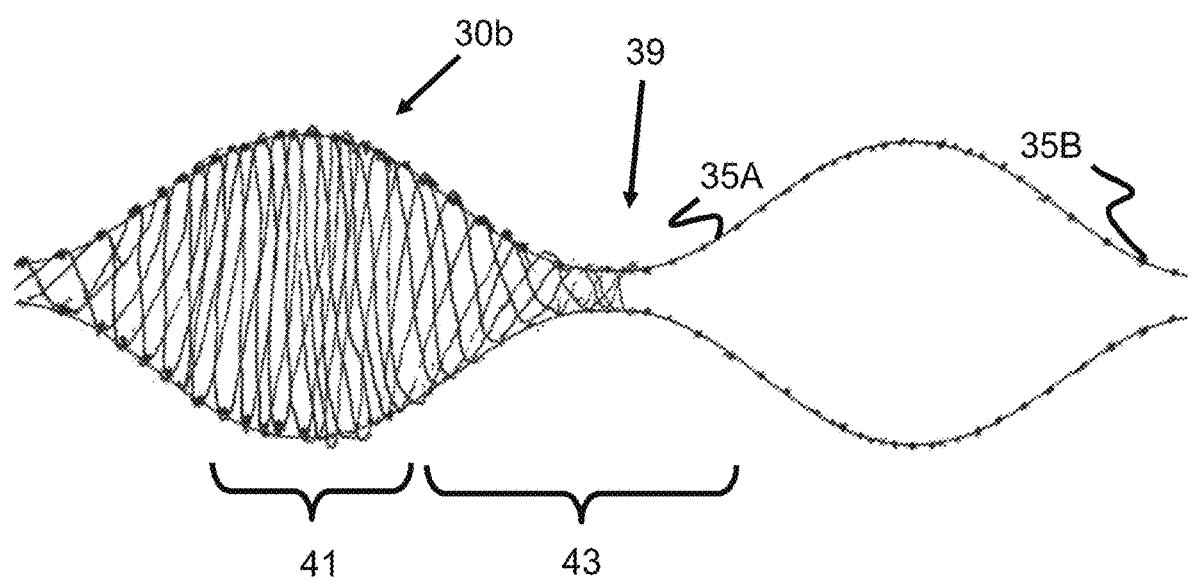
FIG. 14 illustrates an occlusive device, comprising smaller and larger diameter regions.

If the starting tubular braid was woven with a uniform braid pattern, the braid density would be the greatest in the smaller width regions 39 and least dense in the middle of each petal 30b. However, since the middle of the petal 30b is the location in which the device 37 attempts to create the largest flow disruption within the aneurysm, such braid density may not optimally disrupt flow as intended. FIG. 14 illustrates a braid technique and pattern that varies both the pitch and width of the braid to provide an increased braid density area 41 in the middle of the petal 30b and a decreased braid density area 43 between the center of the petals 30b. This variable pitch/widths technique allows the braid density to be optimized for the greatest flow disruption at the larger widths of the petal where it is needed most.

A braid fixture 35A can be used to create the variable pitch/width of the braid. The fixture 35A is a bulb structure that regularly increases and decreases in diameter, forming a repeating, three-dimensional wave pattern. The fixture 35A also includes a plurality of mounting locations for pins 35B that are located at regular intervals around the fixture 35A that allow one or more wires to be braided around the fixture 35A. The longitudinal distance between each pin 35B is smallest at the peak of each of the "waves" in area 41 and gradually increases as the trough of the wave is reached in area 43, after which, the spacing increases again as it approaches the wave peak. In this regard, the pore size of the braid pattern is the smallest at the peak of each "wave" and the largest at the trough of a "wave".

Figure 15:
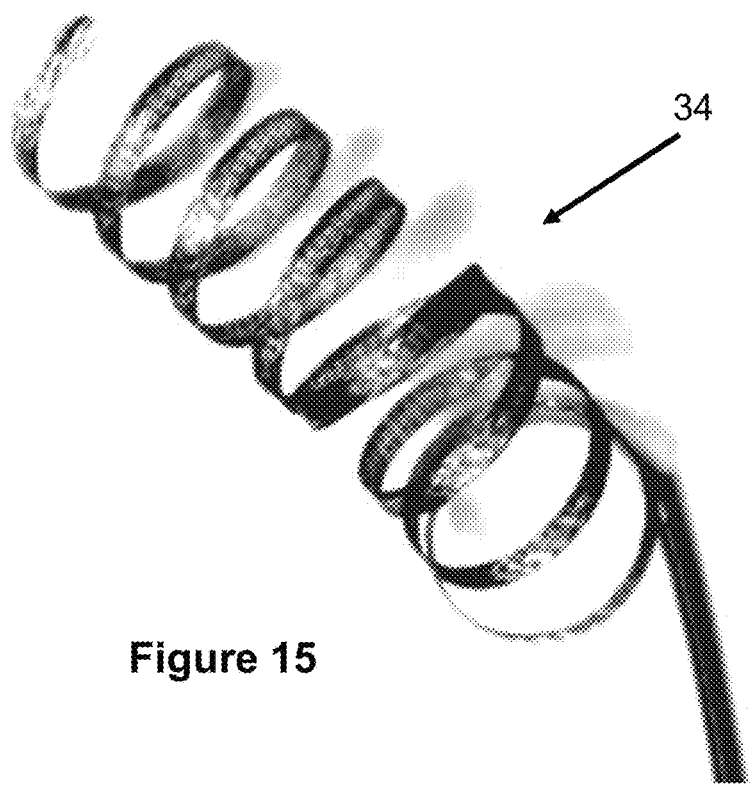
FIG. 15 illustrates an occlusive device comprising a spiral ribbon.

FIG. 15 shows an occlusive device 34 comprising a spiral ribbon mesh. The spiral ribbon may either have a uniform or variable diameter/thickness. The holding element 12 of FIG. 1, and occlusive devices of FIGS. 9-15 utilize a mesh or braid of wires. The wires can be made of nitinol, cobalt-chromium, polymer, stainless steel, and/or spring-tempered stainless steel. Radiopaque material such as tantalum, platinum, gold, and/or palladium may also be used instead, or may be incorporated into the mesh along with the non-radiopaque materials listed in the previous sentence. In one example, the mesh may solely comprise nitinol wires, in another example it may comprise a mesh of nitinol wires along with another radiopaque wire (such as the materials described above) comprising the mesh. In another example, wires comprising a radiopaque core and nitinol exterior or a nitinol core and a radiopaque exterior may be used. In one example, the wire diameters can be about 0.002" to about 0.005". Some or all of the wires comprising the braid/mesh can also include a radiopaque (i.e. tantalum) coil to aid in visualization.

The device 11 of FIG. 1 may utilize a detachable tip-type system, as discussed earlier, since the occlusive device of said figure would be attached to the distal tip of a microcatheter 9 which is delivered through a larger catheter 8. Another embodiment may utilize a solid-lumen pusher instead. This is possible where the device would be delivered as is, and the microcatheter lumen would not be needed to introduce subsequent embolic agents. Thus, for example, the occlusive device 11 of FIG. 1 may be connected to a pusher rod, which is pushed through a delivery catheter or a microcatheter, which is placed within an aneurysm, the device is subsequently pushed out or the catheter is retracted to expose the device. A thermal, mechanical, or electrolytic detachment system may be used to detach the center element 16 of the device from the pusher rod. Various detachment systems are discussed in U.S. Pat. Nos. 5,895,385, 5,108,407, 6,500,149, 4,346,712, 8,182,506, US20100268204, US20110301686, US20150289879, all of which are hereby incorporated by reference in their entirety. The pusher rod and catheter are subsequently retracted. Alternatively, the catheter lumen is subsequently used to introduce other embolic agents (such as coils or liquid embolic) proximal to the now-deployed occlusive device. Thus the occlusive device would form a distal barrier to cushion the dome of the aneurysm, and the additional embolic agents would fill the more proximal section of the aneurysm.

In one embodiment utilizing the device of FIG. 1 but with the device being connected to a pusher rod instead of a microcatheter, a first catheter can be used to deploy the occlusive device. A smaller catheter used specifically for embolic agents can then be deployed within the catheter and can be deployed through the occlusive device to introduce additional embolic agents (i.e. embolic coils or liquid embolic). The occlusive device can then be detached. Alternatively, the occlusive device can be placed and detached. The catheter, initially used to deliver the occlusive device, can then be used to deliver additional embolic agents (i.e. coils or liquid embolic). In either case (either where a separate catheter, or alternatively where the same occlusive device catheter is reused), the catheter can be navigated to another place where the catheter sits within the braid to deliver the additional embolic agents. In one example, the catheter can be placed toward the top of the occlusive device near the dome of the aneurysm, so the aneurysm and occlusive device would be filled from a top-down perspective. In another example, the catheter can be placed toward the bottom of the occlusive device and the aneurysm and occlusive device would be filled from a bottom-up perspective.

The device of the disc-shaped elements of FIGS. 8-12, or the smaller/larger diameter regions of FIGS. 13-14, or the spiral ribbon shape of FIG. 15 would be connected to a pusher element. Various thermal, mechanical, or electrolytic detachment systems may be used to sever the device from the pusher element, including the detachment systems contemplated in the earlier incorporated by reference applications. Similarly, the catheter used to deliver the occlusive device may subsequently be used to deliver additional embolic agents such as embolic coils or liquid embolic.

FIGS. 16-22 show a pusher detachment system 45 located near a distal end of an elongated pusher device 47. The pusher 47 is advanced through a catheter 8 and its detachment system 47 is actuated to detach an occlusive device 48, such as those devices 48 described in this specification. The occlusive device 48 is secured to the pusher via a axially-movable release wire 38 on the pusher that is, initially, positioned into a cavity of a coupling fixture 40 on a proximal end of the device 48, preventing the device 48 from moving sideways off of the distal end of the pusher 47. The device 48 is prevented from moving off of the release wire 38 by a tether that is connected to the coupling fixture 40 and to a more proximal portion of the release wire 38 that is exposed from a cut-away region 44 on a distal region of the pusher body 36. To aid in flexibility and enhance the connectivity between the pusher body 36 and the coupling fixture 40, a spring 42 is located between the two.

To actuate the detachment system 45, the release wire 38 is proximally retracted such that a distal end of the wire 38 moves proximally into the cut-away region 44 and beyond the proximal point of attachment of the tether 46. The tether is connected to the release wire 38 such that it slides relative to the release wire 38 (e.g., by being tied in a loose knot or via a looped fixture). Hence, the release wire 38 not only moves out of the coupling fixture 40, but also retracts to allow the tether 46 to slide completely off with wire 38, leaving the occlusive device 48 completely disconnected from the pusher 47. Further, since the spring 42 abuts the coupling fixture 40, it may provide some force or kick to distance the occlusive device 48 from the pusher 47.

Figure 17:
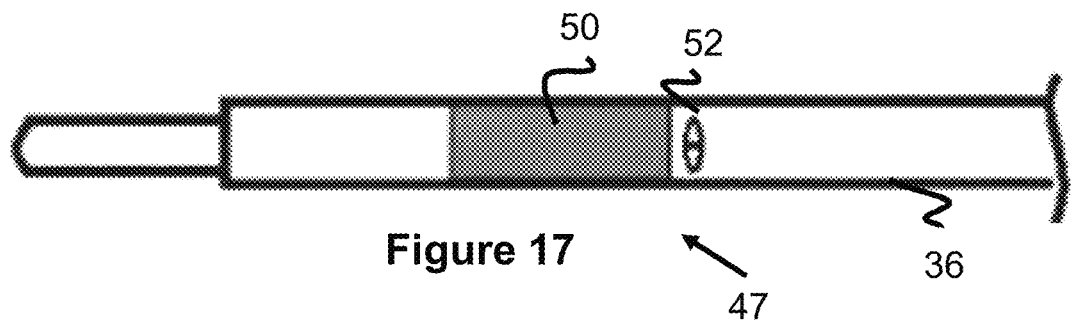
FIG. 17 illustrates a detachment system for an implant, where the implant can be an occlusive device.

FIGS. 17-20 show one possible mechanism to retract the release wire 38 of the pusher 47 by breaking a proximal end of the pusher body 36 to expose a proximal portion of the wire 38, thereby allowing the physician to proximally pull on the wire 38 and actuate the detachment system 45. As seen in FIG. 17, the proximal end of the pusher body 36 preferably includes a weakened area 52 (e.g., one or more holes in the pusher body 36) and a visual guide 50 that indicates to a user where a breakage tool 54 should be aligned to assist in breaking the pusher body 36. Preferably, the weakened area 52 of the pusher body 36 is strong enough that it will generally not break during a procedure without the added leverage of the tool 54, preventing complications from an unintended release of the occlusive device 48.

Figure 18:
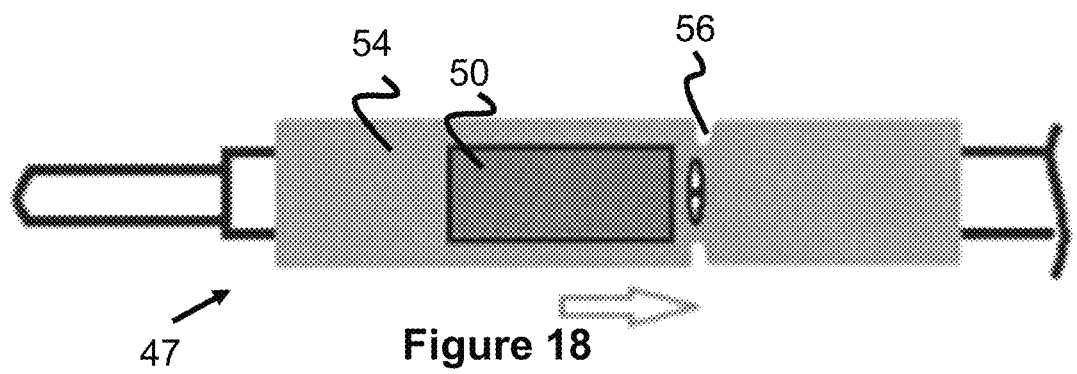
FIG. 18 illustrates a detachment system for an implant, where the implant can be an occlusive device.
Figure 19:
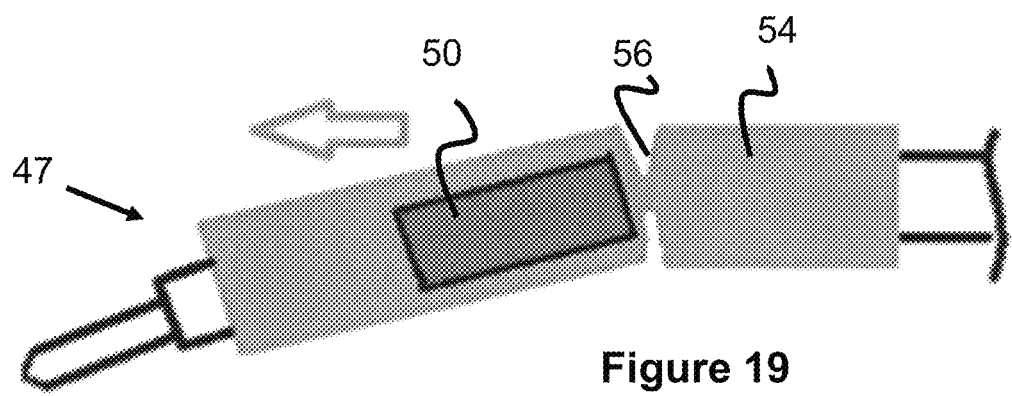
FIG. 19 illustrates a detachment system for an implant, where the implant can be an occlusive device.
Figure 20:
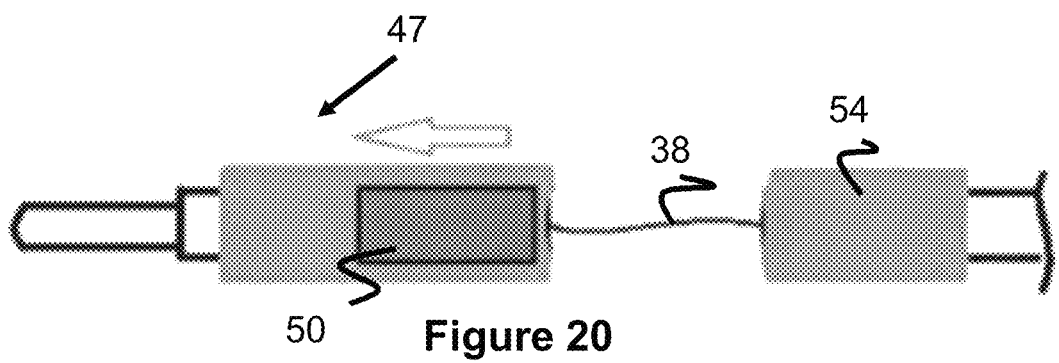
FIG. 20 illustrates a detachment system for an implant, where the implant can be an occlusive device.

The breakage tool 54 preferably has a passage closely sized to the diameter of the proximal end of the pusher body 36, allowing the tool 54 to slide over the body 36. The tool 54 preferably includes a narrow region 56 having a smaller diameter that aligns with the weakened area 52, allowing the physician to apply additional force to the weakened area 52, breaking both the pusher body 36 and the tool 54 itself, as seen in FIGS. 19 and 20. To aid the physician in properly aligning the narrow region 56, the pusher body 36 preferably includes a window to allow the user to see and align with the visual guide 50, as seen in FIG. 18. Alternately, the guide may be configured such that the tool 54 should be moved immediately adjacent of it or may be configured as a tactile detent, eliminating the need for the window.

Figure 16:
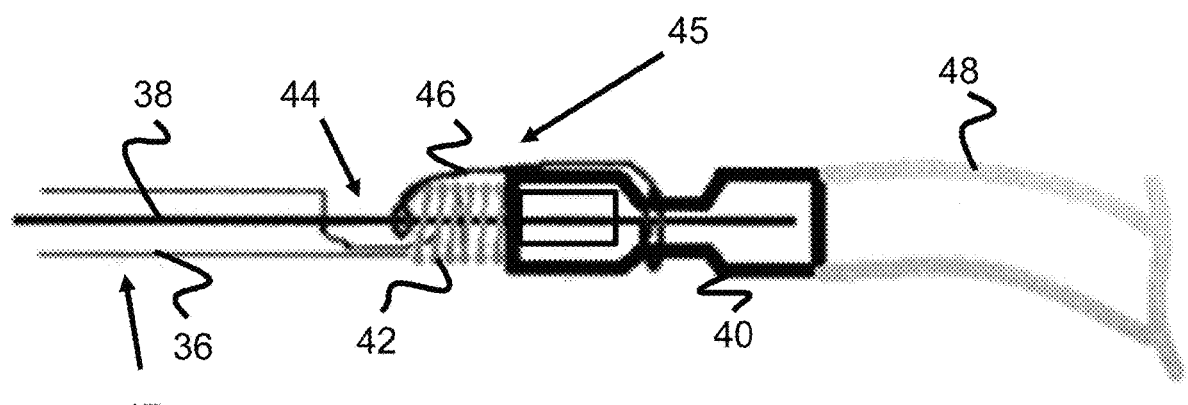
FIG. 16 illustrates a detachment system for an implant, where the implant can be an occlusive device.
Figure 21:
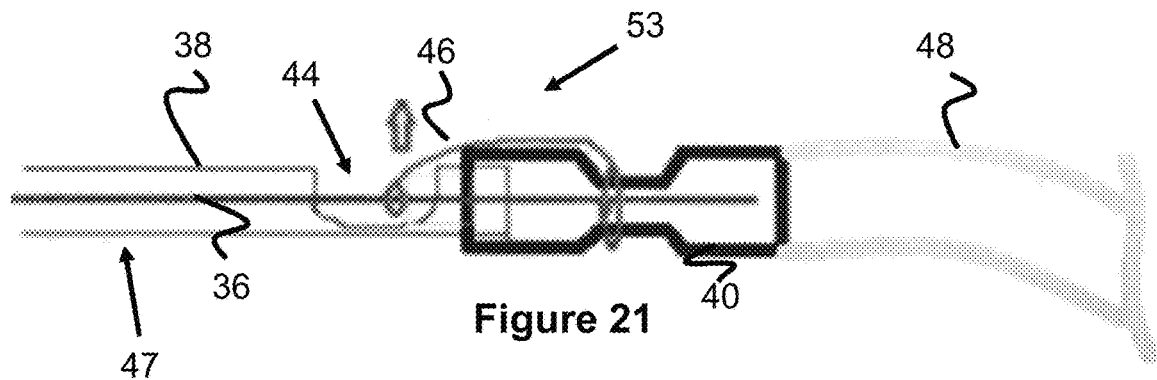
FIG. 21 illustrates a detachment system for an implant, where the implant can be an occlusive device.
Figure 22:
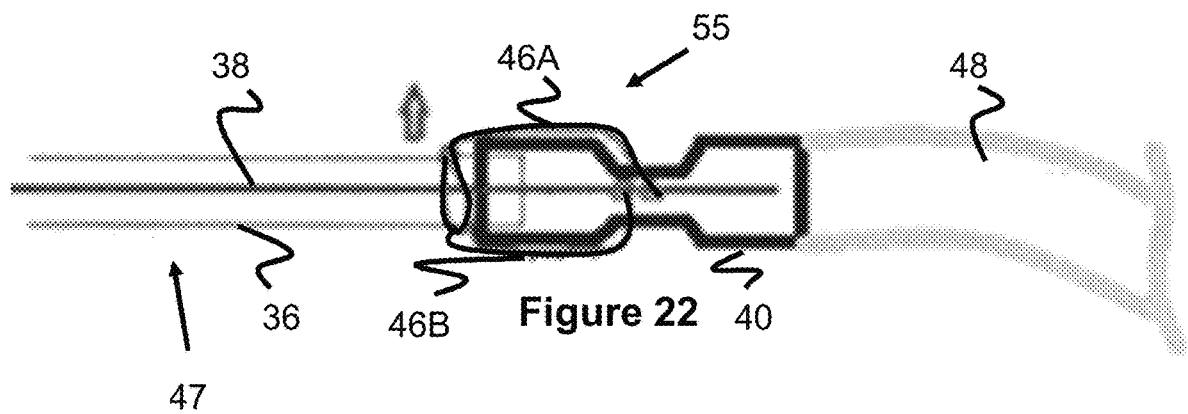
FIG. 22 illustrates a detachment system for an implant, where the implant can be an occlusive device.

FIGS. 21-22 show some alternative embodiments to the detachment system 45 of FIG. 16. FIG. 21 illustrates a detachment system 53 that is similar to that of the system 45, but does not utilize a spring 42 to provide the extra kick to push the coupler 40. FIG. 22 utilizes two window cut outs on the coupling fixture 40 and two tethers 46A and 46B. One tether 46A is attached to a distal part of the release wire 38 and then has a loop around a distal part of the pusher body 36. Another tether connects to another distal section of the release wire 38 and connects to a section of the loop around the distal part of the pusher body 36. In both systems, the knot around the release wire 36 is loose, such that pulling the release wire will release the coupling fixture 40 and the implant 48.

The occlusive device embodiments of FIGS. 8-12 and 13-15 may also be configured to act similar to the embodiment of FIG. 1. That is, the occlusive device may be pre-loaded at the distal part of a microcatheter which is delivered through a larger catheter. The proximal end of the occlusive device, in another embodiment, utilizes an element akin to center element 16 of FIG. 1. The center element would bind the constituent braid wires together. The center element would sit near the distal end of the microcatheter, and a detachment tip system similar to the detachable tip systems referenced earlier would be utilized in the system. Similar to the embodiment of FIG. 1, the user would position the device at the neck of the aneurysm and may optionally deliver embolic agents through the microcatheter (i.e. embolic coils or liquid embolic) through the occlusive device. Once the agents were delivered, the user would sever the tip of the microcatheter via the earlier contemplated detachment concepts, and retract the microcatheter.

Intrasaccular braided devices tend to work very well in bifurcation aneurysms in which the delivery catheter can pass relatively straight into the aneurysm. However, in other aneurysms such as sidewall aneurysms, the delivery catheter position becomes more perpendicular to the entrance of the neck of the aneurysm, making the deployment of braided intrasaccular type device more difficult. When deploying an intrasaccular device at an angle, the relatively stiff nature of the device and the pusher it is attached to may cause the catheter to straighten and the device to deploy at an angle within the aneurysm.

Figure 23A:
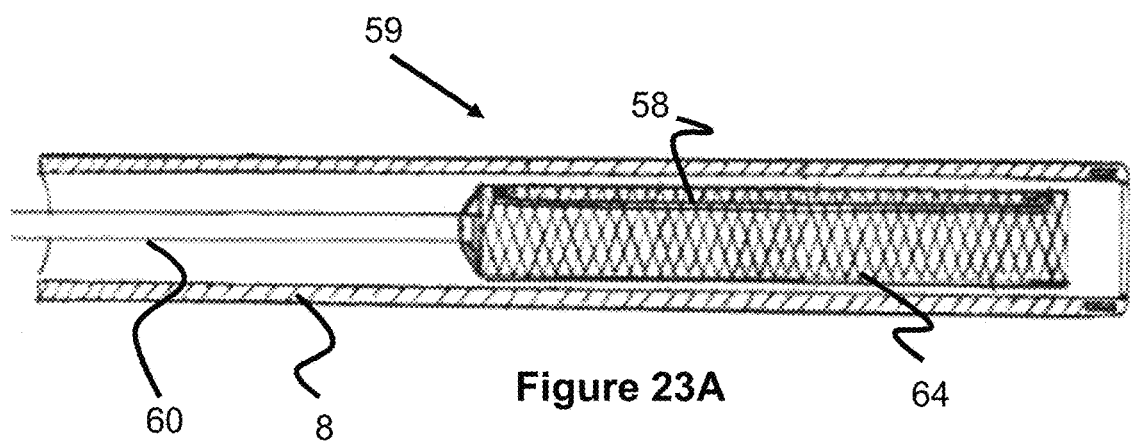
FIG. 23A illustrates an occlusive device having a tensioning member that allows the device to expand in a curved configuration.
Figure 23B:
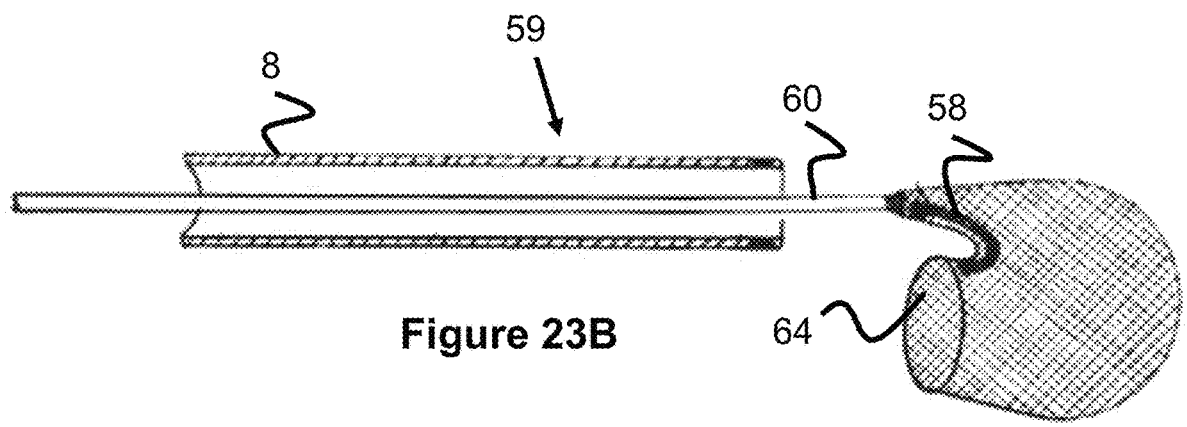
FIG. 23B illustrates an occlusive device having a tensioning member that allows the device to expand in a curved configuration.

FIGS. 23A-23B show a tensioning system 59 that allows an occlusive device 64 to expand in an offset or curved configuration, and thereby avoiding the above-mentioned complications. Specifically, the tensioning system 59 includes a tether 58 connected at a distal end and proximal end of a braided occlusion device 64. As the pusher 60 pushes the occlusive device out of the catheter 8, the material of the tether 58 is such that it causes the occlusive device 64 to maintain tension on one side of the device 64 during its expansion and allow full expansion on the opposite side. This results in the device 64 curving or bending in the direction of the tether 58 during expansion.

A more controlled, bent delivery maximizes the chance that the occlusive device 64 adopts its expanded shape to fill the aneurysm when a catheter is unable to access an aneurysm in a relatively straight trajectory. The tensioning member keeps tension on connected parts of the occlusive device, limiting expansion along one side of the device 64 and creating a curved shape. Additionally, an advantage of this technique is that a tether 58 can be applied to a wide range of braiding patterns of an occlusive device 64, such as a 1-over-1 pattern, a 2-over-1 pattern, and a 2-over-2 pattern.

The tether 58 may be an elastic polymer, stretched nitinol or stainless steel spring coil, nitinol or stainless steel wire, a shape memory wire or ribbon, platinum or tantalum wire or strips. Furthermore, more than one tether may be used, that is the tethers may be connected in a longitudinal series or may be offset along the vertical dimension of the implant. In one embodiment, the tether is a nitinol coil or wire and a heat source is connected to the tether in order to change the stiffness properties of the tether.

Figure 24A:
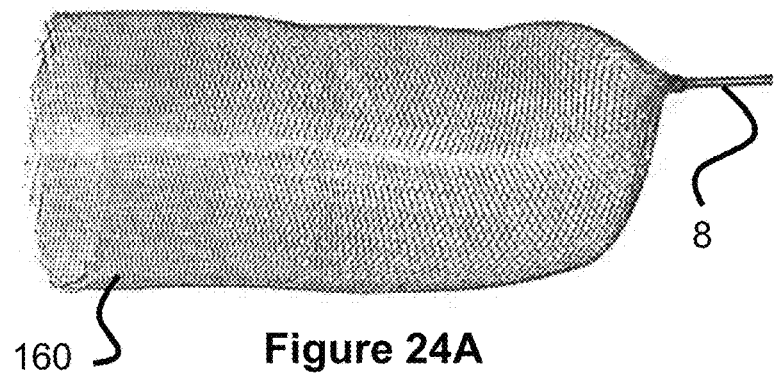
FIG. 24A illustrates an occlusive device that expands in an offset configuration from its catheter.
Figure 24B:
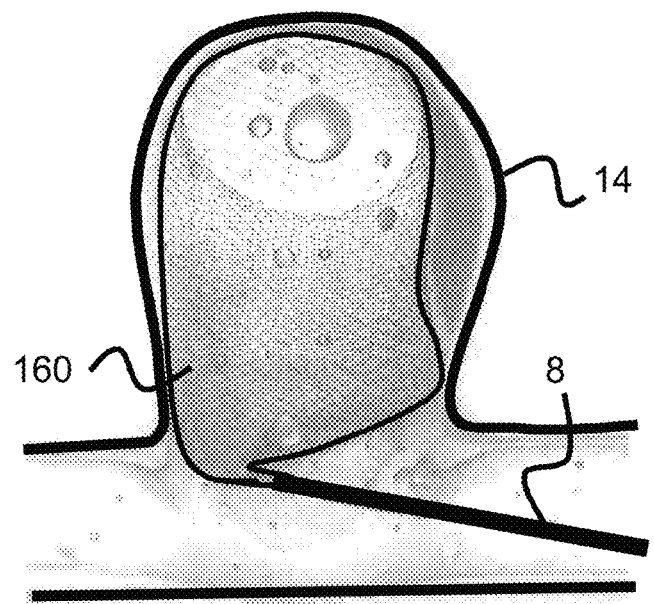
FIG. 24B illustrates an occlusive device that expands in an offset configuration from its catheter.

FIGS. 24A and 24B illustrate a braided mesh occlusive device 160 that is braided such that its expanded mesh shape expands in an offset manner relative the catheter 8 (or pusher), thereby more optimally expanding into an aneurysm when approached by the catheter 8 at an angle, as seen in FIG. 24B. In other words, when the device 160 is expanded, its center axis is offset from the center axis of the catheter 8 that it expands from.

Figure 24C:
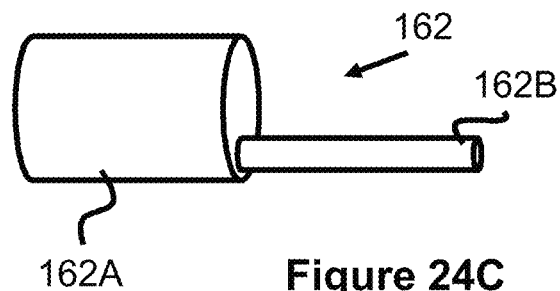
FIG. 24C illustrates a mandrel for creating the occlusive device of FIGS. 24A and 24B.

Such an offset-expanding occlusive device 160 can be created by placing a braided mesh tube or enclosed structure on a mandrel 162 (FIG. 24C) that has a relatively larger diameter cylindrical structure 162A and a relatively smaller diameter cylindrical structure 162B. The smaller diameter cylindrical structure 162B is fixed at a location that is offset for the central axis of the larger diameter cylindrical structure 162A, thereby imparting the offset shape of the occlusive device 160 after being heat-set. Preferably, the braided mesh tube is braided to form a uniform cylinder or tube initially, and then heat set to its offset shape. This technique allows the size of the braid cells in the final occlusive device 160 to be more consistent. Additionally, an advantage of this technique is that this offset heat set shape can be applied to a wide range of braiding patterns of an occlusive device 160, such as a 1-over-1 pattern, a 2-over-1 pattern, and a 2-over-2 pattern.

Additionally, the mandrel 162 can include a recess machined into the end of the larger diameter cylindrical structure 162A around the interface of the smaller diameter cylindrical structure 162B, allowing a cylinder to be passed over the smaller diameter cylindrical structure 162B to impart a dimple or depressed area around the proximal end of the occlusive device 162. This process is discussed in more detail with regard to FIGS. 25A-25D.

The braided intrasaccular occlusive devices described in this specification may be terminated at their proximal end and optionally at their distal ends via a marker band or other welding techniques, as described elsewhere in this specification. However, it is generally undesirable for the area of termination to protrude beyond the proximal or distal braided end surface of the occlusive device. For example, protrusion of the proximal end's termination point may extend into the parent artery and may cause unwanted thrombus formation. Additionally, protrusion of the distal end's termination point may cause the dome of the aneurysm to rupture.

Figure 25A:
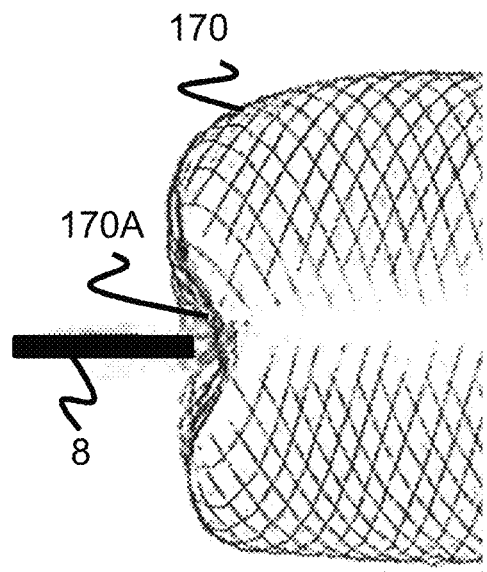
FIG. 25A illustrates a braided occlusive device with recessed end termination points and a mandrel for making the same.
Figure 25B:
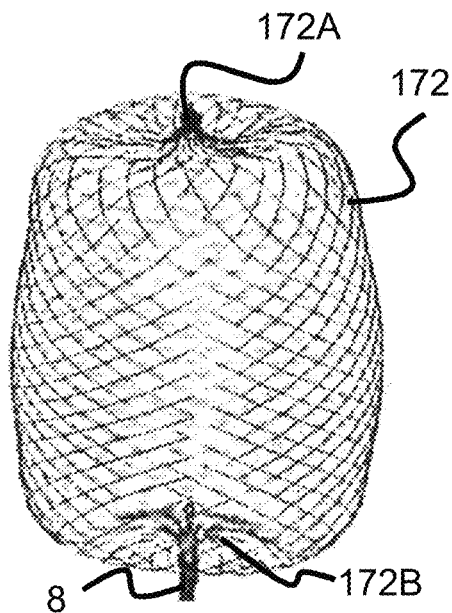
FIG. 25B illustrates a braided occlusive device with recessed end termination points and a mandrel for making the same.

FIGS. 25A-25D mitigate the above-mentioned complications by reducing the outward protrusion of the braid termination points when in an expanded configuration. Specifically, FIG. 25A illustrates a distally open ended occlusive device 170 that has a proximal braid termination point 170A that is inwardly recessed when expanded. Similarly, FIG. 25B illustrates an enclosed occlusive device 172 having a distal braid termination point 172A and a proximal braid termination point 172B, both of which are inwardly recessed when expanded.

Figure 25C:
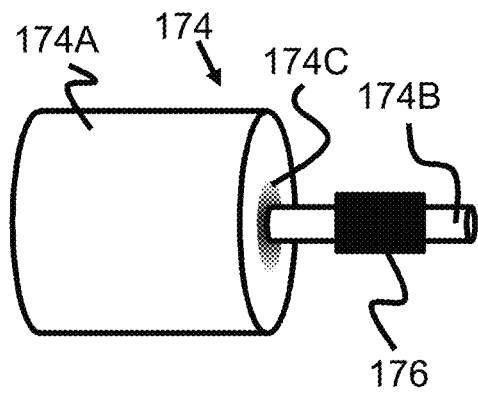
FIG. 25C illustrates a braided occlusive device with recessed end termination points and a mandrel for making the same.
Figure 25D:
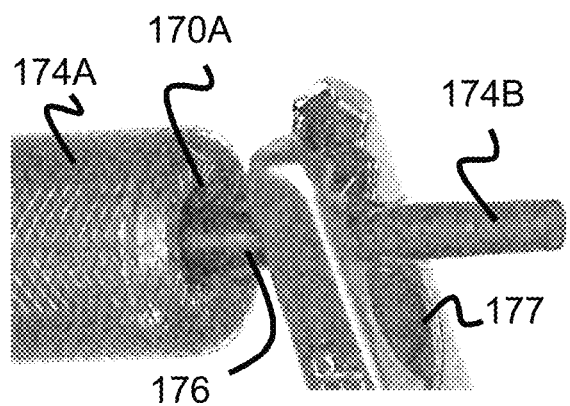
FIG. 25D illustrates a braided occlusive device with recessed end termination points and a mandrel for making the same.
Figure 26A:
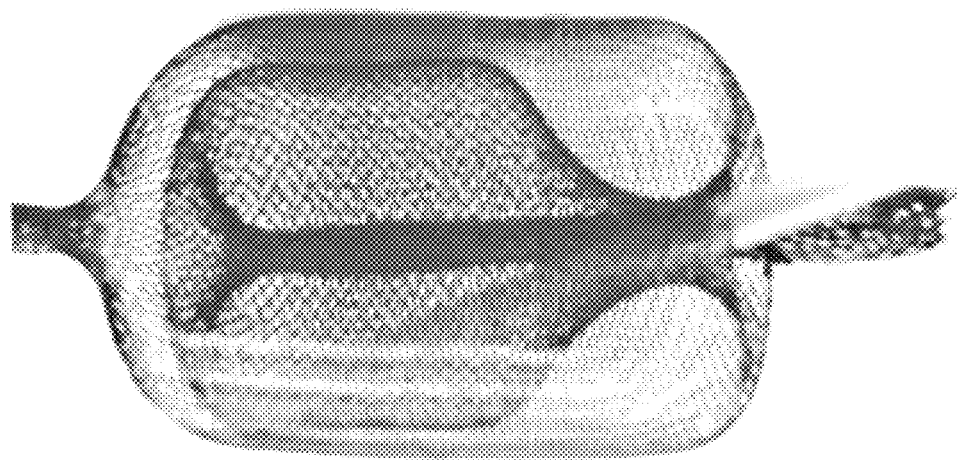
FIG. 26A illustrates an occlusive device comprising an outer and inner section.
Figure 26B:
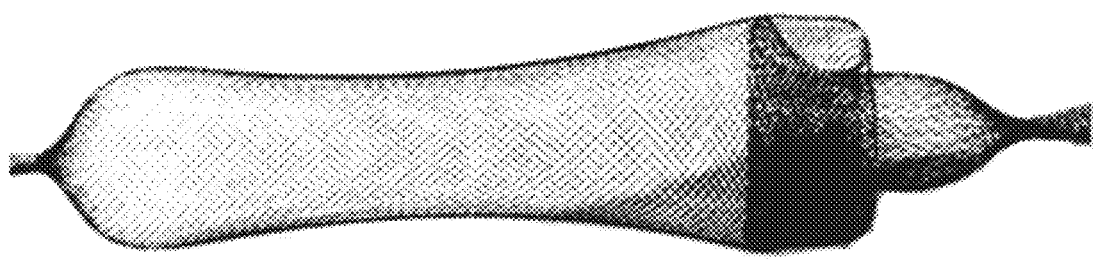
FIG. 26B illustrates an occlusive device comprising an outer and inner section.
Figure 26C:
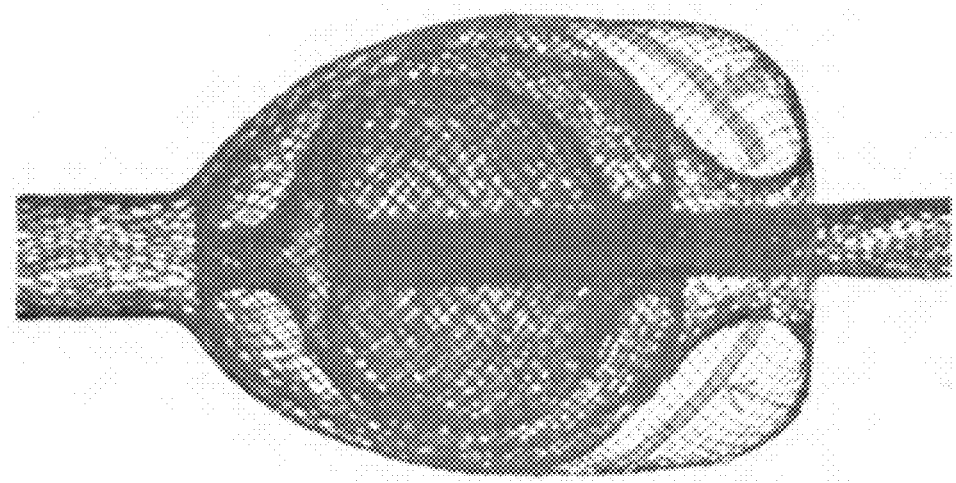
FIG. 26C illustrates an occlusive device comprising an outer and inner section.
Figure 26D:
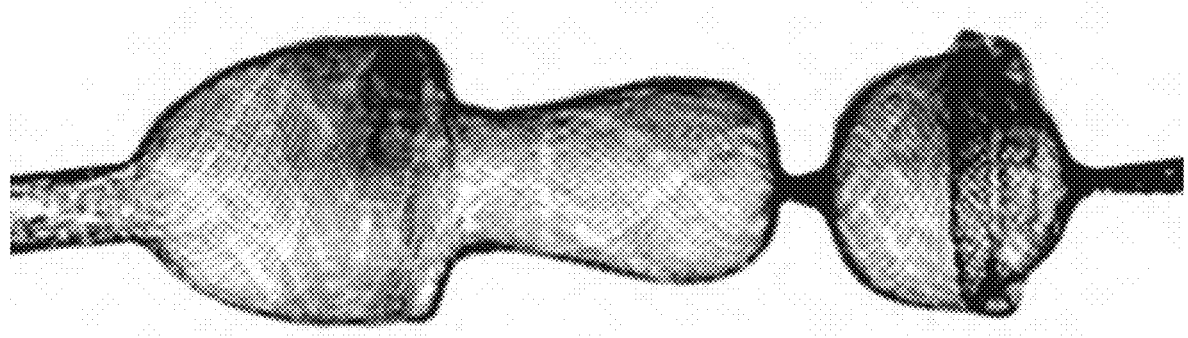
FIG. 26D illustrates an occlusive device comprising an outer and inner section.
Figure 26E:
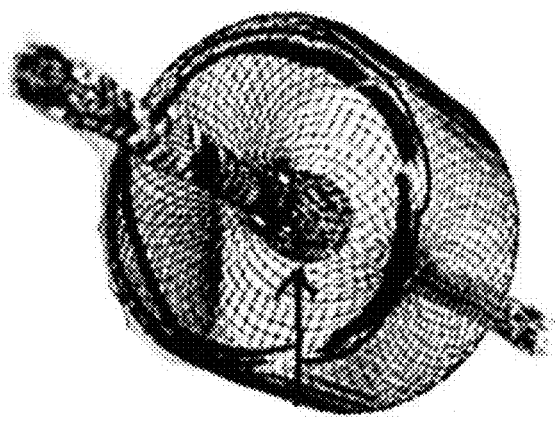
FIG. 26E illustrates an occlusive device comprising an outer and inner section.
Figure 26F:
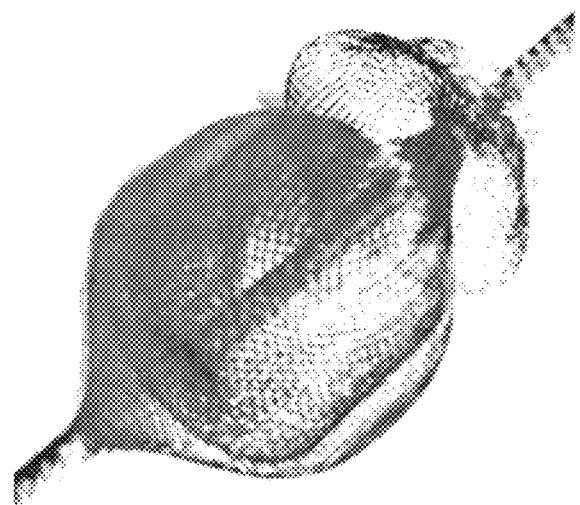
FIG. 26F illustrates an occlusive device comprising an outer and inner section.

As seen in FIGS. 25C and 25D, a mandrel 174 having a relatively larger cylindrical portion 174A and a relatively smaller, adjacent cylindrical portion 174B can be used to create the inwardly recessed braid termination points. The larger cylindrical portion 174A includes a recess 174C machined into its end and having a diameter such that the smaller cylindrical portion 174B can be positioned within. The recess is preferably curved or concave so that it is exposed even when the smaller cylindrical portion 174B is within it. The braid of the occlusive device is first positioned over both cylindrical portions 174A and 174B, and then a tube 176 is moved over the portion of the braid on the smaller cylindrical portion 174B and pressed against the recess 174C and a clip 177 is used to maintain the position of the tube 176. This movement pushes the braid into the recess 174C, allowing the mandrel 174 to be placed into an oven and heat set to impart the desired recessed shape. While the mandrel 174 is shown with one recessed end 174C and one smaller cylindrical portion 174A, both ends of the larger cylindrical portion 174A may include these features to create an occlusive device 172 with both proximal and distal recessed ends.

Figure 31A:
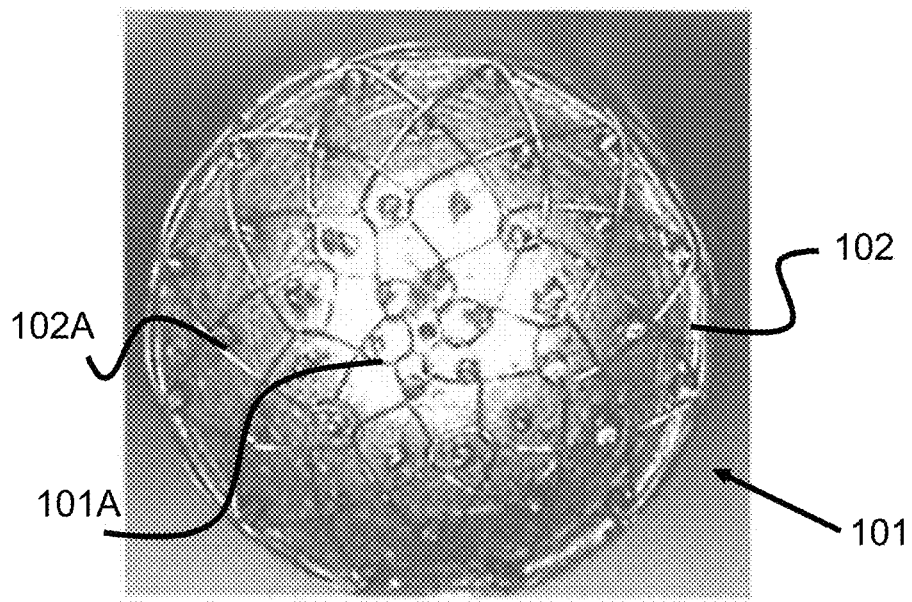
FIG. 31A illustrates a mandrel used to create an implant with closed ends.
Figure 31B:
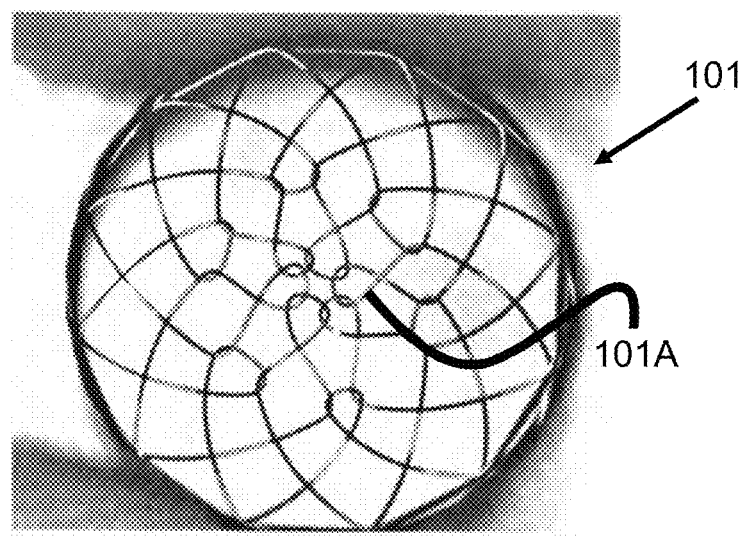
FIG. 31B illustrates alternate embodiments of an occlusive device with a braided, closed end.

FIGS. 31A-31B illustrate another embodiment of a braided occlusive device 101 with a fully braided end (or ends) that mitigates the complications associate with a protruding proximal or distal end. In other words, instead of closing the end of a cylindrically braided structure via welding or other techniques, one or more of the ends are braided closed without any termination of the wires at the ends of the device 101. In one embodiment, the device 101 comprises a cylindrical body having at least one end terminating in a plurality of loops 101A that are interconnected with each other and arranged in a circular pattern around an axis of the device 101, such that the end is free from any free ends of the underlying wire of the braid.

The device 101 can be braided on a mandrel 102 (seen in the end-view of FIGS. 31A and 31E) that has a desired body shape (e.g., cylindrical) and a domed or convex end (or both ends, if desired). Alternately, the mandrel ends may have a relatively flat shape, including the pins. The mandrel 102 includes a plurality of pins 102A protruding therefrom, which allows a user to wind or braid a wire in a desired braiding pattern around the end of the mandrel 102. Typical braiding techniques begin with a pre-woven cylindrical portion and then use a second set of wires to begin braiding inwardly toward a central axis of the device. This results in free ends of the wires at the edge of the cylindrical portion or at the center of the device's end.

Figure 31C:
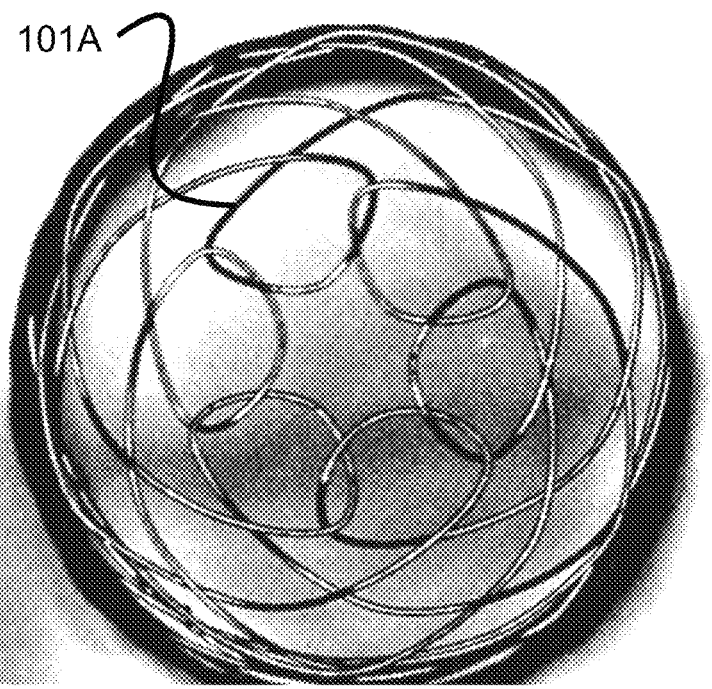
FIG. 31C illustrates alternate embodiments of an occlusive device with a braided, closed end.
Figure 31D:
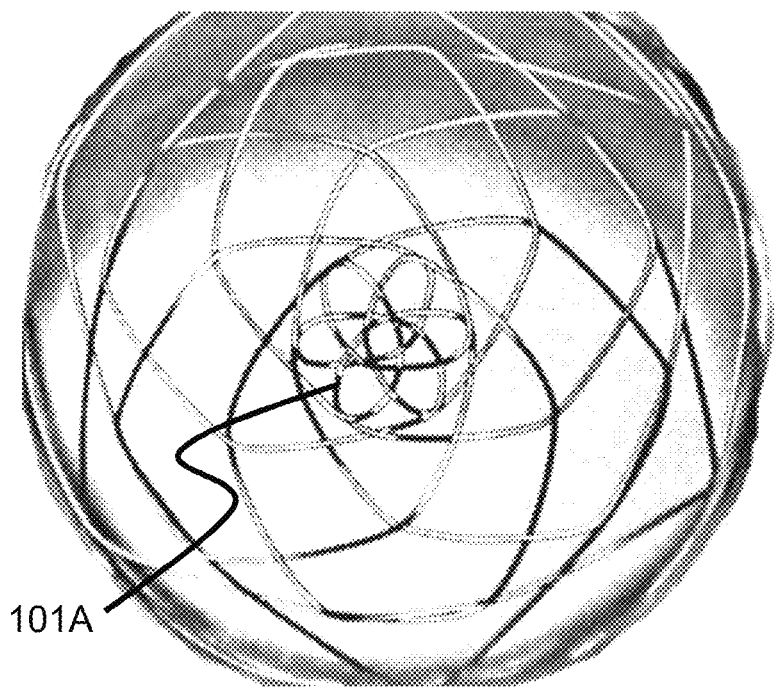
FIG. 31D illustrates alternate embodiments of an occlusive device with a braided, closed end.
Figure 31E:
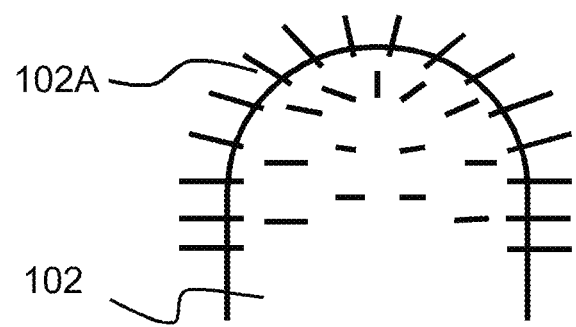
FIG. 31E illustrates a mandrel used to create an implant with closed ends.

The braid pattern of the device 101 begins at the center of the end of the mandrel 102. Instead of beginning the braid at this location with a free end of each of the plurality of wires, the braid begins substantially away from either free ends of each of the wires, such that there is enough length on each end of each of the wires to complete the braid down to a distal end of the occlusion device. In this respect, the braid begins with each of the plurality of wires forming loops 101A that are formed in a circular pattern around a center axis of the device 101. To help hold this proximal end together, each of the loops 101A are braided to interweave with at least two adjacent loops. If just two adjacent loops are interwoven with each other (i.e., on a left and right side) the loops 101A form a circular pattern having a center opening, as seen in FIGS. 31B and 31C. If the loops 101A are interwoven with diagonal or opposing loops 101A from the circular pattern, the device 101 will be substantially free of a center opening, such as in FIG. 31D. Additionally, the larger in size the loops 101A, the larger a potential center opening may be (FIG. 31C) and the smaller in size of the loops 101A the smaller any potential center opening may be (FIG. 31D). In this regard, the proximal end of the device 101 can be woven on the mandrel 102 such that it does it either has an axial center opening (as used for delivering embolic devices through, as described in connection with other embodiments of this specification), or such that is does not have an axial center opening.

Figure 31F:
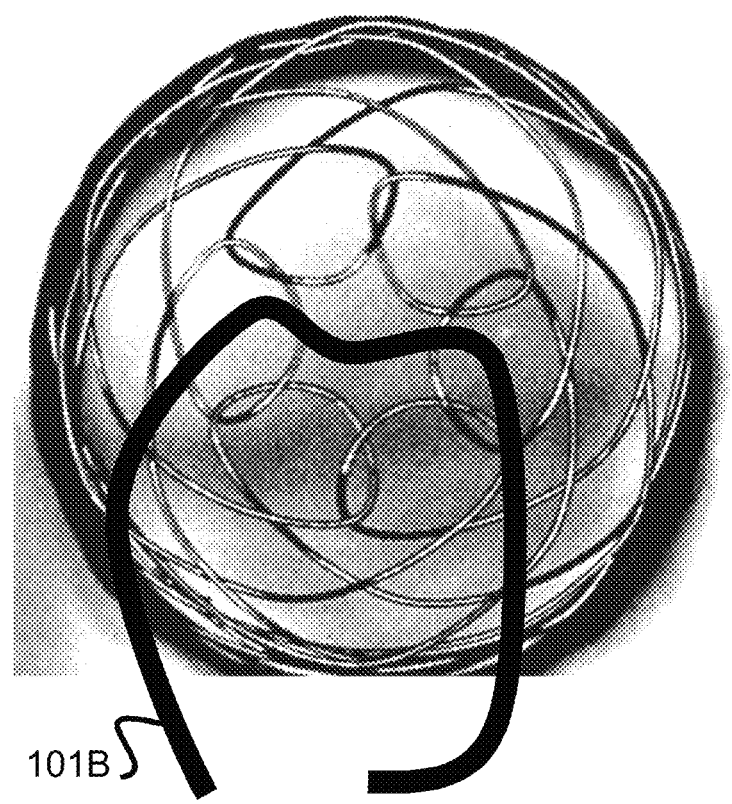
FIG. 31F illustrates alternate embodiments of an occlusive device with a braided, closed end.

After the desired braiding has been performed, the mandrel 102 and device 101 can be heat set to retain the device's configuration on the mandrel 102. The braided end of the device 101 can be connected to a pusher or catheter via a tether 101B that is tied or looped through a portion of the end, and can be releasable via one of the detachment mechanisms described elsewhere in this specification (FIG. 31F).

FIGS. 31C and 31D illustrate two alternate braiding patterns for an end of an occlusive device. FIG. 31C terminates with a plurality of interconnected circular loops arranged in an annular shape such that a middle or axial point of the device is open. FIG. 31D terminates with a plurality of oval, interconnected loops that are arranged over a middle or axial point of the device, such that the middle of the end of the device is closed.

FIGS. 26A-26F show different designs for intrasaccular devices, many of these designs incorporate multiple folding elements incorporated into the braiding pattern. The devices shown in these figures may be manufactured and heat set into a configuration whereby the various elements fold into each other to create the braided device. During delivery, the device would adopt an elongated, unfolded configuration where all the elements lay flat and linearly. Upon release from the delivery catheter, the braid would then adopt its folded configuration as the various layers sequentially push into the previously deployed layers. This folding effect is particularly helpful for occlusive purposes since the braids will be packed and increase the occlusive density of the mesh. Alternatively, the elongated, delivery shape of the device would also utilize the same folded shape—just stretched and elongated compared to the final, deployed shape. In one example, the distal end of the braid can utilize a longer stem, thus the stem would push and expand against the dome of the aneurysm providing a soft distal cap against which the rest of the braid will contact and fill out the rest of the aneurysm.

Figure 27A:
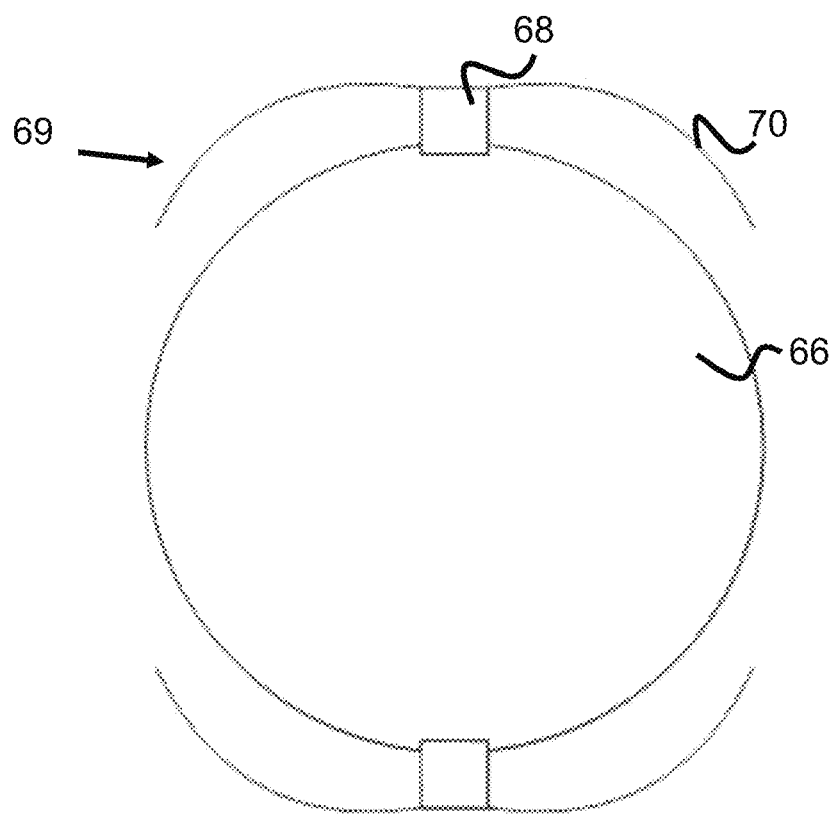
FIG. 27A illustrates an occlusive device comprising a sealing member.

FIG. 27A illustrates a sealing device 69 that can be used with an occlusive device 66, such as those described in this specification. The sealing device 69 includes a concave sealing portion 70 that is connected to the occlusive device 66 by a connecting member 68. A sealing device 69 can be delivered at the distal end of the device and/or at the proximal end of the device 66. If placed at the distal end of the device 66, the sealing device 69 would contact the dome of the aneurysm and provide a distal scaffold against which the rest of the mesh occlusive device 66 can fill the rest of the aneurysm. If placed at the proximal end of the device, the sealing device 69 would seal the neck of the aneurysm and prevent the occlusive device from sitting outside of the aneurysm. Additionally, if subsequent embolic devices were placed after the intrasaccular device (i.e. embolic coils or liquid embolic), the proximal sealing device 69 would provide a catch type element to prevent the embolic from falling out of the aneurysm. In one example, the sealing element is comprised of an umbrella-shaped series of wires which optionally utilize a membrane over the wires. If the sealing device 69 is connected to the occlusive device 66 within the aneurysm, the connecting member 68 has a plurality of hooks or other mechanical engagement members that can engage the occlusive device 66 during subsequent delivery. However, the sealing device 69 can also be connected to the occlusive device 66 prior to delivery, and therefore connecting member 68 can also include adhesives, welding, or other engagement mechanisms.

Figure 27B:
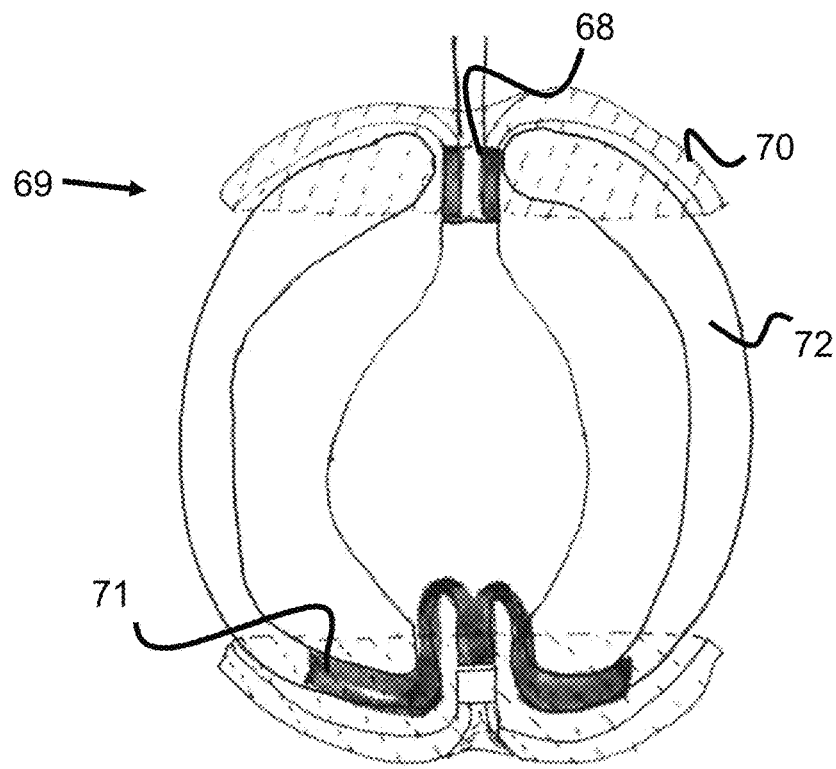
FIG. 27B illustrates an occlusive device comprising a sealing member.
Figure 27C:
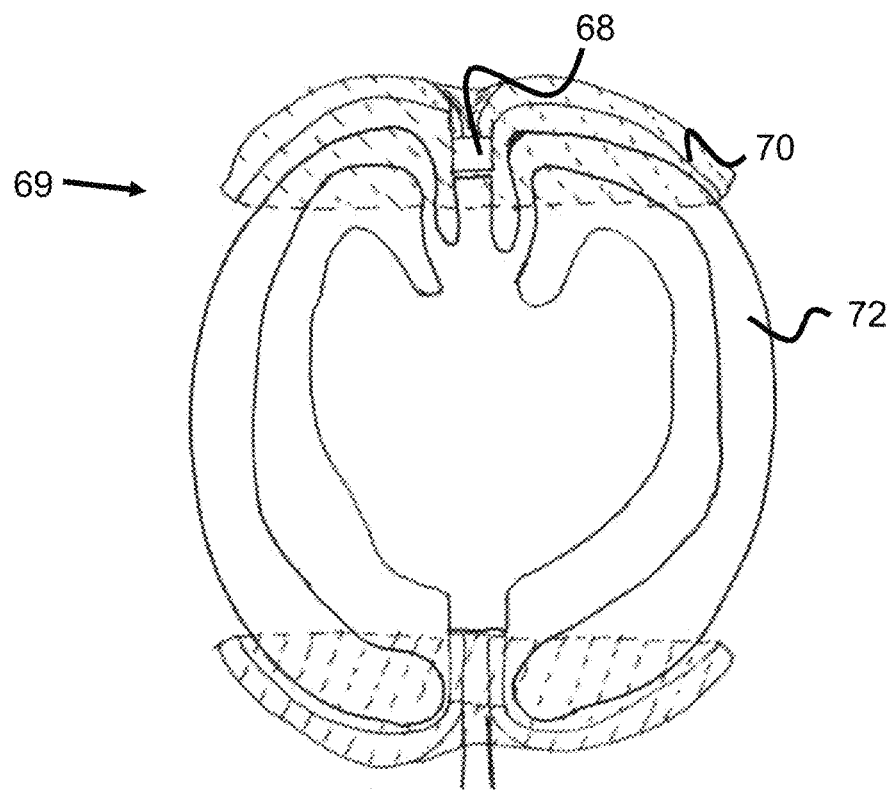
FIG. 27C illustrates an occlusive device comprising a sealing member.

FIG. 27B illustrates a proximal and distal sealing device 69 used in a similar arrangement with an occlusive device 72 that is formed into three folded layers of braided mesh. The connecting member 68 is connected to an inner filling member 71 and located inside of the layers of the occlusive device 72, augmenting the occlusion of the device. FIG. 27C illustrates a similar arrangement to that of FIG. 27B, except without the use of the inner filling member 71. The filling structure 17 may take the form of wires, hypotubes, or sheet-cut structures. The filling structure 17 can be shaped in a number of ways, such as a linear shape, wave-like shape, sinusoidal shape, and/or coiled-shape in order to promote occlusion of the target area. In one example, the filling structure may be made of nitinol wires from about 0.002"-0.005" in diameter. Other examples may utilize shape-setting polymers, cobalt-chromium, and spring-tempered stainless steel. In one example, each wire includes a tantalum coil for imaging and the tantalum coil wraps around the wire and extends either throughout the wire, or throughout a sufficient length of the wire to enable visualization of the device during the treatment procedure.

Figure 27D:
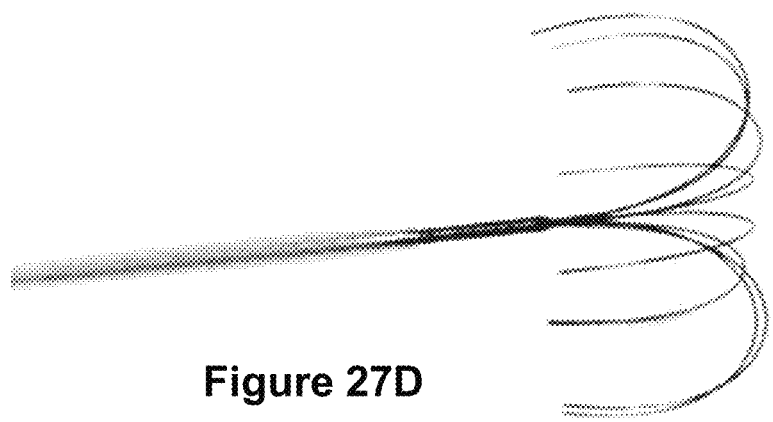
FIG. 27D illustrates an occlusive device comprising a sealing member.

FIG. 27d illustrates the wire understructure of the sealing device 69 without its mesh or membrane covering as it is delivered from a catheter. During delivery, the sealing device 69 would adopt a linear, elongated shape when collapsed within a catheter, and then would adopt an expanded, umbrella shape upon release.

Figure 27E:
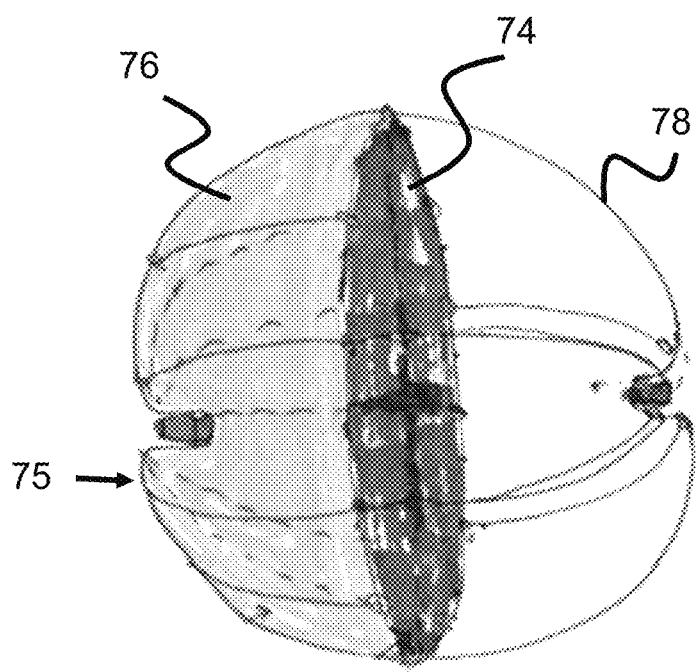
FIG. 27E illustrates an occlusive device comprising a structural portion and a mesh or membrane portion.
Figure 27F:
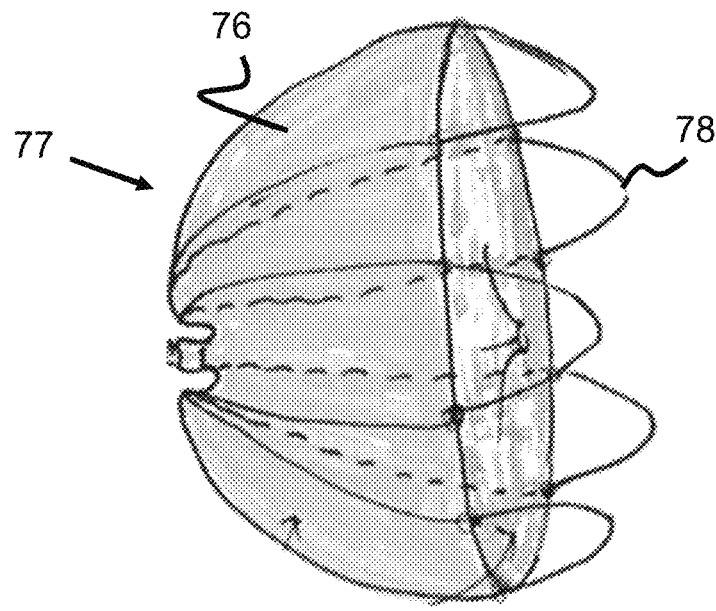
FIG. 27F illustrates an occlusive device comprising a structural portion and a mesh or membrane portion.

This sealing concept can be useful in other embodiments, for example a neck bridge element may utilize a proximal sealing device which blocks the neck of the aneurysm and other embolic material (such as coils or liquid embolic) may then be placed within the aneurysm and be cradled by the sealing device. In FIGS. 27E and 27F, the occlusive devices 75, 77 comprise a wire scaffold 78—in FIG. 27E the wires form a spherical shape and the device is meant to substantially fill the aneurysm, and in FIG. 27F the wires extend to form a partial sphere and the device is not meant to substantially fill the aneurysm. The proximal and distal ends of the wire scaffold 78 can utilize a sealing member 76, where all the wires are grouped together by the sealing member. The proximal end of the device can utilize a mesh or membrane, for instance, to seal the neck of the aneurysm. The neck seal may be delivered at the distal end of a pusher where the neck seal is detached, and then a catheter is subsequently introduced into the neck seal to deliver additional embolic agents such as coil and/or liquid embolic. Alternatively, the neck seal may be delivered at the distal end of an open lumen pusher (analogous to a microcatheter), the neck seal is placed within the target site, and the open lumen of the pusher is subsequently used to deliver additional embolic agents. The pusher is subsequently detached. The mesh/membrane can also be placed within the scaffold, as indicated by element 74 of FIG. 27E. Placing the mesh or membrane in such a manner will, in essence, create an occlusive region spanning from the neck of the aneurysm to the top of the membrane. Embolic (i.e. coil or liquid embolic) which is subsequently introduced would be captured within the region defined by the membrane. Different variations of this concept can involve a wire form scaffold, but where the mesh/membrane is placed all around the scaffold, solely around the middle of the scaffold, or solely at the distal end of the scaffold. The neck bridge would assume a collapsed configuration when housed within a delivery catheter and would adopt its expanded shape (see FIGS. 27E-27F) upon delivery, once released from the catheter. The mesh/membrane material used may be comprised of a polymer or a metallic material. The mesh/membrane can be affixed to the wire scaffold via adhesive, stitching, heat treatment, or other means. Though a wire scaffold is described, different variations are possible. For example, the scaffold may primarily utilize wires to create the scaffold—however, link elements (think of a jewelry pendant or chain link) may be selectively incorporated along the length of the wires to augment flexibility. Alternatively, the scaffold may be comprised of a laser cut sheet.

Figure 30:
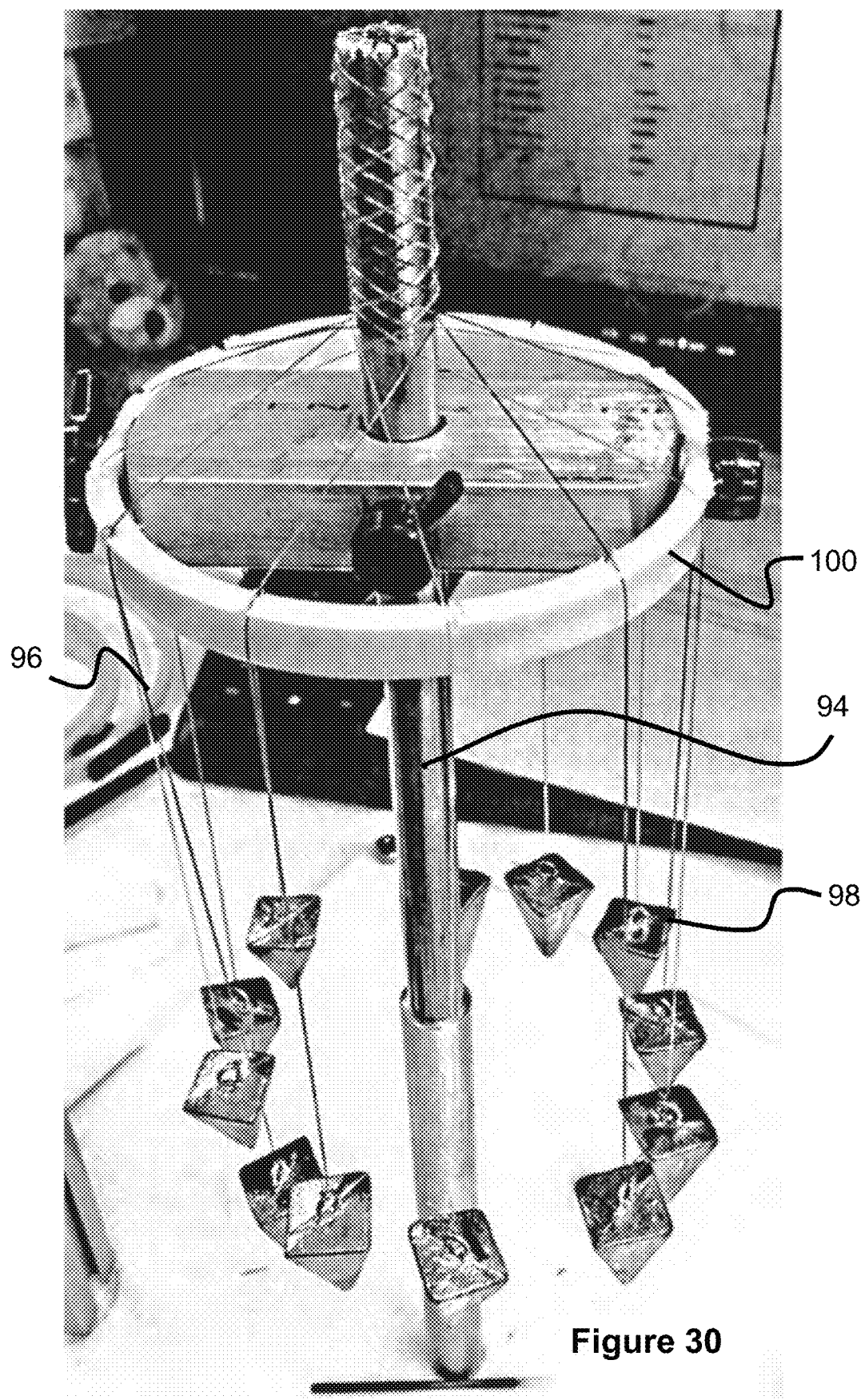
FIG. 30 illustrates a vertical braider.

FIG. 30 shows a mandrel and winding technique which can be used to wind a braid to create an occlusive device. This design utilizes gravity for tension and to wind the braid. The wires 96 comprising a braid are initially placed on mandrel 94. The top of the mandrel can have notches or grooves to accommodate the wires, or the wires can be placed at the top of the mandrel and affixed via tape or other means to keep tension on the wires initially. Weights 98 are placed at the bottom of the wires and a braid ring 100 is also utilized. The braid ring has notches to accommodate the wires and the braid ring is also selectively movable up and down the mandrel, but can be locked into place as well. The braid ring is used to control the angle of the wire braid, keeping the braid ring higher will result in a smaller braid angle and a denser braid configuration, while keeping the braid ring lower will result in a larger braid angle and a looser braid configuration. The user will lower the braid ring to keep a consistent tension and consistent braid angle on the braid as they wind the wires over the mandrel, the user will manually wind the various wires above and below each other to create the braid. To keep a consistent braid angle, the braid ring will be lowered as the user winds each incremental section of the braid. The device can be heat set after being wound to reinforce the shape.

Figure 32A:
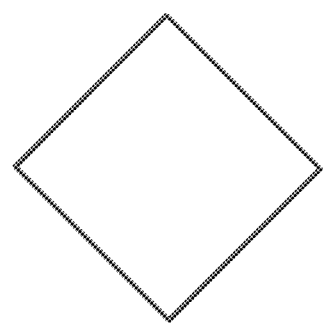
FIG. 32A illustrates a cross section of a braid created by a rotational braider.
Figure 32B:
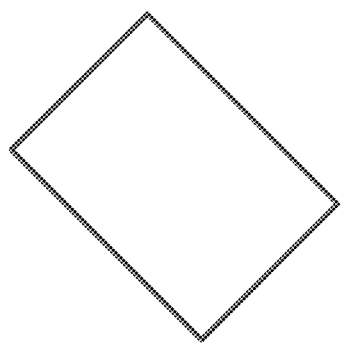
FIG. 32B illustrates a cross section of a braid created by a rotational braider.
Figure 32C:
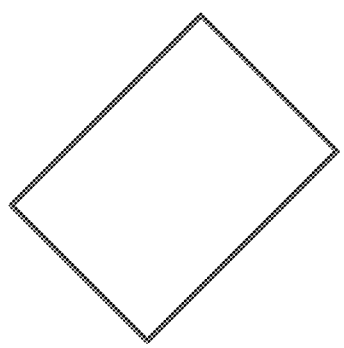
FIG. 32C illustrates a cross section of a braid created by a rotational braider.

Parts of the description have discussed the use of a braider to create a braided device, typically these braiders utilize a mandrel which moves longitudinally and a series of bobbins mounted within a carrier frame, where the bobbins rotate in various configurations within the carrier frame. The rotation of the bobbins and carriers coupled with the longitudinal movement of the mandrel enable the braiding of the device to occur. In another embodiment, a rotational braider may be used—that is instead of the bobbins housed within the braider moving around or the carriers moving around, the braider itself may also have freedom to rotate. FIG. 32A illustrates the typical shape of a wire braid intersection. Each line represents a wire, thus the cross points of four wires create the shapes shown—for ease of reference, we will refer to this 4-wire crossing point as a cell. Since the braid angle of FIG. 32A is consistent, a diamond-type cell shape is typically generated during the typical braiding process. Adding rotation to the braider itself, in addition to the rotation of the bobbins and carriers would allow additional possibilities. Adding rotation to the braider would shift the winding angle as the braider is winding over the mandrel, allowing for more off-kilter shapes such as the ones shown in FIGS. 32B-32C, instead of a diamond-type shape, the angles shift to more of a parallelogram type configuration. Rotating the frame clockwise will produce one shape, rotating the frame counterclockwise will produce another shape. This can be useful where, in selective regions of the manufactured braided device (i.e. occlusive device) you want areas with different flexibility—having the more stretched braid section shape of FIGS. 32B-32C will introduce a different stiffness profile than the shape of FIG. 32A. For example, perhaps the manufacturer wishes to create a braided device with a general stiffness throughout most of the device, but a difference stiffness profile in the middle. When the middle section of the braid is wound, the user can rotate the carrier frame to create the type of cell shapes shown in FIGS. 31B-31C, which will thus alternate the stiffness profile of the device within that particular region. Such a process can be automated, so for instance the braiding process is typically automated, so the carrier frame rotation capability can also be automated and can thought of as another variable in the winding operation. Other variables include the longitudinal speed of the mandrel, the rotational speed of the carriers and bobbins as they wrap the wires around the mandrel, the angles of the braids, etc.

Other embodiments may utilize a distal filling structure and a proximal neck-bridge structure. The filling structure may take the form of wires, hypotubes, or sheet-cut structures. The filling structure can be shaped in a number of ways, such as a linear shape, wave-like shape, sinusoidal shape, and/or coiled-shape in order to promote occlusion of the target area. In one example, the filling structure may be made of nitinol wires from about 0.002"-0.005" in diameter. Other examples may utilize shape-setting polymers, cobalt-chromium, and spring-tempered stainless steel. In one example, each wire includes a tantalum coil for imaging and the tantalum coil wraps around the wire and extends either throughout the wire, or throughout a sufficient length of the wire to enable visualization of the device during the treatment procedure. The neck bridge may comprise a mesh braid element which sits at the neck of the aneurysm or just within the aneurysm and would prevent the filling structures from falling out of the aneurysm. Alternatively, the neck-bridge may comprise a structure comprising a plurality of disc-shaped elements where one disc sits inside the aneurysm and other sits external to the aneurysm. The neck bridge may be a metallic braid (i.e. nitinol, stainless steel, cobalt-chromium) or polymeric.

Figure 35:
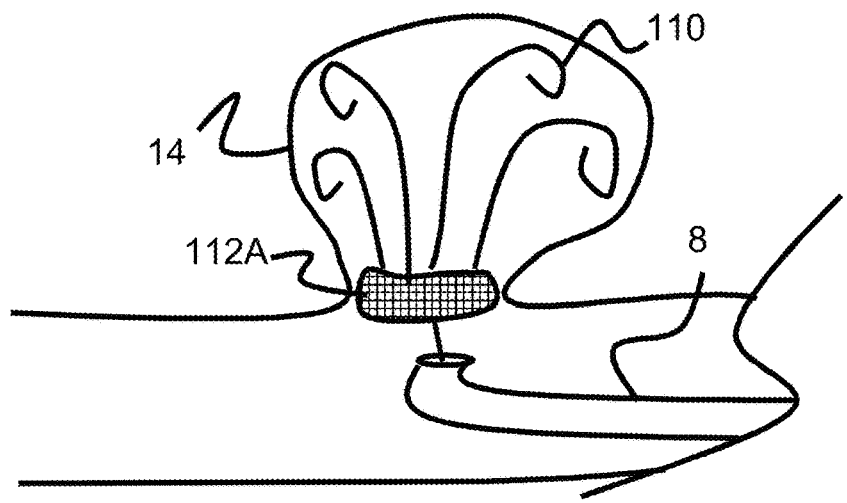
FIG. 35 illustrates an occlusive device comprising a neck bridge element.

FIG. 35 shows a distal wire filling structures 110 and proximal mesh neck-bridge structure 112A used to occlude an aneurysm. The device is delivered from a catheter 8. In one example, the distal filling structures 110 and proximal mesh/neck-bridge structure 112A are connected and the whole system may be pushed via a core wire-based pushing system where a detachment system is incorporated at the end of the core wire and proximal of the mesh/neck-bridge to detach the device. Any mechanical, thermal, or electrolytic detachment system may be used, including the other detachment concepts disclosed in this specification.

Figure 36:
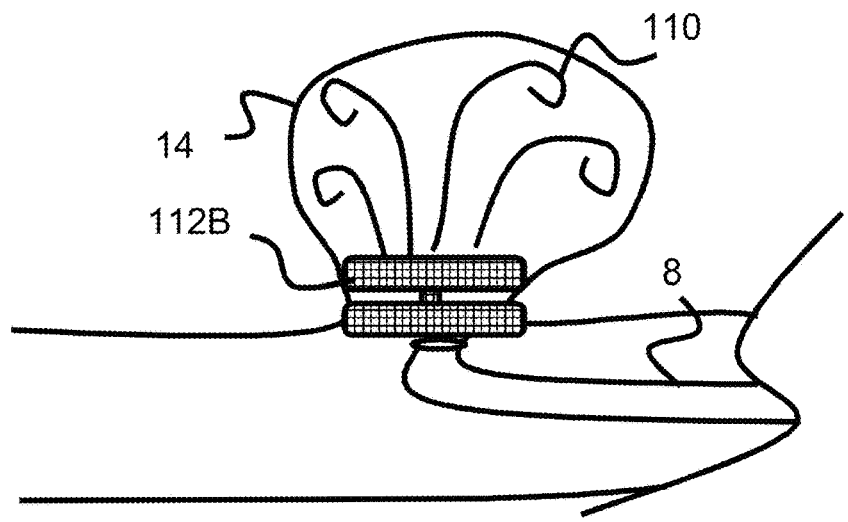
FIG. 36 illustrates an occlusive device comprising a neck bridge element.

FIG. 36 illustrates an embodiment similar to that of FIG. 34, except having a dual-disc neck bridge structure 112B. In this example, the neck bridge 112B may comprise a plurality of disc-shaped elements where one disc sits inside the aneurysm and the other disc sits outside the aneurysm.

In one embodiment, the filling structures 110 are affixed to a distal portion of the neck bridge 112A/112B. When delivered, the whole system would be collapsed within the catheter 8 with the filling structures 110 sitting distal of the neck bridge. In another embodiment, the neck bridge structure 112A/112B would be preplaced at the distal end of the catheter 8, and sit outside the catheter 8. In one embodiment, the catheter 8 extends through the neck bridge 112A/112B to provide a lumen for delivery of additional embolic agents through the neck bridge 112A/112B and into the aneurysm 14.

In another embodiment, the neck-bridge structure 112B shown in FIG. 34 may utilize one or more lumens and the filling structures are delivered through the one of more lumens, through the neck bridge 112B, and into the aneurysm 14. The filling structures would be delivered through the catheter and through the neck bridge, and would be placed through the neck bridge after the neck bridge is deployed.

Figure 37:
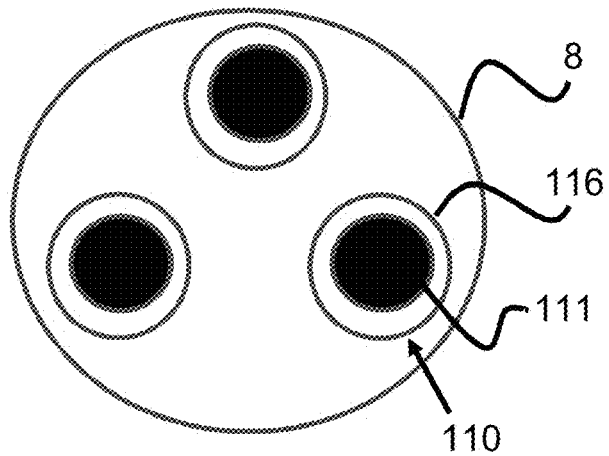
FIG. 37 illustrates an occlusive device comprising a neck bridge element.

In one embodiment, the filling structures 110 are affixed to the neck bridge 112A/112B which is proximal to the filling strictures 110. The filling structures 110 and attached neck bridge are pushed through the catheter 8 via a proximal pushing system. A detachment system (electrolytic, thermal, mechanical, other detachment systems described in the specification or previously incorporated by reference) link the pusher to the neck bridge. The pusher is used to push the neck bridge and filling structures out of the catheter, and the detachment system is then used to detach the system from the pusher, and the pusher is then withdrawn. FIG. 37 shows a cross sectional view of such an arrangement in which the filling structures 110 are affixed to the distal portion of the neck bridge (not shown), and the entire device is delivered through a catheter 8. Three filling structures are used. The filling structures 110 include a wire 111 surrounded by a radiopaque coil 116 to aid in visualization. The radiopaque coil 116, in one example, comprises tantalum or tungsten and has a 0.001" filar, which is a diameter that is slightly larger than the wire 111 since the coil 116 sits around the wire 111. The neck bridge 112A/112B sits proximally of the filling structures. A proximal pusher, such as a core wire pusher, is connected to the neck bridge 112A/112B. A detachment system, utilizing thermal, mechanical, or electrolytic means can separate the pusher from the neck bridge 112A/112B. Any of the detachment systems discussed in the specification, and any of the systems incorporated by reference can also be used.

Figure 38:
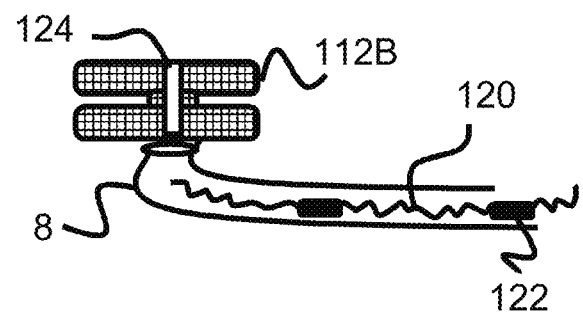
FIG. 38 illustrates an occlusive device comprising a neck bridge element.
Figure 39:
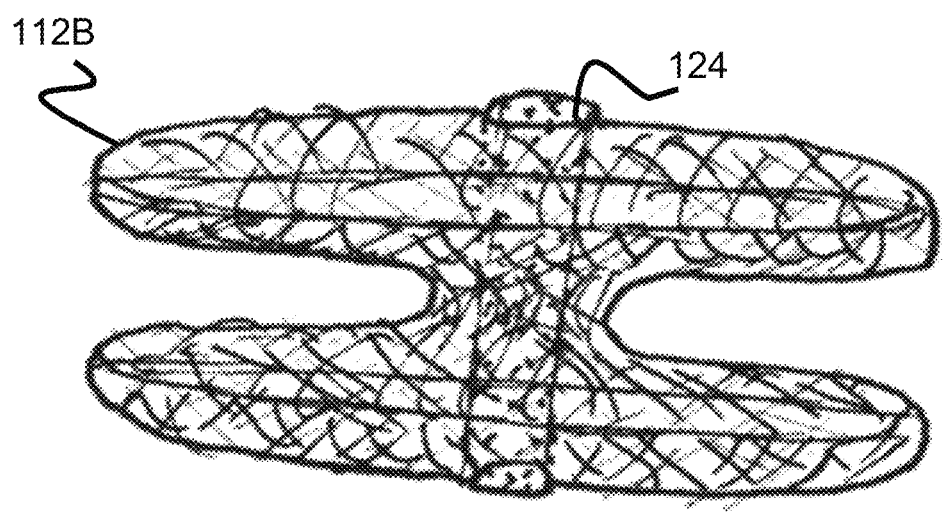
FIG. 39 illustrates an occlusive device comprising a neck bridge element.

FIGS. 38 and 39 show another embodiment in which a distal neck bridge structure 112B (or alternately 112A) includes an internal channel 124 connected to the catheter 8 so that a continuous lumen is present through the neck bridge 112B. The neck bridge 112B may sit distal of the catheter 9. In another example, a portion of the neck bridge 112B would sit distal of the catheter 8 and a portion sits within the catheter 8 and a detachable pusher element is used to push the neck bridge 112B out of the catheter 8 when the catheter 8 is placed in an appropriate location (i.e. near the aneurysm or treatment site). Alternatively, the catheter 8 can be retracted to expose the entire neck bridge 112B. Since the neck bridge 112B contains a lumen, when the neck bridge is appropriately placed, the lumen can be used as a conduit to push embolic agents (such as embolic coils) through the neck bridge 112B into the treatment site (e.g., aneurysm). The neck bridge 112B would prevent the embolic coils from falling out of the treatment site and migrating elsewhere. The neck bridge may be pushed out of the catheter 8 so that the catheter 8 can be withdrawn, or alternatively the catheter 8 can include a detachment system (thermal, mechanical, electrolytical, other detachment described herein, or other detachment systems incorporated by reference within the specification) to detach the catheter from the neck bridge.

U.S. Pub. No. 20150173772 discloses an embolic coil system utilizing detachable elements along the length of the coil to create a variable detachment system where selective lengths of the coil can be deployed within a target treatment site, and is hereby incorporated by reference in its entirety. One embodiment, shown in FIGS. 38-39, can utilize a variable detachment coil system along with the neck bridge concept. The variable detachment system utilizes a contact element on the catheter to interact with the links in between the embolic coil segments, the links include a degradable element which degrades when the catheter contact element electrically interacts with the coil links to sever a segment of the coil. Element 124 represents the inner lumen which spans the interior of the neck bridge 112 in FIG. 39, this lumen is connected to capsule 126 which comprises a degradable linkage which severs the neck bridge from the catheter delivery system. The embolic coils 120 which are pushed through the catheter (see FIG. 38) include links 122, the links electrically interact with capsule element 128 (see FIG. 40) to detach appropriate segments of the embolic coil within the vasculature. Catheter 8 provides the delivery platform for both the neck bridge (connected distally to the catheter) and for the embolic coils which are delivered through the catheter. The inner lumen and attached neck bridge are separable from the catheter via degradable capsule 126. The capsule can use detachment means, as discussed earlier, to detach the neck bridge 112 and inner lumen 124 spanning the interior of the neck bridge, from the catheter. Several wires 130 are used to convey current to capsules 126 and 128, a voltage source (i.e. battery) sits at the proximal end of the system and conveys current between the battery and the capsules. Inner lumen 24 may comprise a number materials including polymer, metallic, metallic mesh.

Previous embodiments discussed utilizing a neck bridge which either sits within or at the neck of an aneurysm (FIG. 35) or which has a portion sitting inside the aneurysm and another sitting outside (FIG. 36). Another embodiment would utilize a floating neck bridge, the neck bridge would be deployed within the aneurysm and as either the filling structures or embolic coils were deployed into the aneurysm, these embolic materials would occupy the internal space of the aneurysm and eventually push the neck bridge down so it seals the neck of the aneurysm. In one example, catheter 8 displayed in FIGS. 35-40 is a microcatheter with a diameter of 0.017"-0.021".

Figure 41:
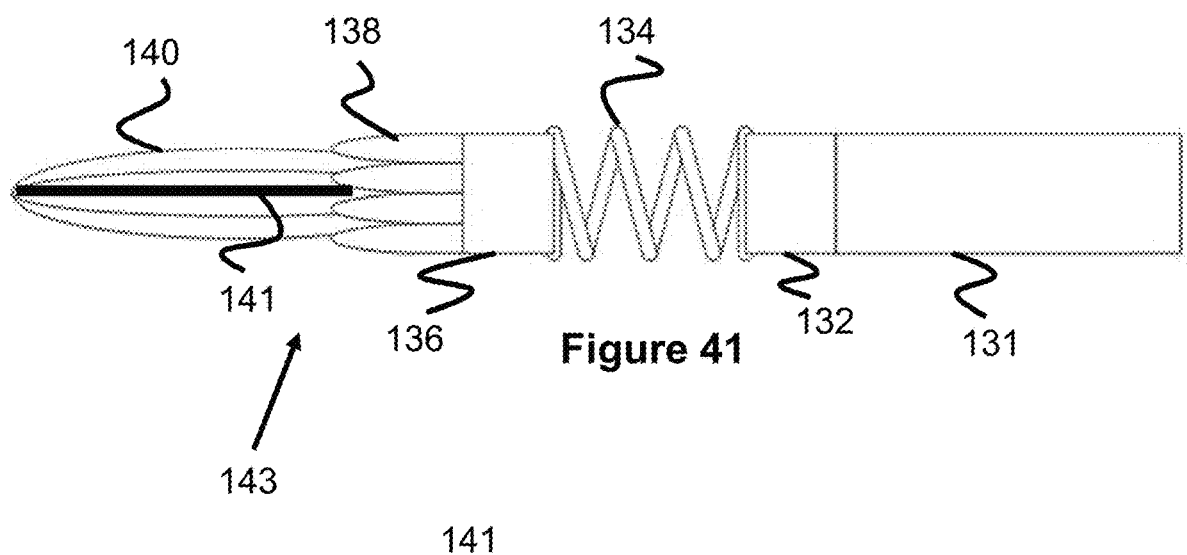
FIG. 41 illustrates an occlusive device comprising struts and a distal contact portion.
Figure 42:
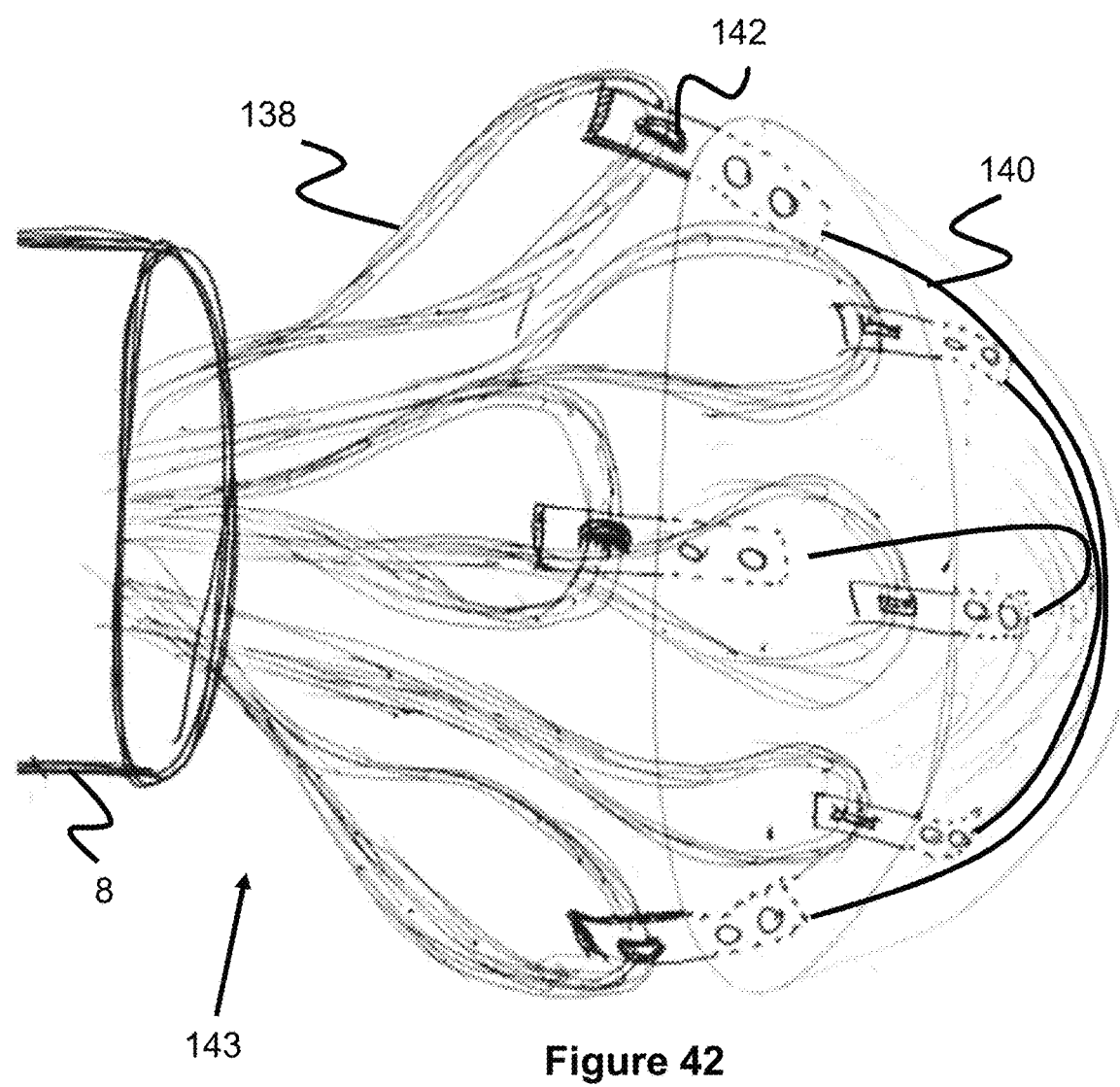
FIG. 42 illustrates an occlusive device comprising struts and a distal contact portion.

Yet another embodiment of an occlusive device 143 is shown in FIG. 41 in a compressed, elongated state during delivery in a catheter 8 and in FIG. 42 in an expanded configuration emerging from the catheter 8. The device 143 includes a number of structural loops or struts 138 connected to a distal occlusive portion 140. The distal occlusive portion 140, when used in an aneurysm, creates a dome or concave occluding region in the aneurysm while the struts 138 help expand the occlusive portion 140 and fill out the area underneath the occlusive portion 140.

Connecting structures 142 are fixed to the to the distal contact portion 140 (e.g., via adhesive or welding) and are fixed to the struts 138 (e.g., via a loop through which the struts 138 pass through), thereby connecting the struts 138 to the distal occlusive portion 140. The struts can be comprised of a metal or polymer, such as nitinol wire or a hypotube—although radiopaque items can also be used to aid in imaging. The distal occlusive portion 140 can either have a pre-set curved shape, or it can comprise a malleable, thin material so to conform the shape of the aneurysm. In one example, distal occlusive portion 140 is a thin film polymer (e.g., PTFE, ePTFE, polyethylene) or metallic (e.g., nitinol, stainless steel) material. The struts 138 help control the expansion of the distal contact portion and help ensure the device 143 deploys gradually.

A proximal end of the struts 138 are connected to a cylindrical collector band 136, for example by passing through apertures in the collector band 136. A coil 134, in one example stainless steel, is connected to a proximal end of the collector band 136 and to a distal end of a proximal band 132 on the pusher 131, thereby helping to propel the struts, as well as distal occlusive portion 140, open. The coil 134 adopts a compressed shape when the device 143 is within a catheter 8, since the struts 138 also adopt a compressed, elongated shape. The coil 134 thus has stored energy and as the device 143 is delivered and the struts 138 start to open up, the coil 134 discharges this stored energy which helps to further expand the struts as well as the attached distal contact portion 140.

The pusher 131 can comprise a core wire or hypotube system and allows the user to manipulate the device 143 through the catheter 8 and through the vasculature. A detachment system can be included at a location distal of the pusher. In one example, coil 134 is also part of the detachment system and a severable tether is located within the lumen of the coil 134. Wires can connect on either end of the coil and these wires connect to a voltage source such as a battery at the proximal end of the system, allowing the user to initiate a detachment sequence (i.e. by pushing a button) to heat the coil and sever the tether to detach the device from the pusher. The detachment system may be flush or distal to the coil 134 so that the coil 134 does not get propelled into the vasculature. In one example, the detachment system utilizes a tether spanning the collector band 136 through coil 134, and the coil is firmly connected to element 132. Thus when the detachment sequence is initiated and the device is deployed, the tether will sever but the coil will remain attached to the pusher since the proximal end of the pusher is attached to proximal band 132.

A tensioning element 141 can also be used, connecting the distal occlusive portion 140 to struts 138. The tensioning element 141 may be a thin wire or tether and would help control the expansion of distal portion 140 and struts 138 upon delivery so the opening is slowed or less abrupt.

Figure 40:
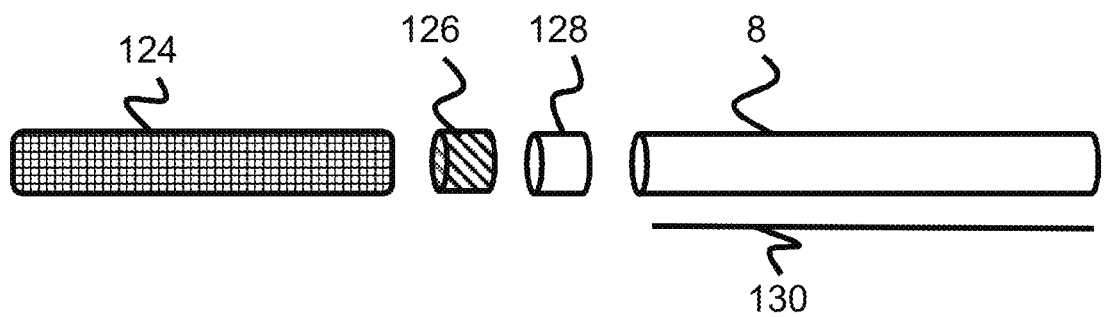
FIG. 40 illustrates an occlusive device comprising a neck bridge element.

The struts 138, in one example, are heat treated to have a shape memory opened shape as shown in FIG. 40, this shape memory would make the struts 138 open quickly to adopt their shape memorized open shape, and the tether would help control the opening of the device during delivery. The tensioning element 141, alternatively, may span the area between distal occlusive portion 140 and the pusher 131, or proximally at the base of the struts 138, band 136, coil 134, element 132, or pusher 131. Affixing the proximal end of the tether to a non-strut element would have the advantage of fixing it to an element that does not expand, resulting in a very controlled deployment. Affixing the proximal end of the tether to a strut 138 would still constrain the expansion, but not as much, since the proximal end is secured to something which expands on deployment. The location of the proximal end of the tether may be customized based on whether the user wants or more or less controlled expansion of the device upon deployment—materials used in the device, and size of the device would be important variables in play.

Figure 43:
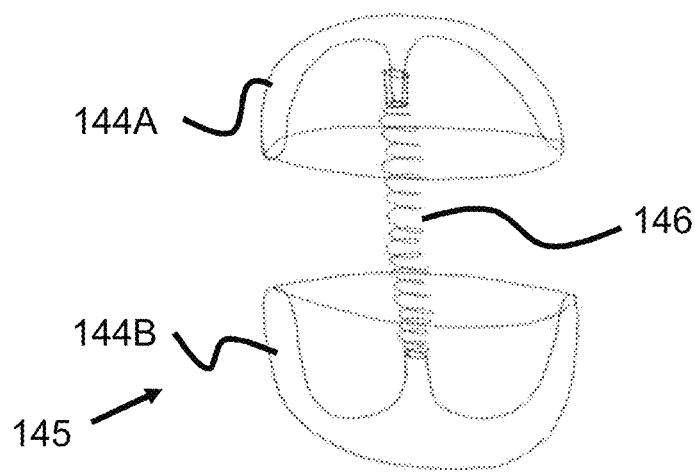
FIG. 43 illustrates an occlusive device comprising a top element, bottom element, and coil connecting component.
Figure 44:
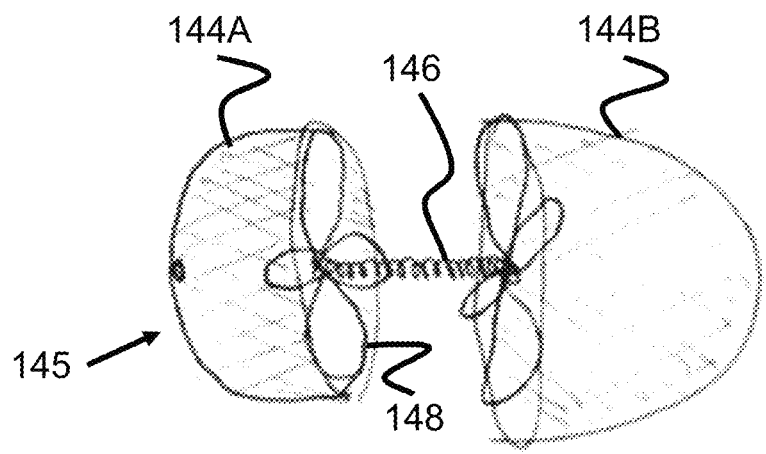
FIG. 44 illustrates an occlusive device comprising a top element, bottom element, and coil connecting component.
Figure 45:
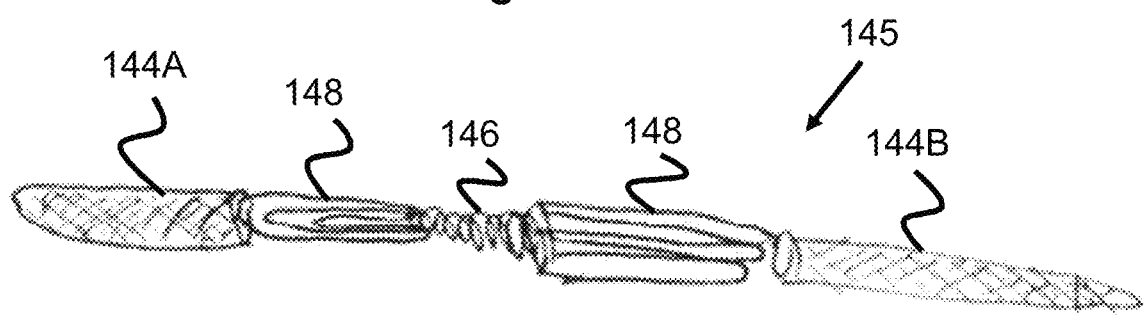
FIG. 45 illustrates an occlusive device comprising a top element, bottom element, and coil connecting component.

FIGS. 43-45 illustrate an occlusive device 145 having a concave top occlusive element 144A and a concave bottom occlusive element 144B to, respectively, expand against the dome and the neck of an aneurysm. The top and bottom elements 144A, 144B can be comprised of a variety of components, including metallic mesh, metallic sheets, and polymer. A coil 146 connects to the top and bottom occlusive elements 144A, 144B, connecting both elements 144A, 144B while allowing for variation in distance to accommodate different aneurysm sizes. The top element 114A is deployed first into the aneurysm and the bottom element 1146 is the last element out of the catheter. As seen in FIGS. 44 and 45, the device 145 may optionally include a frame 148 that expands within the top and bottom elements 144A, 144B. The frame 148 has a plurality of loops that expand radially across the openings of the concave opening of the elements 144A, 144B, acting as a scaffold for the opening and closing of the top and bottom elements, while also providing for a more controlled expansion and contraction of the device. FIG. 45 shows the device 145 in a collapsed configuration which it would adopt during delivery via a catheter. The frame elements 148, when collapsed, would sit over a portion of the coil (think of an umbrella frame when contracted compared to when expanded); when expanded the frame elements would sit flush or within the top and bottom elements, respectively.

Other embodiments may utilize the distal filling structure 110 described earlier and shown in FIGS. 35-36, but utilized with the device shown in FIG. 1 which includes a retention portion 10 and holding portion 12.

Previous discussion discussed various mandrels and winding techniques used to create an occlusive device. Another embodiment utilizes a removable mandrel, where fracturing, chemical dissolution, or other techniques can be used to remove the mandrel after the manufactured device is braided over the mandrel. The manufactured device may be a number of devices, such as braided therapeutic devices, including occlusive devices. Conventional braiding technologies utilize braiding a device over a mandrel, heat setting the device over the mandrel, and subsequently removing the mandrel. The mandrel can optionally include a number of pins around which the device is braided. Where a non-cylindrical, tapered occlusive device is created (i.e. one where the ends are smaller than the center), removing the mandrel can be difficult due to the tapered shape of the mandrel and occlusive device. One method of solving this issue is to use a mandrel which can be removed via mechanical means (i.e. fracturing) or chemical means (i.e. chemical dissolution) to remove the mandrel and leave the braided device.

In one embodiment, the mandrel is comprised of ceramic or glass. Ceramic and glass are both highly brittle, therefore the mandrels can be mechanically fractured by a hammer after the device is formed to remove the mandrel. If a glass mandrel is used, the glass can be coated with a silicone or latex material to prevent the device wound over the mandrel from slipping. In another embodiment, an aluminum mandrel is used and a concentrated sodium hydroxide solution is used to dissolve the mandrel. A concentrated (i.e. 1-10 M) sodium hydroxide solution may be used with a high temperature (i.e. 100-150 degrees F.) along with fluid conviction. The aluminum mandrel will slowly dissolve, but the technique will not dissolve other materials such as nitinol that might be used to wind the interventional device. Thus the mandrel will disappear and the device will remain. In another embodiment, the mandrel is sand cast. A sand cast mandrel is removable via a fluid jet and will simply leave sand once the formed mandrel breaks up. In one example, the mandrel has an aluminum core is used and a sand cast is built over the top of the aluminum core. Another embodiment may utilize a removable mandrel comprising a wireform structure, similar to the braided structure created over the mandrel. Thus the mandrel comprises a first braid, and a second braided interventional device is wound over the braided mandrel. The braided mandrel can be easily compressed to remove the braided interventional device. The braided mandrel should comprise any wire structure that balances strength and compressibility and can withstand the high heat-set setting temperature, examples include 316 stainless steel or 321 stainless steel. Another embodiment utilizes a mandrel comprising a first layer (i.e. a typical metallic mandrel) and a second layer, where the second layer comprises any of the removable mandrel elements described herein, in order to create a dual or multiple-layered braided interventional device. The user winds the first layer of the device over the base mandrel. A second mandrel layer, which is removable, is then placed over the first mandrel layer and first braided layer of the interventional device. The second layer of the interventional device is then wound over the second (removable) mandrel layer. The removable mandrel section is then removed, leaving the first mandrel and the multiple layered interventional device. Though this process was described to create a two or dual-layer device, additional removable mandrels may be added to create a three, four, five, etc. layer braided interventional device.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An occlusive system comprising:
an occlusive device having a proximal opening;
a pusher releasably connected to the occlusive device; the pusher having a lumen therethrough, the lumen spanning along an entire length of the pusher, wherein the pusher includes one or more openings;
a detachment coupling detachably linking the pusher and the occlusive device; and
a heater coil positioned within the one or more openings of the pusher; and,
wherein the detachment coupling is positioned externally of the pusher lumen so as to form a continuous passage between the lumen of the pusher and the proximal opening of the occlusive device.

2. The occlusive system of claim 1, wherein the detachable coupling is positioned circumferentially external of a distal section of the pusher.

3. An occlusive system comprising:
a pusher having an elongated passage therethrough, wherein the pusher includes one or more openings;
an occlusive device releasably connected to the pusher, the occlusive device having a proximal opening;
a detachment coupling detachably linking the pusher and the occlusive device; and
a heater coil positioned within the one or more openings of the pusher; and,
wherein the detachment coupling is positioned externally of the elongated passage of the pusher so as to form a throughway extending between the elongated passage of the pusher and the proximal opening of the occlusive device.

4. The occlusive system of claim 3, wherein the detachment coupling is positioned distal of a distal end of the pusher.

5. The occlusive system of claim 4, wherein the detachment coupling is a ring-shaped element.

6. The occlusive system of claim 5, wherein the ring-shaped element includes one or more apertures.

7. The occlusive system of claim 6, wherein the one or more openings of the pusher comprise one or more slots aligned with the one or more apertures of the ring-shaped element.

8. The occlusive system of claim 7, further comprising a tether linking the ring-shaped element to the distal end of the pusher, wherein the tether extends between the one or more slots of the pusher and the one or more apertures of the ring-shaped element.

9. The occlusive system of claim 8, wherein the heater coil is positioned within the one or more slots of the pusher.

10. An occlusive system comprising:
a delivery tube having a delivery lumen therethrough configured for passage of an embolic material, wherein the delivery tube includes one or more openings;
an occlusive device releasably connected to a distal section of the delivery tube;
a detachment coupling detachably linking the delivery tube and the occlusive device; and
a heater coil positioned within the one or more openings of the delivery tube; and,
wherein the detachment coupling is positioned externally of the delivery lumen so as to form a continuous passage extending between a proximal end of the delivery tube and a distal end of the delivery tube, so as to allow passage of the embolic material through the delivery tube.

11. The occlusive system of claim 10, wherein the occlusive device is a mesh composed of one or more wires.

12. The occlusive system of claim 11, wherein the occlusive device is an aneurysm occluding intrasaccular mesh.

13. The occlusive system of claim 10, wherein the detachment coupling is positioned distal of the distal end of the delivery tube.

14. The occlusive system of claim 10, wherein the detachment coupling is positioned circumferentially external of the distal section of the delivery tube.

15. The occlusive system of claim 10, wherein the delivery tube is a microcatheter.

* * * * *